US012702277B2

(12) United States Patent
Yang et al.

(10) Patent No.: US 12,702,277 B2
(45) Date of Patent: Aug. 11, 2026

(54) COLLISION AVOIDANCE IN SURGICAL ROBOTICS BASED ON DETECTION OF CONTACT INFORMATION

(71) Applicant: Auris Health, Inc., Redwood City, CA (US)

(72) Inventors: Bo Yang, Mountain View, CA (US); Yanan Huang, Sunnyvale, CA (US); Hossein Taheri, Foster City, CA (US); Babak Kianmajd, Hayward, CA (US); Ying Mao, San Mateo, CA (US)

(73) Assignee: Auris Health, Inc., Santa Clara, CA (US)

( * ) Notice: Subject to any disclaimer, the term of this patent is extended or adjusted under 35 U.S.C. 154(b) by 275 days.

(21) Appl. No.: 18/116,253

(22) Filed: Mar. 1, 2023

(65) Prior Publication Data

US 2023/0200629 A1 Jun. 29, 2023

Related U.S. Application Data

(63) Continuation of application No. PCT/IB2021/058548, filed on Sep. 20, 2021.

(Continued)

(51) Int. Cl.
*A61B 1/00* (2006.01)
*A61B 34/20* (2016.01)

(52) U.S. Cl.
CPC .......... *A61B 1/00149* (2013.01); *A61B 34/20* (2016.02)

(58) Field of Classification Search
CPC ... A61B 1/00149; A61B 34/20; A61B 1/0016; A61B 1/307; A61B 2034/2051;

(Continued)

(56) References Cited

U.S. PATENT DOCUMENTS 7,720,322 B2 5/2010 Prisco
8,620,473 B2 12/2013 Diolaiti et al.

(Continued)

FOREIGN PATENT DOCUMENTS

CN 107414860 A 12/2017
EP 3266571 A2 1/2018

(Continued)

OTHER PUBLICATIONS

Budiharto, Widodo, Djoko Purwanto, and Achmad Jazidie. "A Novel Static and Moving Obstacles Avoidance Method Using Bayesian Filtering for Service Robot." *2010 Second International Conference on Advances in Computing, Control, and Telecommunication Technologies.* IEEE, 2010.

(Continued)

*Primary Examiner* — Khoi H Tran
*Assistant Examiner* — Tien Minh Le
(74) *Attorney, Agent, or Firm* — FBT GIBBONS LLP

(57) ABSTRACT

Robotic systems can be capable of collision detection and avoidance. A medical robotic system can include a first kinematic chain and one or more sensors positioned to detect one or more parameters of contact with one or more portions of the first kinematic chain. The medical robotic system can be configured to cause adjustment of a configuration of the first kinematic chain from a first configuration to a second configuration based on a constraint determined from the one or more parameters of contact with the first kinematic chain detected by the one or more sensors.

19 Claims, 47 Drawing Sheets

Related U.S. Application Data

(60) Provisional application No. 63/086,036, filed on Sep. 30, 2020.

(58) Field of Classification Search
CPC ............ A61B 2034/2061; A61B 90/57; A61B 2017/00477; A61B 2034/2065; A61B 2090/065; A61B 2090/066; A61B 2090/502; A61B 34/37; A61B 2034/301; A61B 2034/302; A61B 2090/309; A61B 2090/376; A61B 90/00; A61B 34/30; A61G 13/101; A61G 13/04; B25J 9/0084; B25J 9/1676; B25J 13/085; B25J 9/1689; G05B 2219/45118; G05B 2219/39082
See application file for complete search history.

(56) References Cited

U.S. PATENT DOCUMENTS

| | | | |
|---|---|---|---|
| 9,259,282 B2 | 2/2016 | Azizian et al. | |
| 9,424,468 B2 | 8/2016 | Shimizu et al. | |
| 9,763,741 B2 | 9/2017 | Alvarez et al. | |
| 9,943,962 B2 | 4/2018 | Sattler et al. | |
| 10,219,868 B2 | 3/2019 | Weir | |
| 10,420,616 B2 | 9/2019 | Kostrzewski et al. | |
| 10,717,194 B2 | 7/2020 | Griffiths et al. | |
| 10,905,499 B2 | 2/2021 | Rafii-Tari | |
| 10,987,178 B2 | 4/2021 | Shelton, IV et al. | |
| 11,011,077 B2 | 5/2021 | Garcia Kilroy et al. | |
| 11,058,493 B2 | 7/2021 | Rafii-Tari et al. | |
| 11,896,318 B2 | 2/2024 | Stanton et al. | |
| 2011/0184558 A1 | 7/2011 | Jacob et al. | |
| 2012/0029529 A1 | 2/2012 | Jun et al. | |
| 2012/0209069 A1 | 8/2012 | Popovic et al. | |
| 2017/0197311 A1* | 7/2017 | Garcia | G01S 17/931 |
| 2017/0296277 A1 | 10/2017 | Hourtash et al. | |
| 2017/0347979 A1 | 12/2017 | Fehre et al. | |
| 2018/0036090 A1 | 2/2018 | Hasegawa et al. | |
| 2018/0141213 A1 | 5/2018 | Tsao et al. | |
| 2019/0105785 A1* | 4/2019 | Meyer | A61B 34/30 |
| 2019/0107454 A1 | 4/2019 | Lin et al. | |
| 2019/0269468 A1 | 9/2019 | Hsu et al. | |
| 2019/0298465 A1 | 10/2019 | Chin et al. | |
| 2020/0298406 A1* | 9/2020 | Griffiths | A61B 34/37 |
| 2020/0367984 A1* | 11/2020 | Peine | B25J 9/1666 |
| 2023/0190396 A1 | 6/2023 | Taheri et al. | |

FOREIGN PATENT DOCUMENTS

| | | |
|---|---|---|
| EP | 3586782 A1 | 1/2020 |
| WO | 2013/181503 A1 | 12/2013 |
| WO | 2019/136039 A1 | 7/2019 |
| WO | 2019/204013 A1 | 10/2019 |
| WO | 2020/190832 A1 | 9/2020 |
| WO | 2021/059100 A1 | 4/2021 |

OTHER PUBLICATIONS

Morvan, Tangui, et al. “Collision detection and untangling for surgical robotic manipulators.” *The International Journal of Medical Robotics and Computer Assisted Surgery* 5.3 (2009): 233-242.

Extended European Search Report and Written Opinion dated Oct. 2, 2024, for application No. 21874671.7, 12 pages.

Extended European Search Report and Written Opinion dated Sep. 25, 2024, for application No. 21874672.5, 12 pages.

International Search Report and Written Opinion dated Dec. 17, 2021, for International Application No. PCT/IB2021/058548, 20 pages.

International Search Report and Written Opinion dated Dec. 20, 2021, for International Application No. PCT/IB2021/058550, 20 pages.

Chinese First Office Action and Search Report dated Feb. 2, 2026, for Application No. 202180067231.2, 17 pages.

Chinese First Office Action and Search Report dated Feb. 26, 2026, for Application No. 202180067229.5, 18 pages.

Hu, Jiabing, et al. “Probability analysis for grasp planning facing the field of medical robotics.” *Measurement* 141 (2019): 227-234.

Japanese First Office Action dated Feb. 25, 2025, for Application No. 2023-519667, 4 pages.

Japanese First Office Action dated Feb. 18, 2025, for Application No. 2023-519668, 6 pages.

Japanese Final Office Action dated Jul. 15, 2025, for Application No. 2023-519668, 2 pages.

* cited by examiner

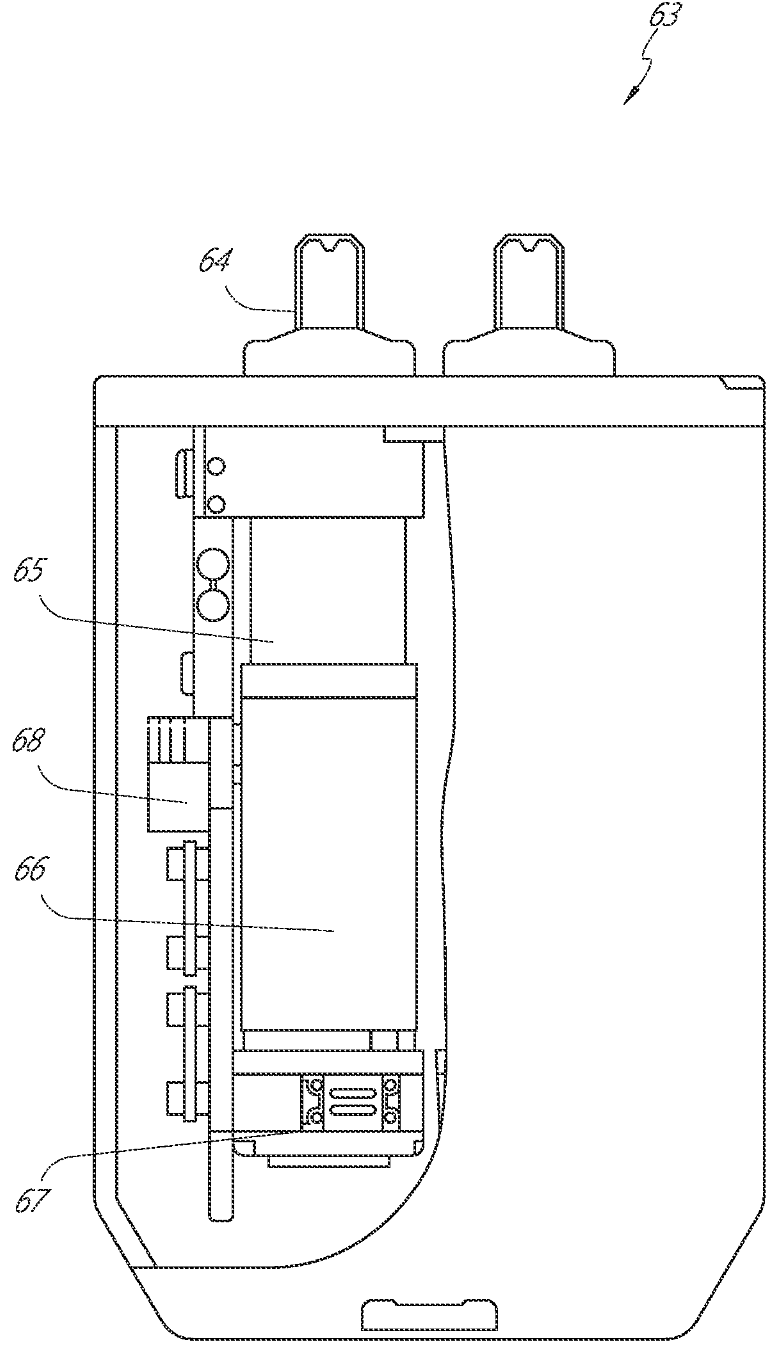
FIG. 15

205
203
221
213
211
215
207
217
209

205
207
217
209
219
221
233

331 Receive one or more parameters of contact with a first kinematic chain detected by one or more sensors 332 The one or more parameters of the contact include one or more of: force information of the contact, location information of the contact, and direction information of the contact 333 Determine a constraint associated with the first kinematic chain based on the one or more parameters of contact with the first kinematic chain 334 The constraint is modeled as a potential field based at least in part on the one or more parameters of contact detected by the one or more sensors 335 The potential field is also based on a probability of detecting a contact by a respective sensor of the one or more sensors 336 Cause adjustment of a configuration of the first kinematic chain from a first configuration to a second configuration based on the constraint 337 Adjustment of the configuration of the first kinematic chain includes changing a position of an adjustable arm support 338 Utilize a null space of the first kinematic chain while causing adjustment of the configuration of the first kinematic chain from the first configuration to the second configuration 339 Cause adjustment of configurations of one or more kinematic chains not in contact with one or more portions of the first kinematic chain based on the constraint determined from the one or more parameters of contact with the first kinematic chain detected by the one or more sensors

FIG. 30

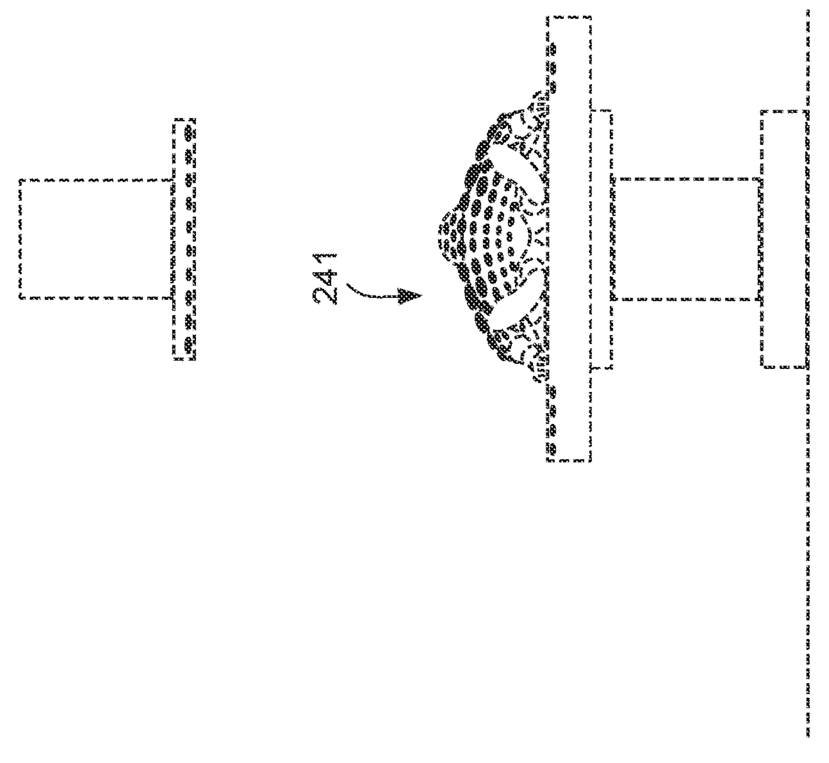
FIG. 35A
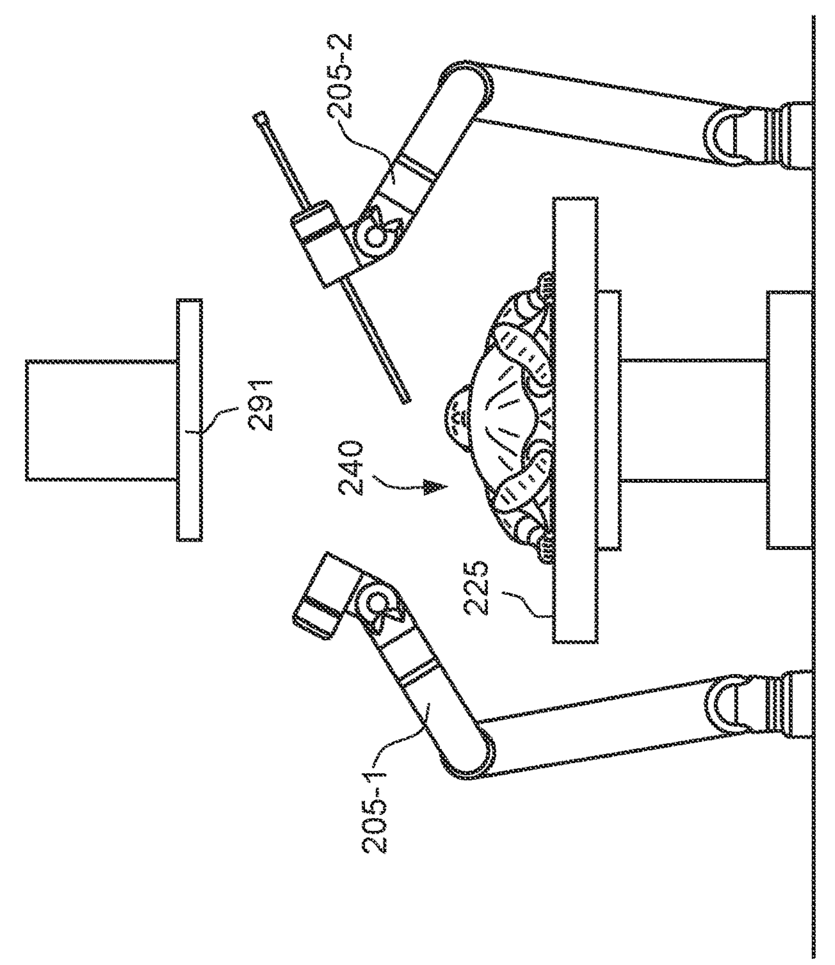

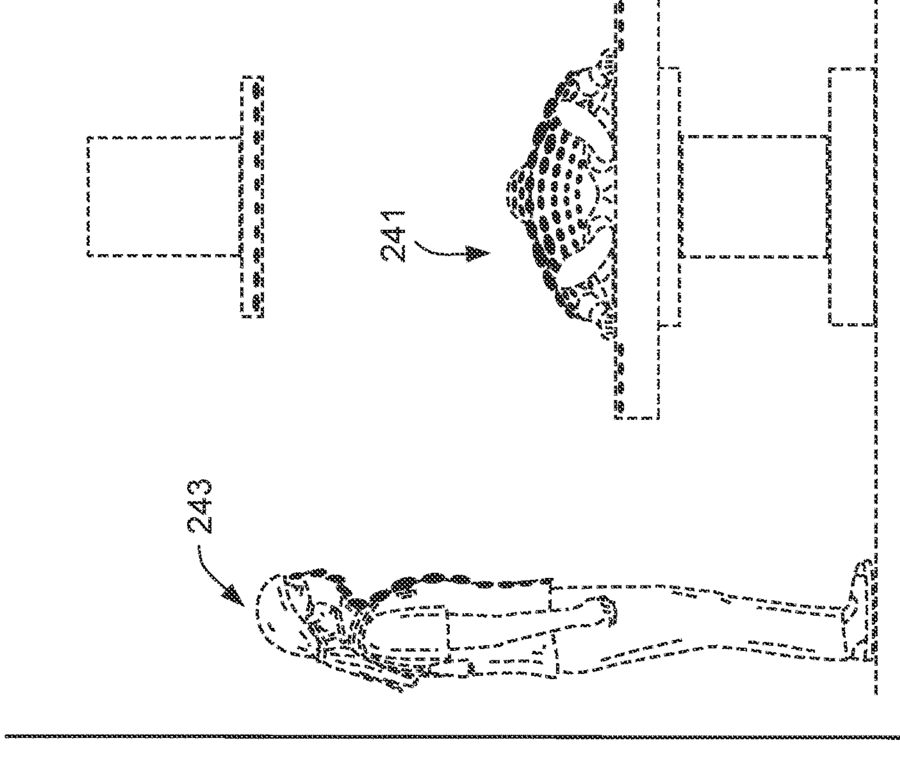
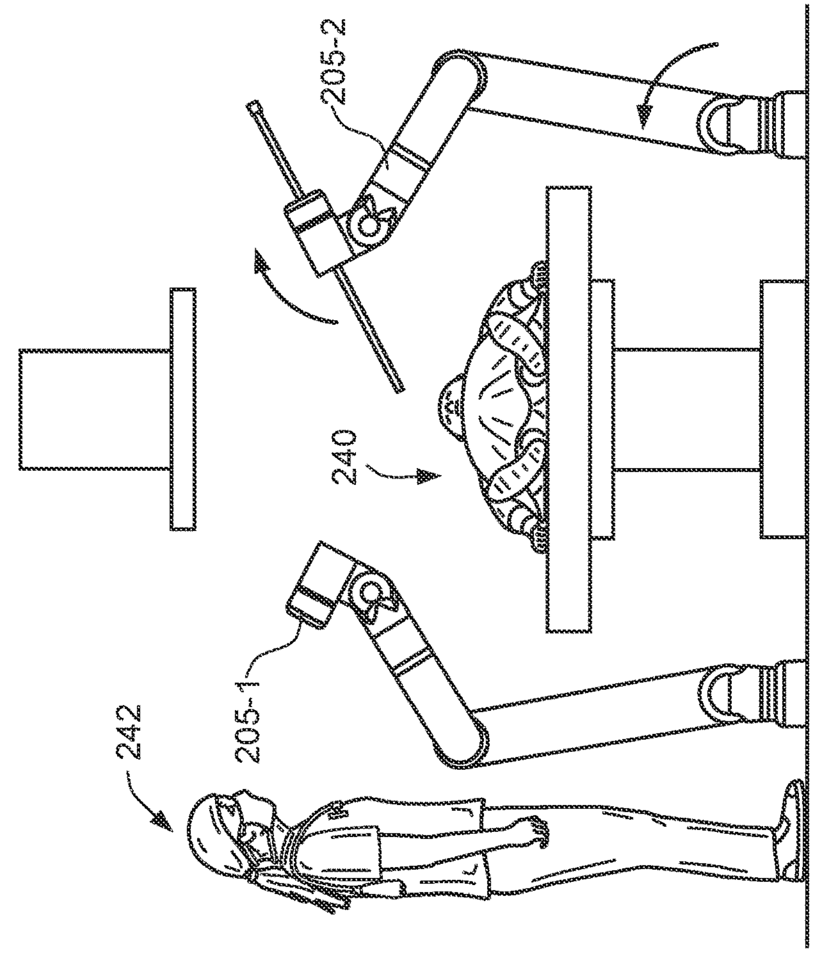
FIG. 35B

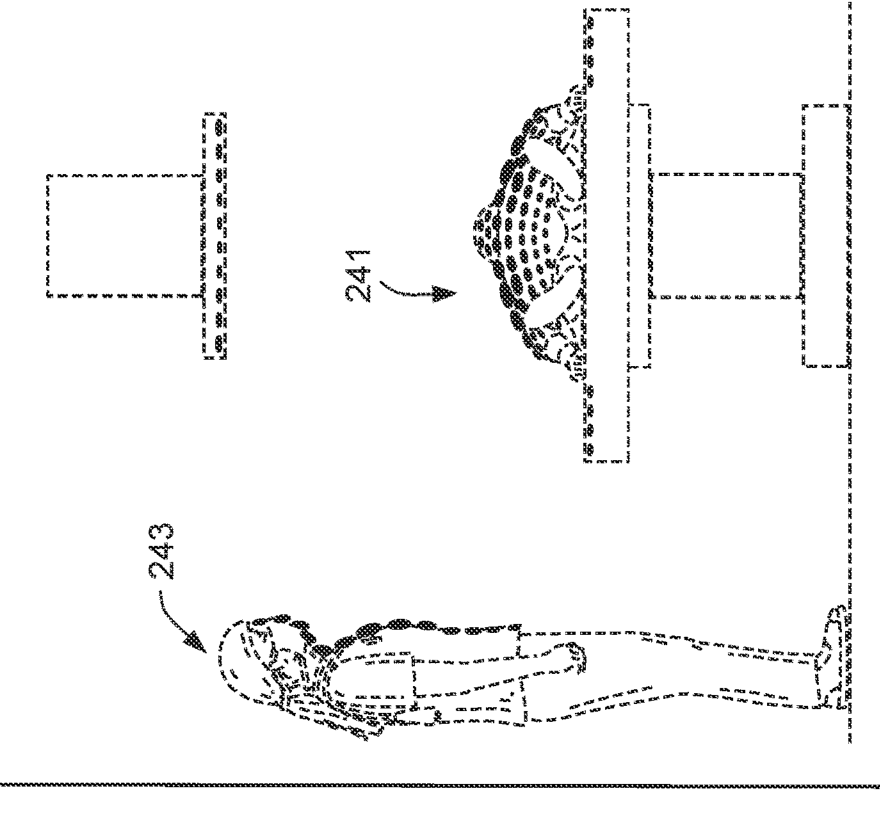
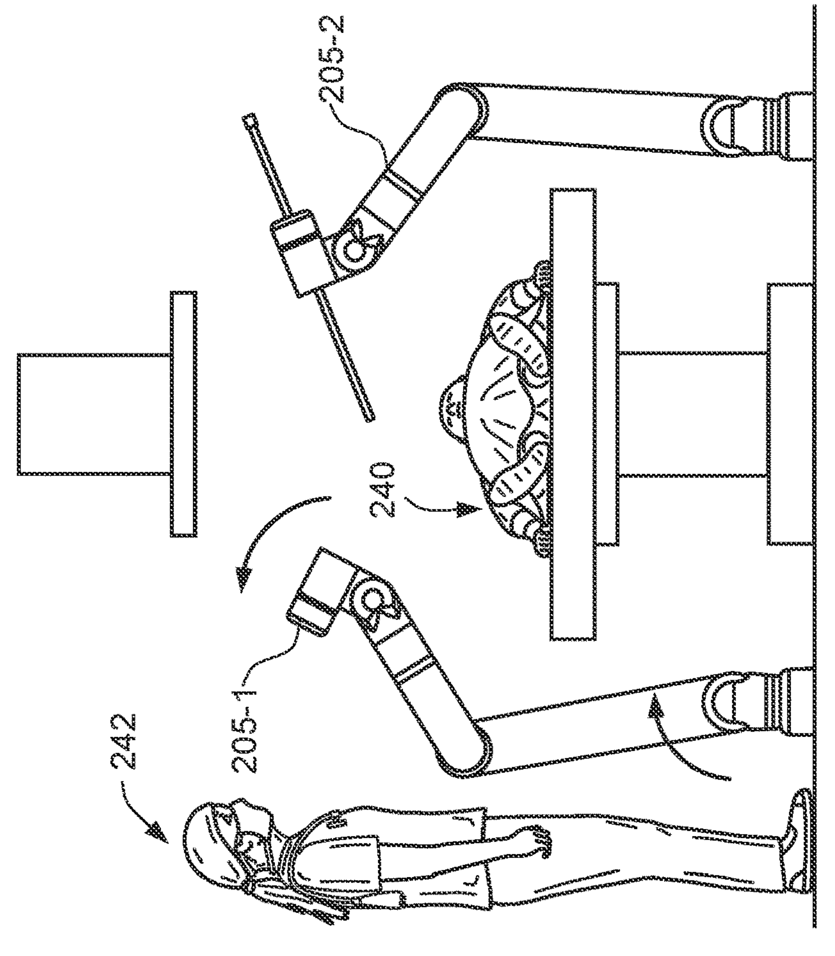
FIG. 35C

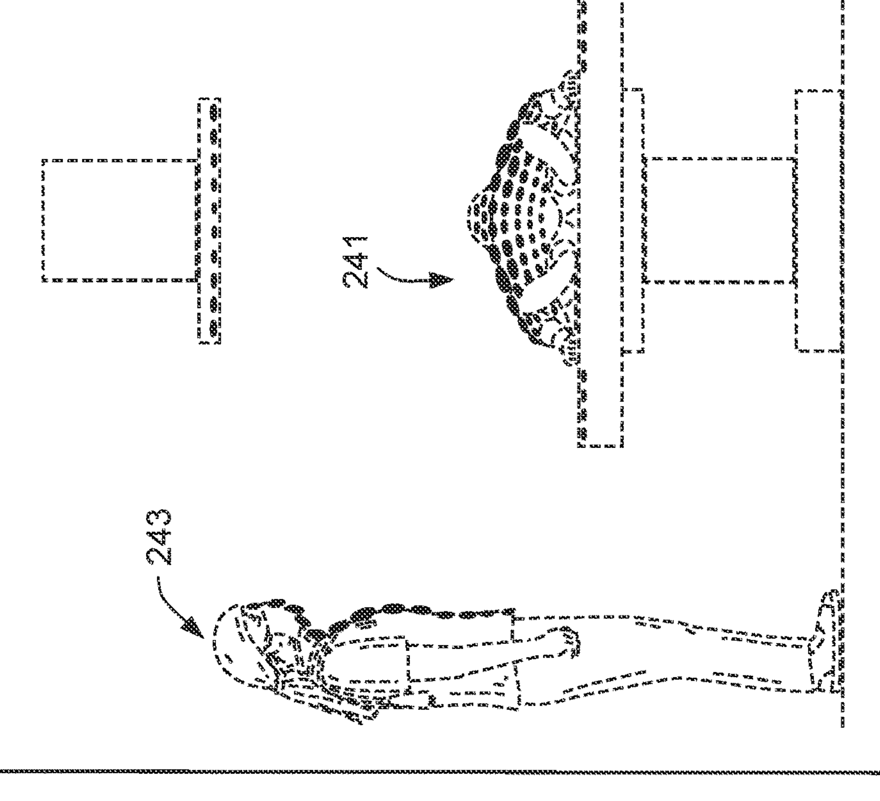
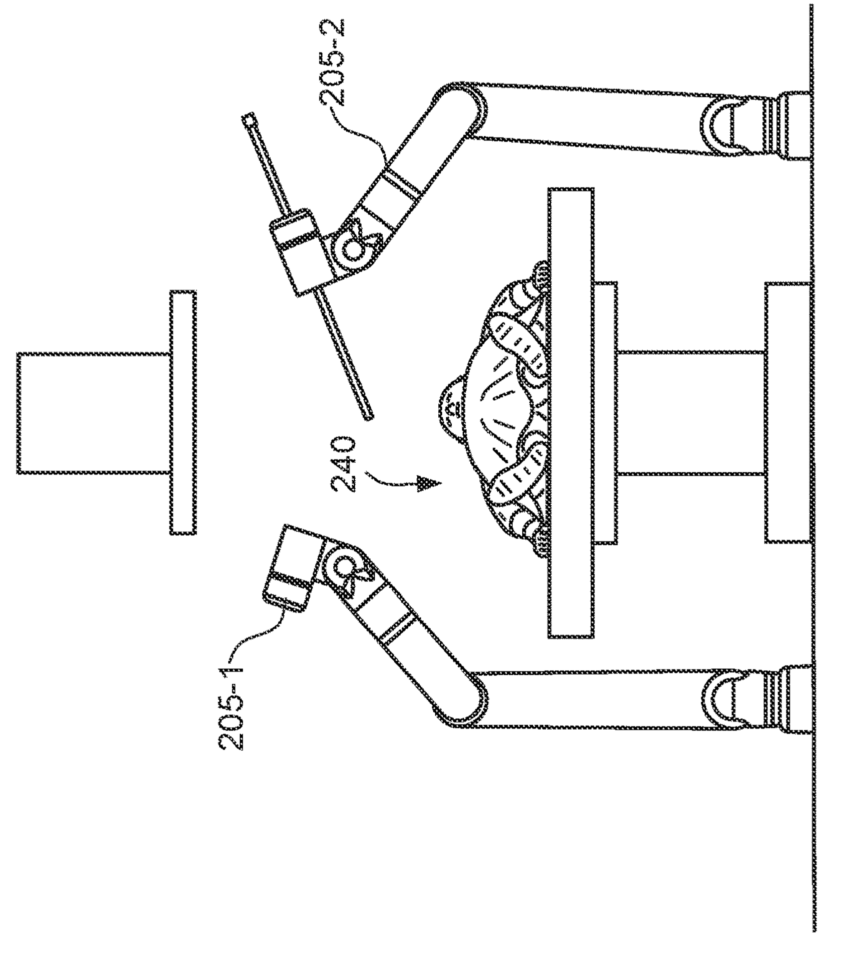
FIG. 35D

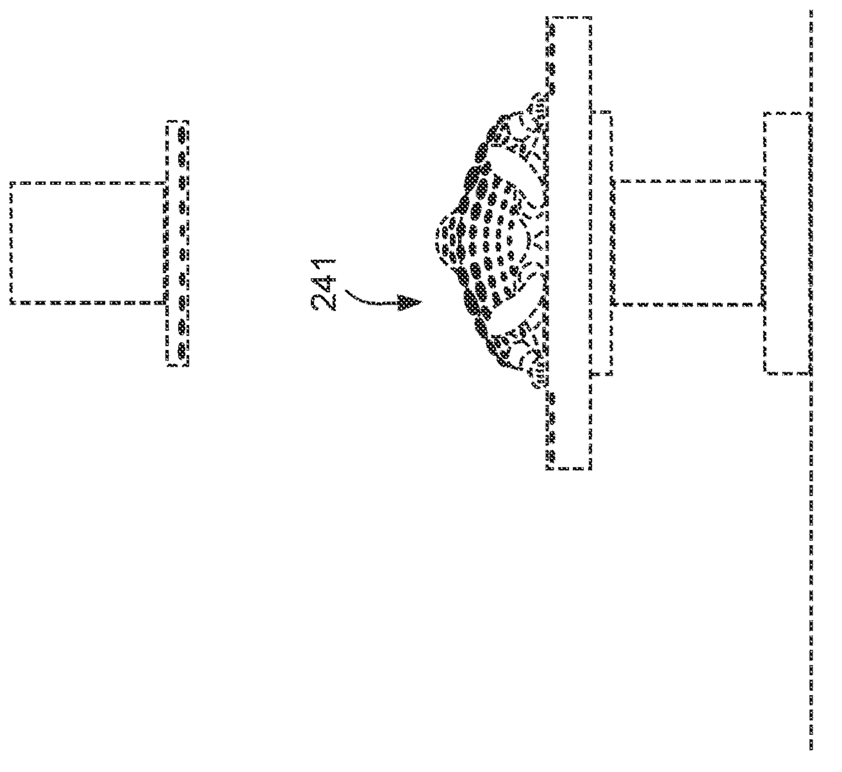
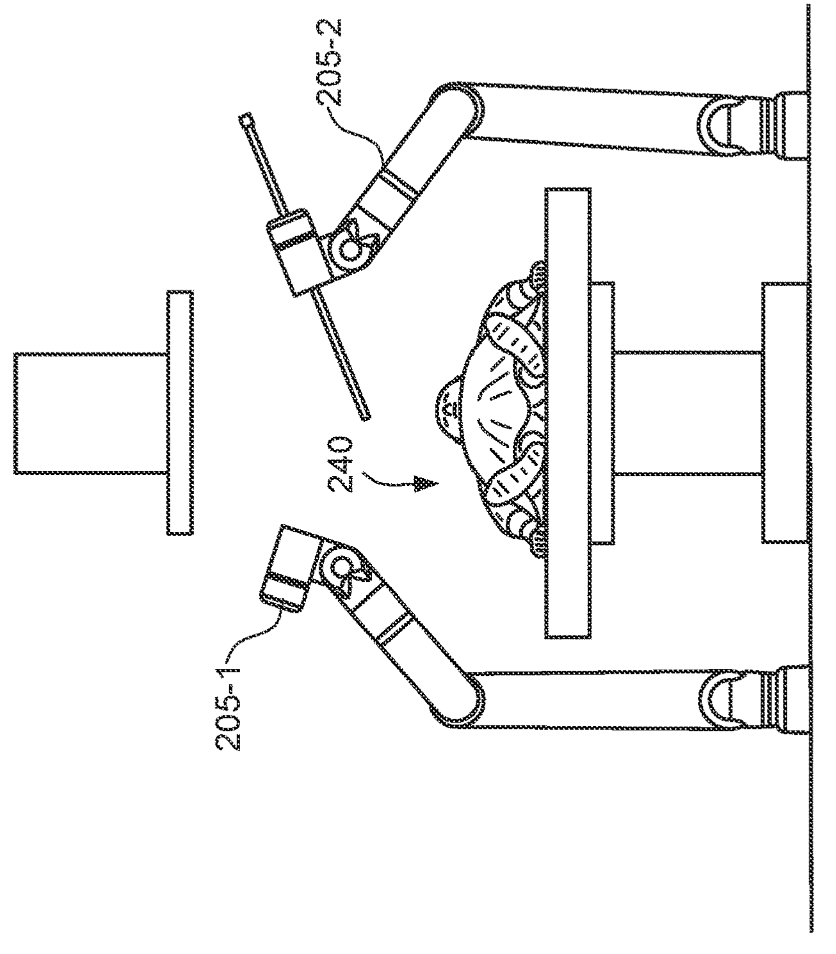
FIG. 35E

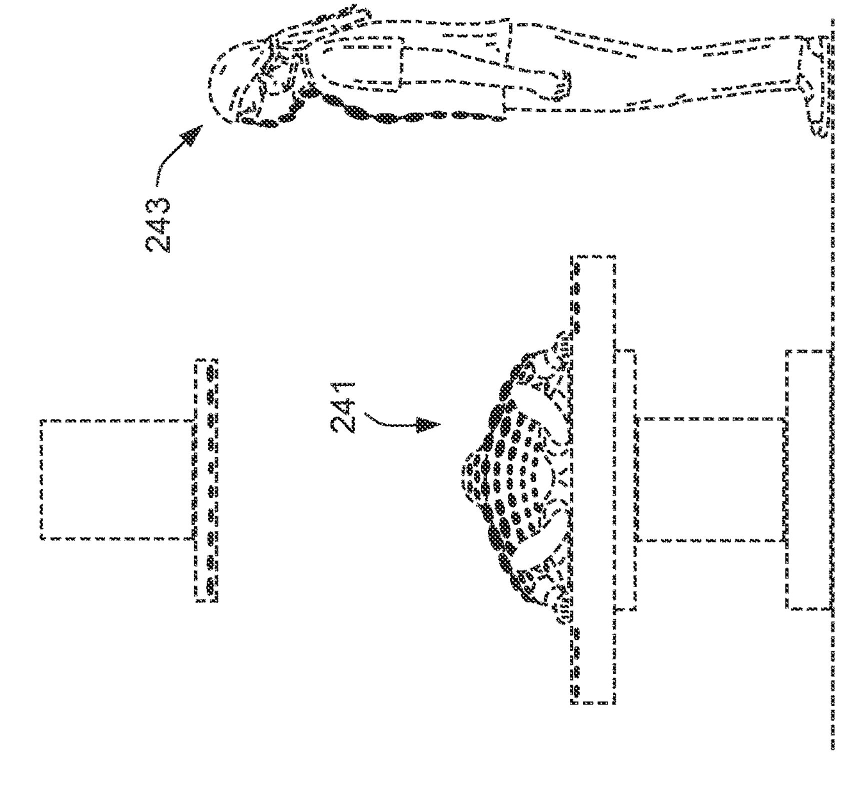
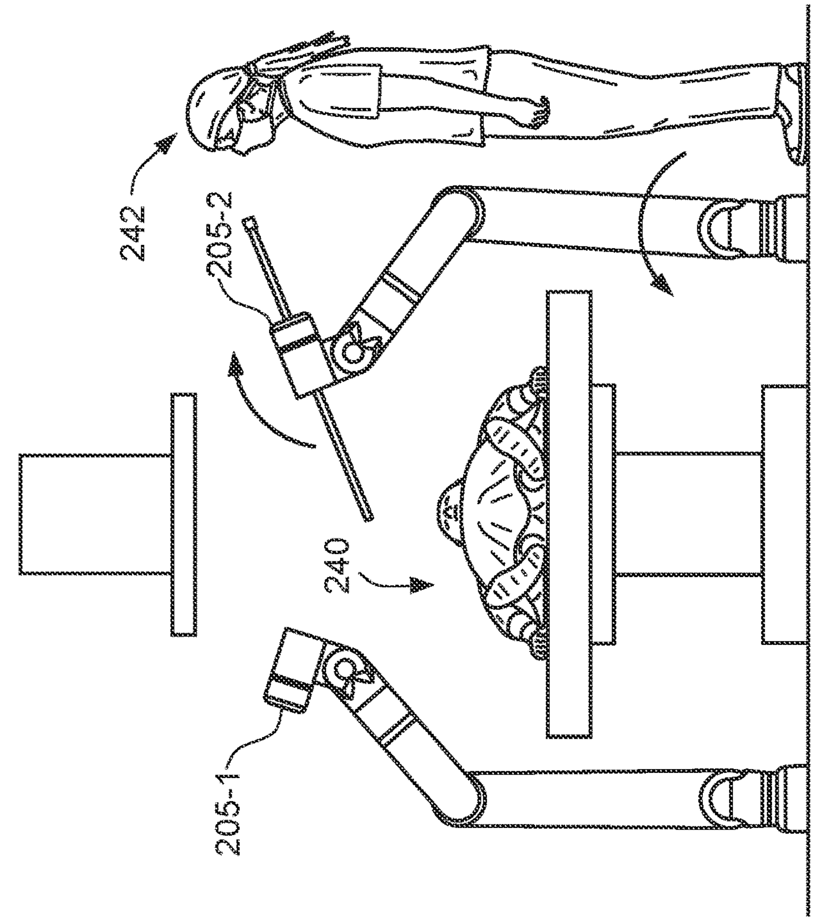
FIG. 35F

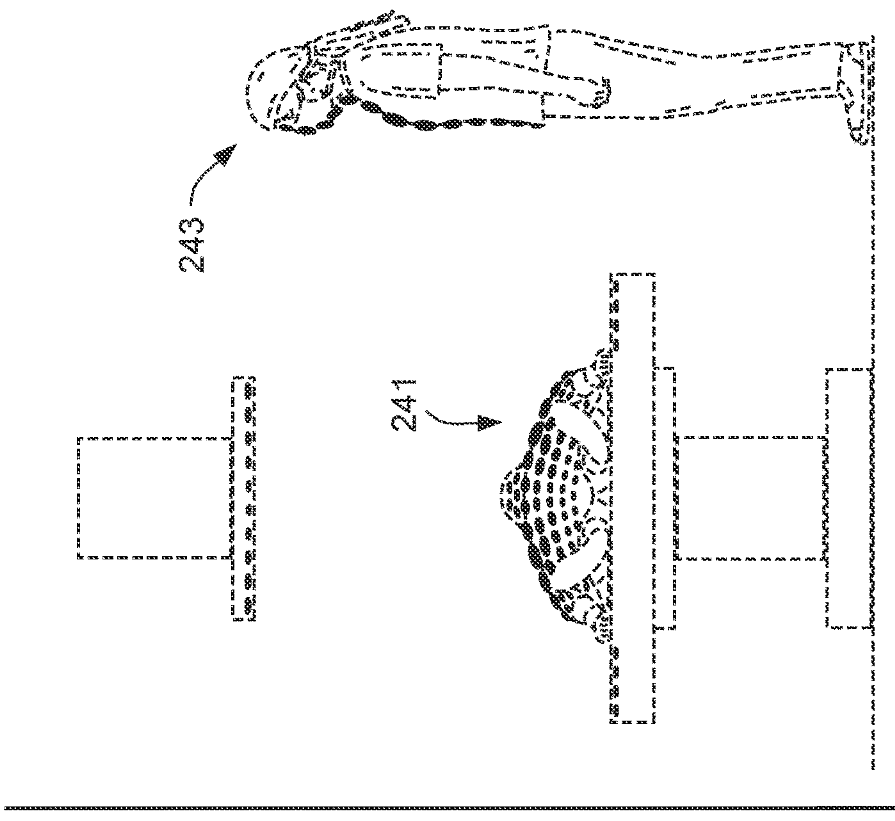
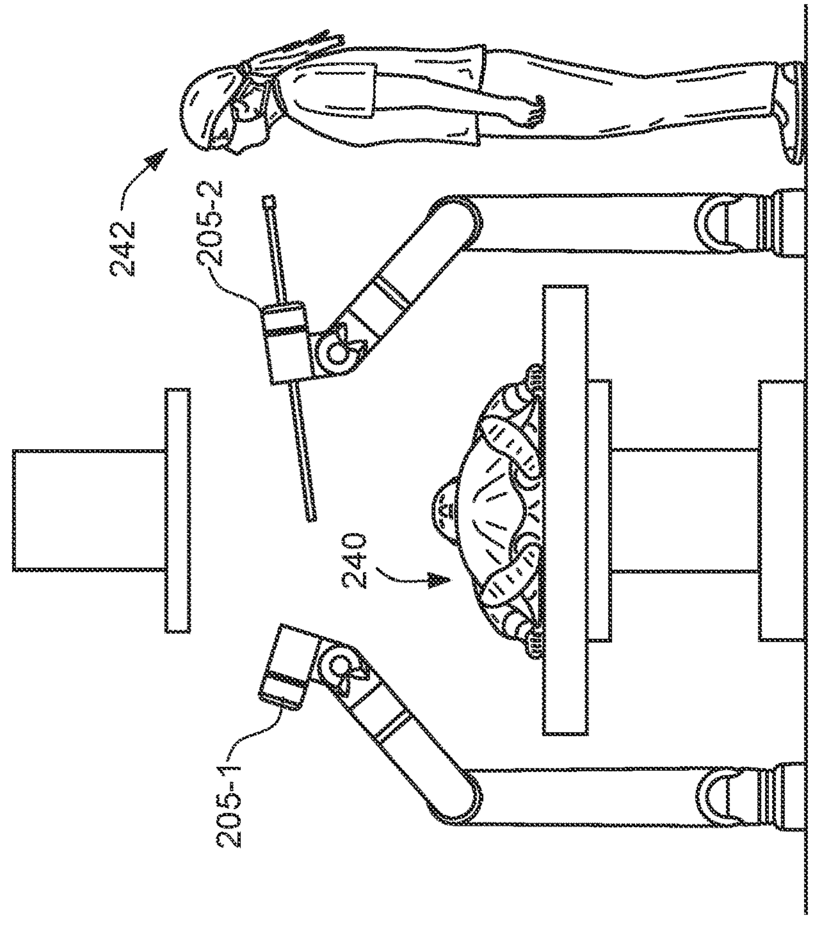
FIG. 35G

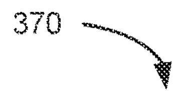

371 Receive, from one or more sensors, first sensor information corresponding to one or more positional locations of one or more objects that are within a vicinity of a first robotic arm 372 Generate or update an object map based on the sensor information. The object map characterizes spatial relationships of objects within a vicinity of the first robotic arm.

373 Adjust a configuration of the first robotic arm from a first configuration to a second configuration based on the object map 374 Iterate: receiving, from the one or more sensors, subsequent sensor information corresponding to positions of one or more objects that are within a vicinity of the first robotic arm; updating the object map based on the subsequent sensor information; and adjusting the configuration of the first robotic arm in accordance with the object map that is updated based on the subsequent sensor information 375 Update the object map based on a probability of detecting a respective object of the one or more objects 376 The one or more objects include an object that moves dynamically. Remove the update to the object map (e.g., removing the object from the object map) after a period of time after the object map has been updated to reflect the object.

377 Update the object map based on a configuration of the medical robotic system

COLLISION AVOIDANCE IN SURGICAL ROBOTICS BASED ON DETECTION OF CONTACT INFORMATION

RELATED APPLICATIONS

This application is a continuation of PCT Patent Application No. PCT/IB2021/058548, filed Sep. 20, 2021, entitled "Collision Avoidance in Surgical Robotics Based on Detection of Contact Information," which claims priority to U.S. Provisional Patent Application No. 63/086,036, filed Sep. 30, 2020, entitled "Collision Avoidance in Surgical Robotics Based on Detection of Contact Information," each of which are incorporated by reference herein in their entireties.

TECHNICAL FIELD

The systems and methods disclosed herein are directed to medical robotic systems with robotic arms, and more particularly to medical robotic systems that can automatically adjust robotic arms to avoid collision.

BACKGROUND

During a medical procedure using a medical robotic system, robotic arms can come into contact with one another (e.g., arm collisions) and with the environment (e.g., patient, bed-side staff, and accessories). Although collisions between robotic arms may be predicted and avoided based on known arm configurations, it has been challenging to predict and completely avoid collisions with other objects, especially for objects that change their positions over time. Regardless of the type of collision, collisions can be disruptive to medical procedures, and thus, there is a need for medical robotic systems that can reduce or eliminate the occurrence of collisions with robotic arms.

SUMMARY

Disclosed herein is a medical robotic system using one or more sensors on a kinematic component (e.g., a robotic arm) to detect a force (e.g., or other parameters of a collision). The detected force or other parameters of the collision are used to adjust a configuration (e.g., a position) of the kinematic component, which, in turn, reduces future occurrence of collisions with the kinematic component.

In accordance with some embodiments, a medical robotic system includes a first kinematic chain; one or more sensors positioned to detect one or more parameters of contact with one or more portions of the first kinematic chain; one or more processors in communication with the one or more sensors; and memory storing instructions, which, when executed by the one or more processors, cause adjustment of a configuration of the first kinematic chain from a first configuration to a second configuration based on a constraint determined from the one or more parameters of contact with the first kinematic chain detected by the one or more sensors.

In accordance with some embodiments, a method is performed by an electronic device in communication with a medical robotic system. The medical robotic system includes a first kinematic chain and one or more sensors positioned to detect one or more parameters of contact with the first kinematic chain. The method includes receiving one or more parameters of contact with the first kinematic chain detected by the one or more sensors; determining a constraint associated with the first kinematic chain based on the one or more parameters of contact with the first kinematic chain; and causing adjustment of a configuration of the first kinematic chain from a first configuration to a second configuration based on the constraint.

In accordance with some embodiments, an electronic device includes one or more processors, and memory storing instructions, which, when executed by the one or more processors, cause the one or more processors to receive one or more parameters of contact, detected by the one or more sensors, with a first kinematic chain of a medical robotic system; determine a constraint associated with the first kinematic chain based on the one or more parameters of contact with the first kinematic chain; and cause adjustment of a configuration of the first kinematic chain from a first configuration to a second configuration based on the constraint.

In accordance with some embodiments, a computer readable storage medium stores instructions for execution by one or more processors of an electronic device. The stored instructions include instructions for receiving one or more parameters of contact, detected by the one or more sensors, with a first kinematic chain of a medical robotic system; determining a constraint associated with the first kinematic chain based on the one or more parameters of contact with the first kinematic chain; and causing adjustment of a configuration of the first kinematic chain from a first configuration to a second configuration based on the constraint.

In accordance with some embodiments, a medical robotic system includes a first robotic arm; one or more sensors positioned to detect presence of objects adjacent to the first robotic arm; one or more processors in communication with the one or more sensors; and memory. The memory stores instructions, which, when executed by the one or more processors, cause the one or more processors to: receive, from the one or more sensors, first sensor information corresponding to one or more positional locations of one or more objects that are within a vicinity of the first robotic arm; generate or update an object map based on the first sensor information, wherein the object map characterizes spatial relationships of objects adjacent to the first robotic arm; and adjust a configuration of the first robotic arm from a first configuration to a second configuration based on the object map.

In accordance with some embodiments, a medical robotic system includes a first robotic arm; one or more sensors positioned to detect presence of a dynamic object within a vicinity of the first robotic arm; one or more processors in communication with the one or more sensors; and memory. The memory stores instructions, which, when executed by the one or more processors, cause the one or more processors to: receive, from the one or more sensors, sensor information corresponding to a position of the dynamic object that is within a vicinity of the first robotic arm; generate or update an object map based on the sensor information, wherein the object map characterizes spatial relationships of objects within a vicinity of the first robotic arm; and adjust configuration of the first robotic arm from a first configuration to a second configuration based on the object map.

In accordance with some embodiments, a method is performed by an electronic device in communication with a medical robotic system including a first robotic arm and one or more sensors positioned to detect presence of objects within a vicinity of the first robotic arm. The method includes receiving, from the one or more sensors, sensor information corresponding to positions of one or more objects that are present within a vicinity of the first robotic arm; generating or updating an object map based on the sensor information, wherein the object map characterizes spatial relationships of objects within a vicinity of the first robotic arm; and adjusting a configuration of the first robotic arm from a first configuration to a second configuration based on the object map.

In accordance with some embodiments, an electronic device includes one or more processors; and memory. The memory stores instructions, which, when executed by the one or more processors, cause the one or more processors to: receive, from one or more sensors, sensor information corresponding to positions of one or more objects that are within a vicinity of a first robotic arm of a medical robotic system; generate or update an object map based on the sensor information, wherein the object map characterizes spatial relationships of objects within a vicinity of the first robotic arm; and cause adjustment of a configuration of the first robotic arm from a first configuration to a second configuration based on the object map.

In accordance with some embodiments, a computer readable storage medium stores instructions for execution by one or more processors of an electronic device. The stored instructions include instructions for: receiving sensor information corresponding to positions of one or more objects that are present adjacently to a first robotic arm of a medical robotic system; generating or updating an object map based on the sensor information, wherein the object map characterizes spatial relationships of objects adjacent to the first robotic arm; and causing adjustment of a configuration of the first robotic arm from a first configuration to a second configuration based on the object map.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 15 illustrates an exemplary instrument driver.

FIG. 30 is a flow diagram illustrating a method of adjusting a configuration of a kinematic chain based on contact information in accordance with some embodiments.

FIGS. 35A-35G illustrate configurations of robotic arms and corresponding maps in accordance with some embodiments.

FIG. 37 is a flow diagram illustrating a method of adjusting a configuration of a robotic arm based on sensor information in accordance with some embodiments.

FIG. 38 is a schematic diagram illustrating electronic components of a medical robotic system in accordance with some embodiments.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
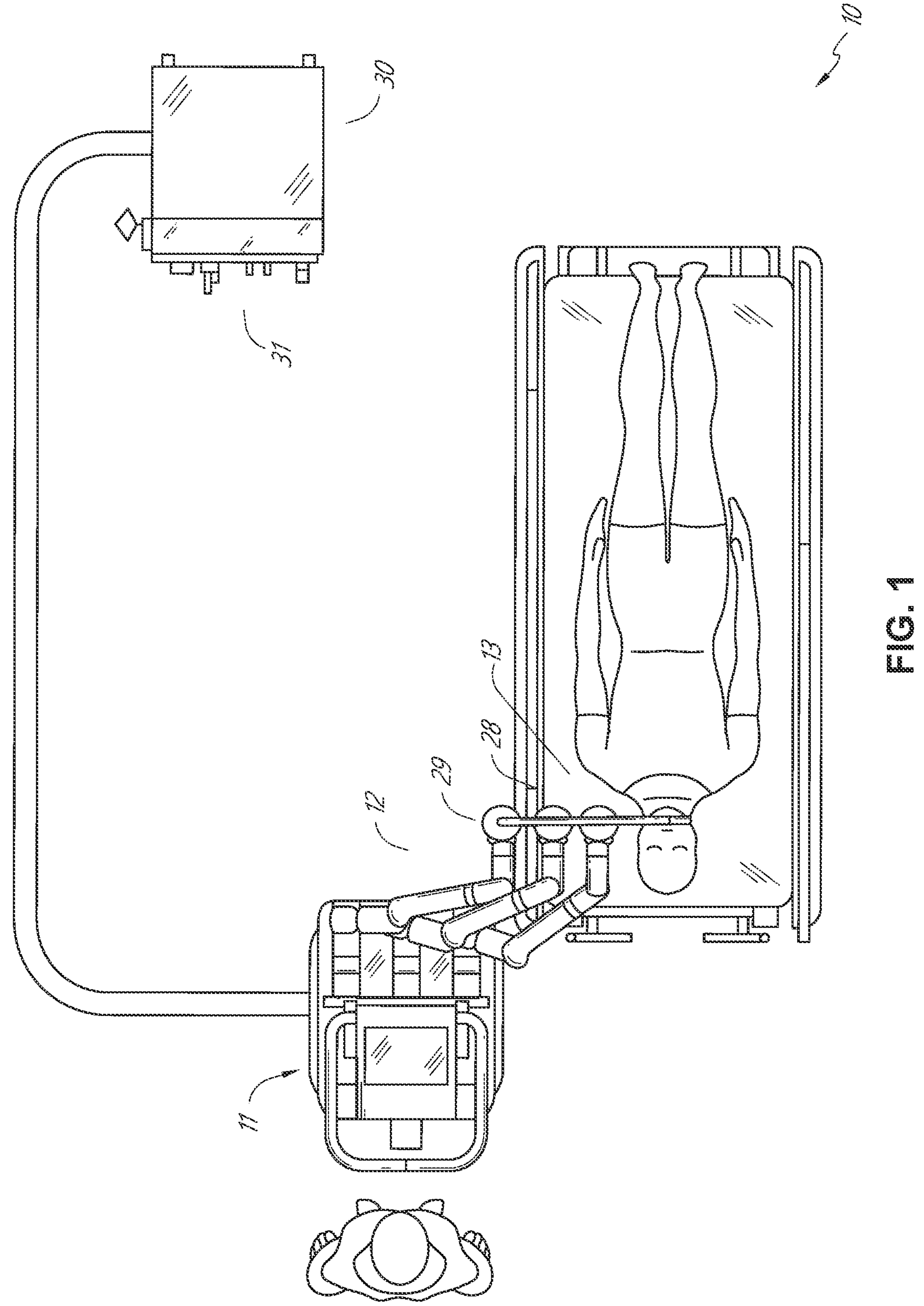
FIG. 1 illustrates an embodiment of a cart-based robotic system arranged for diagnostic and/or therapeutic bronchoscopy procedure(s).
Figure 2:
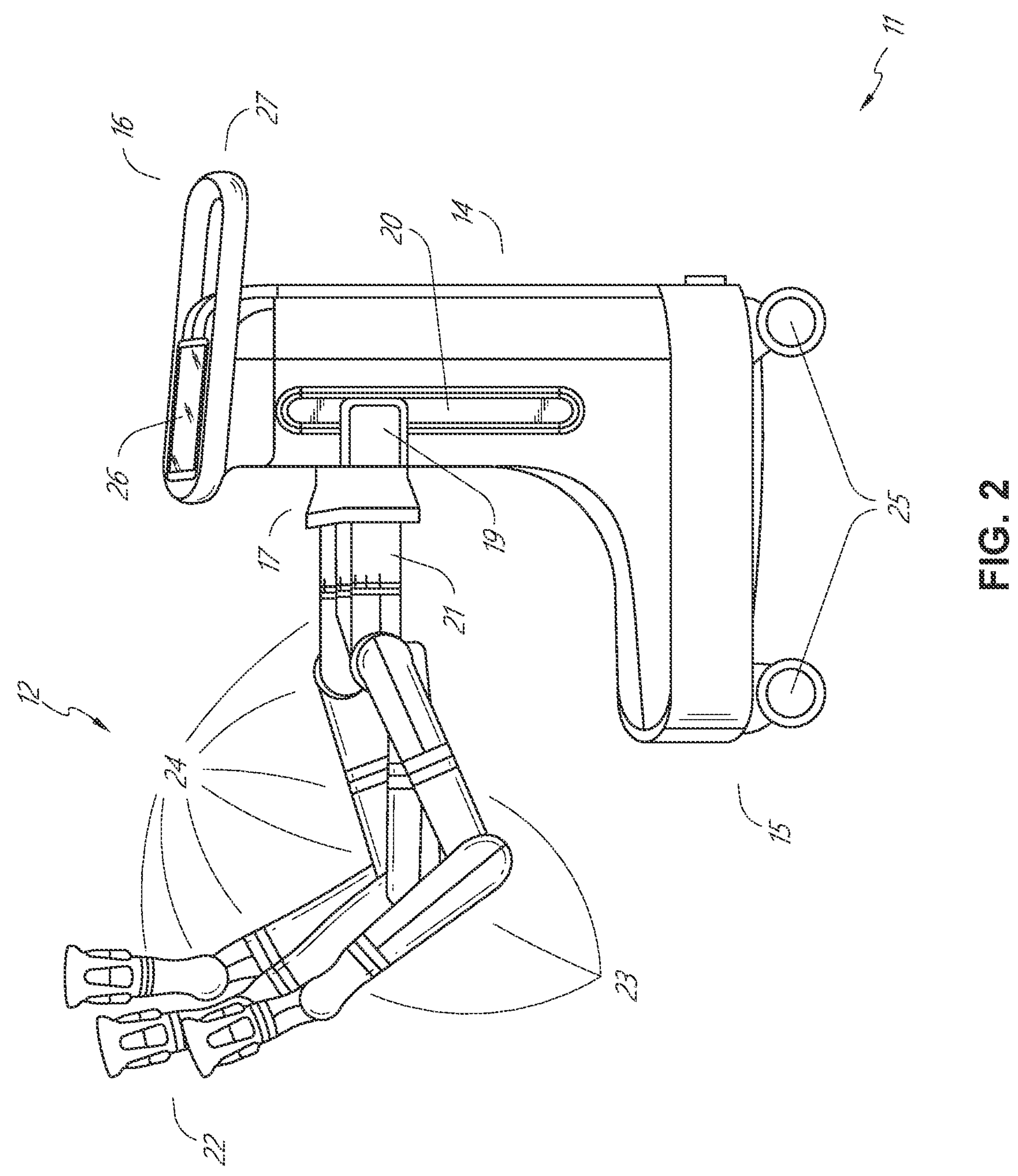
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 31 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
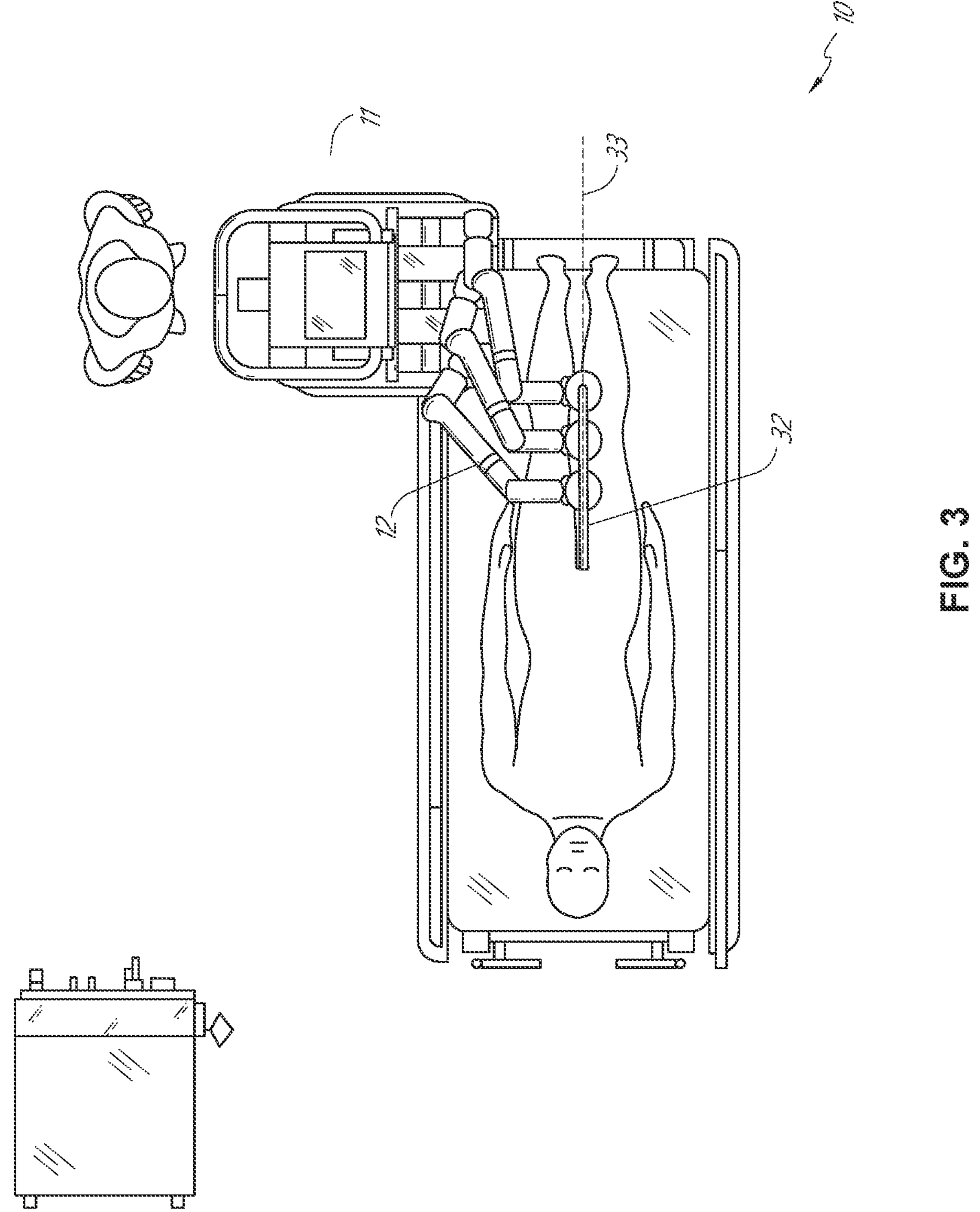
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
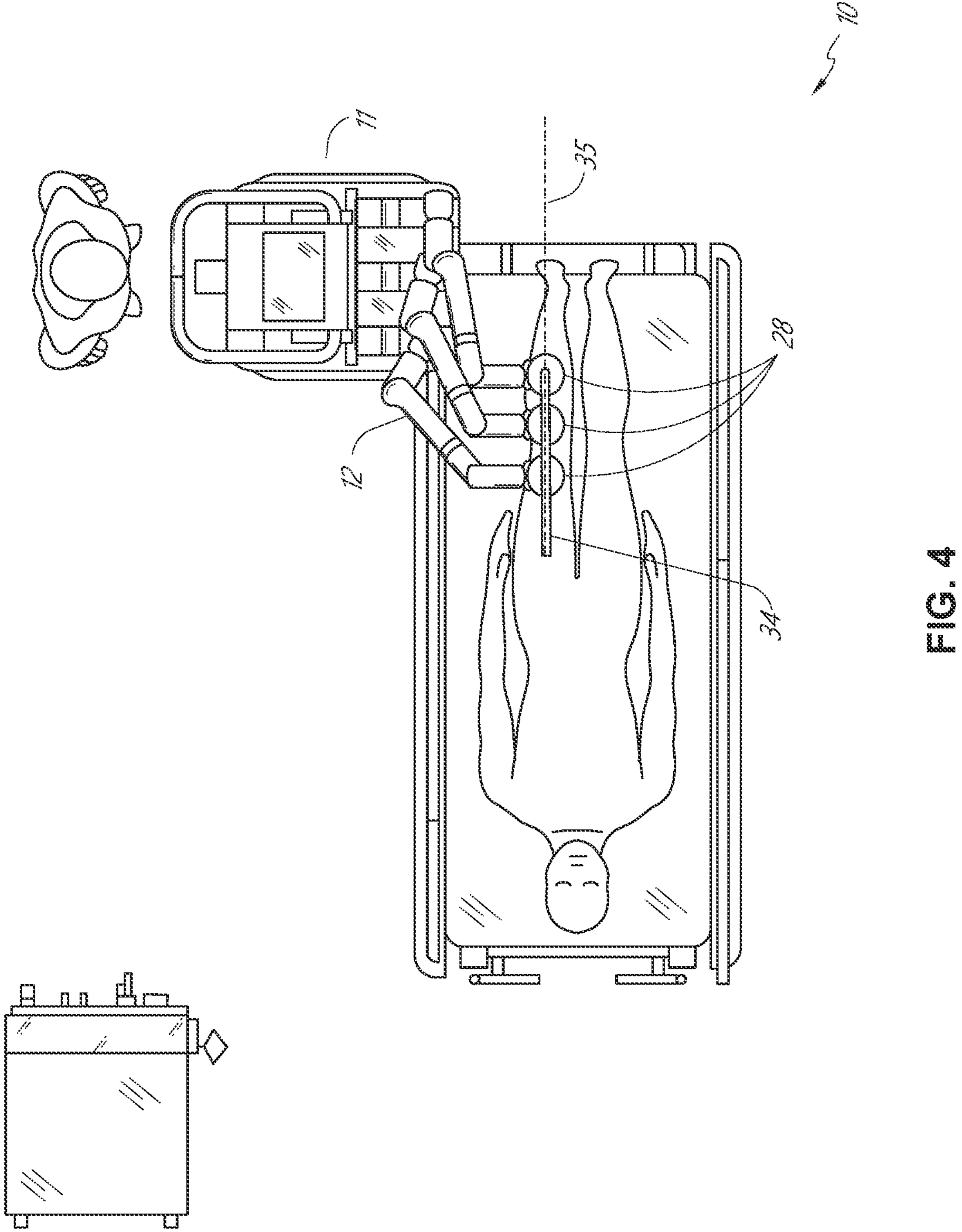
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
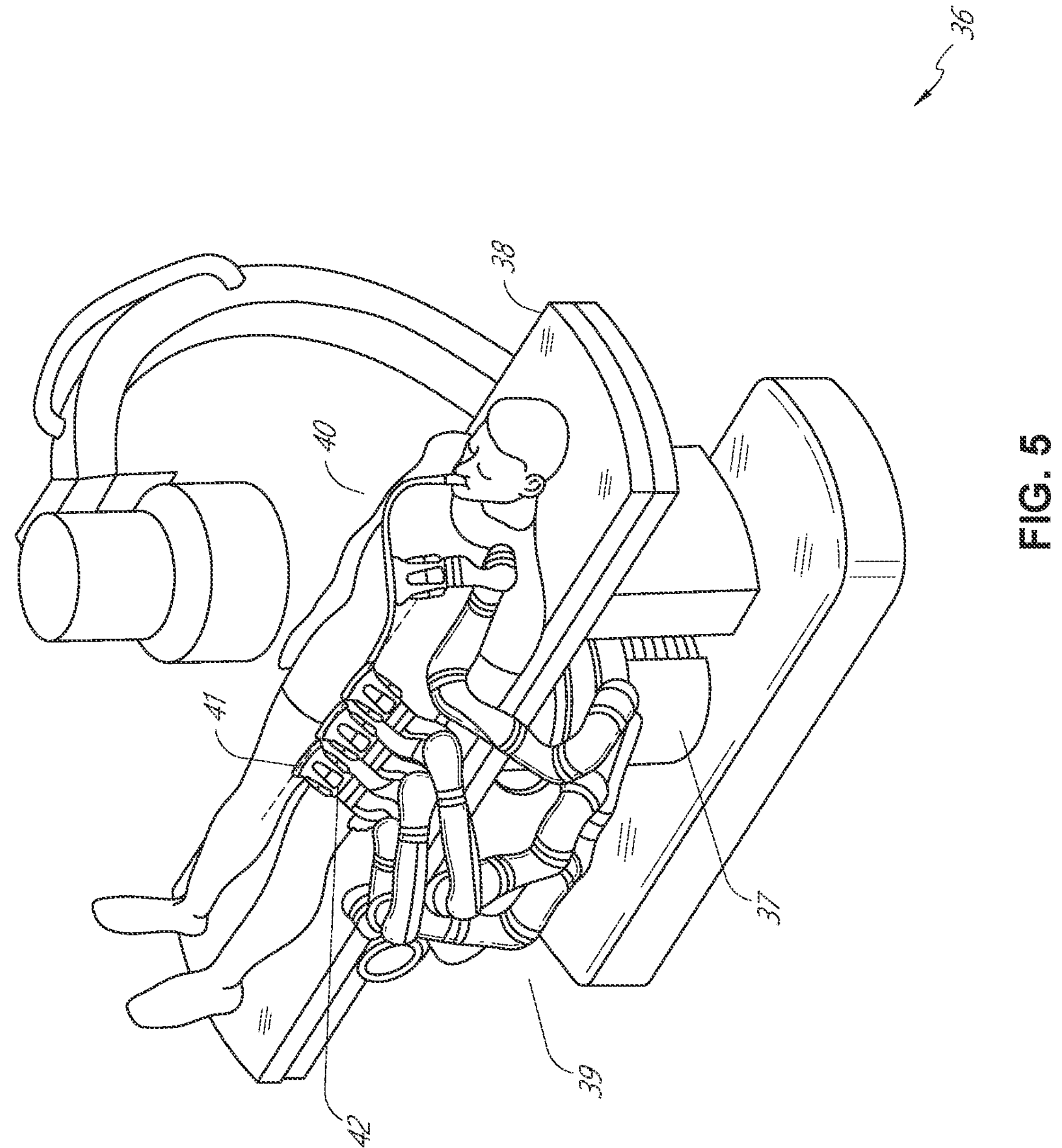
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
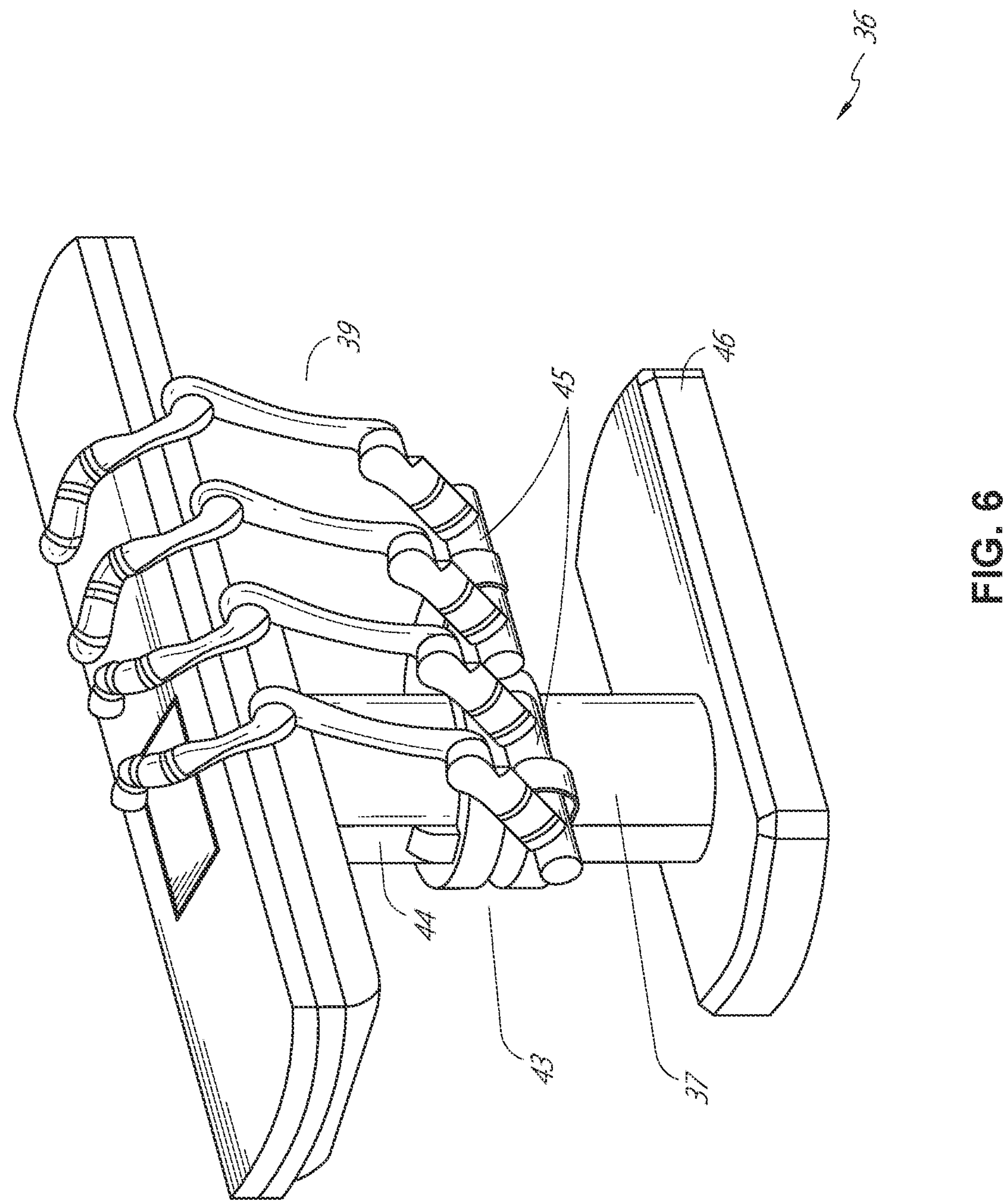
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
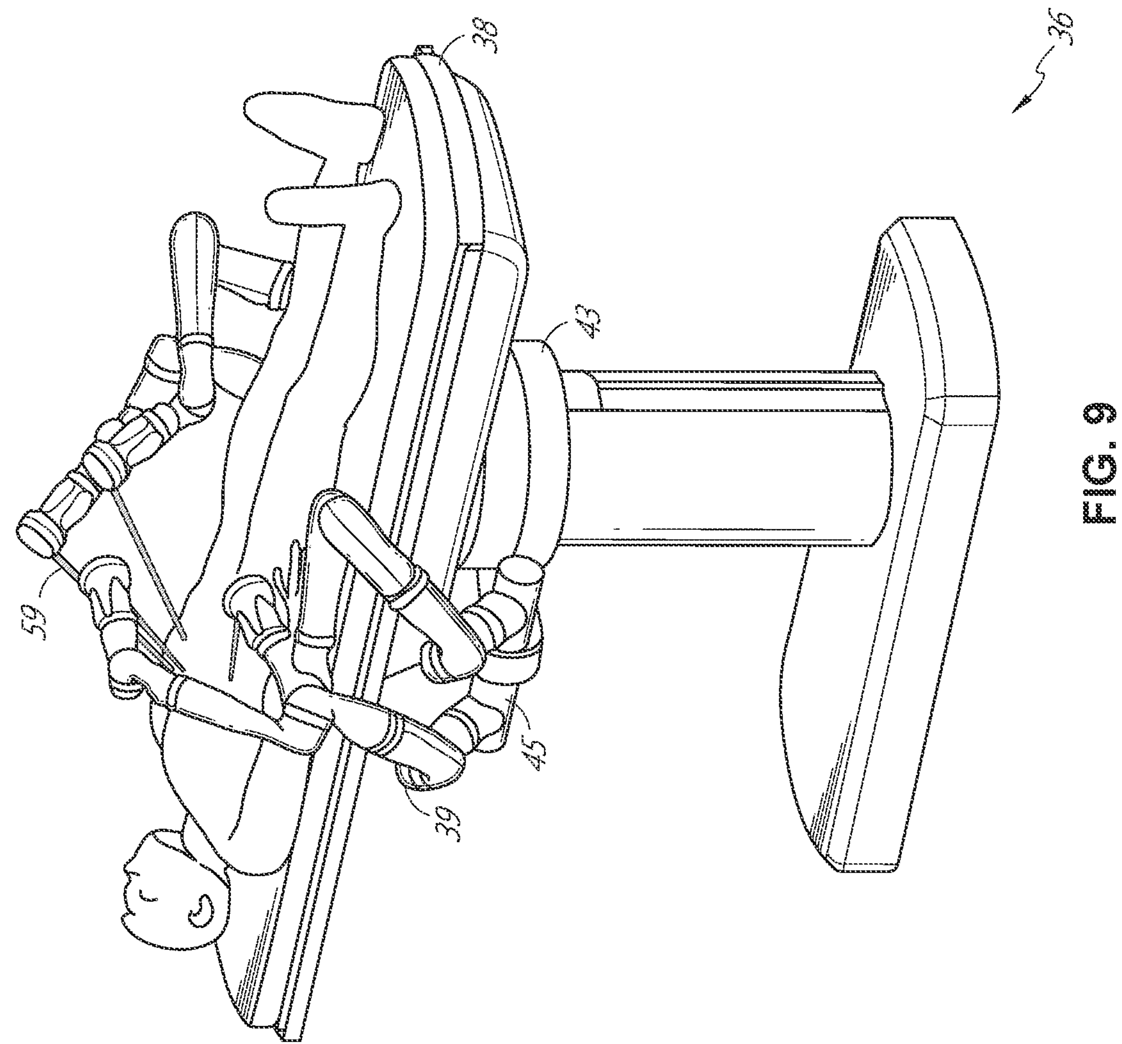
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
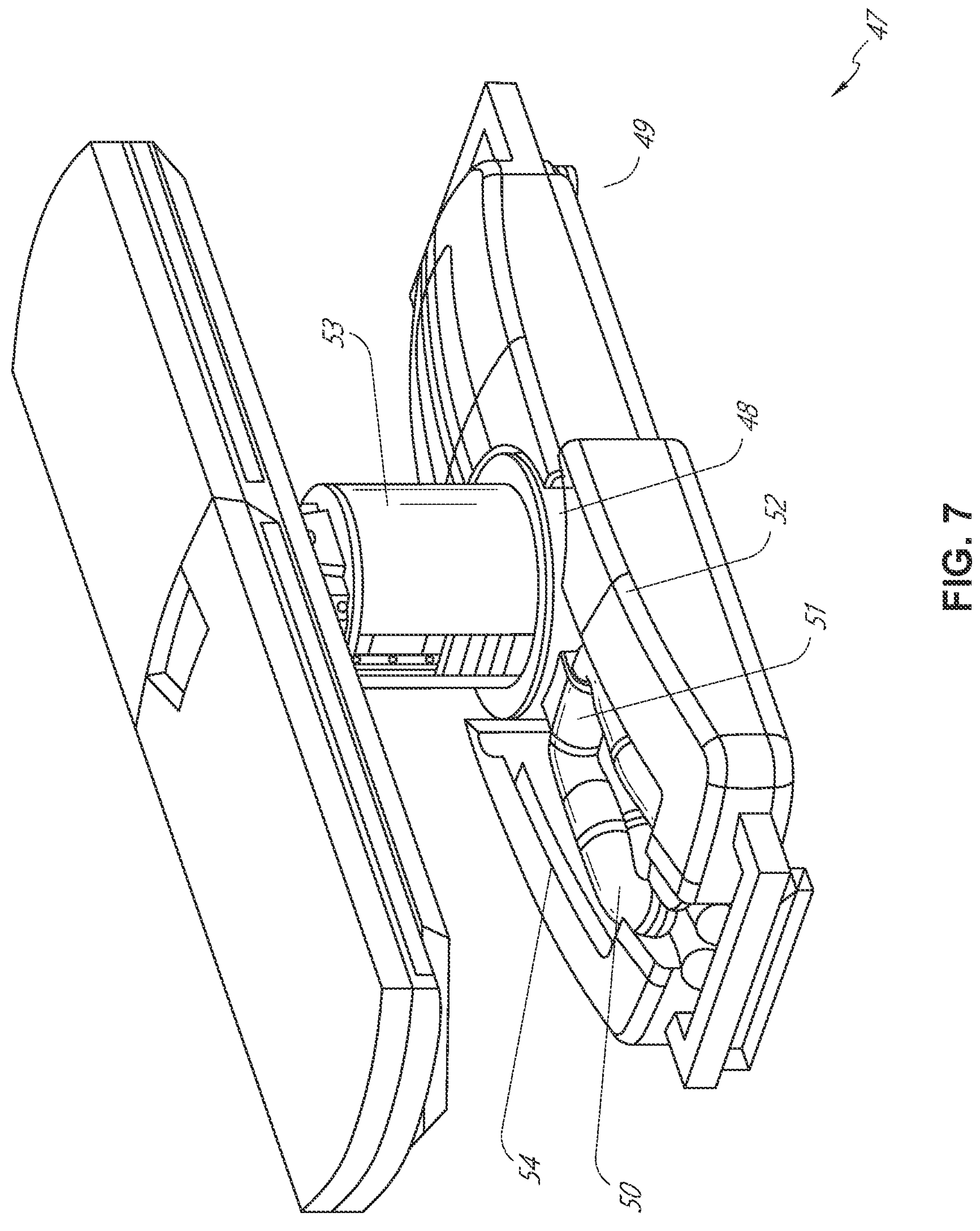
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
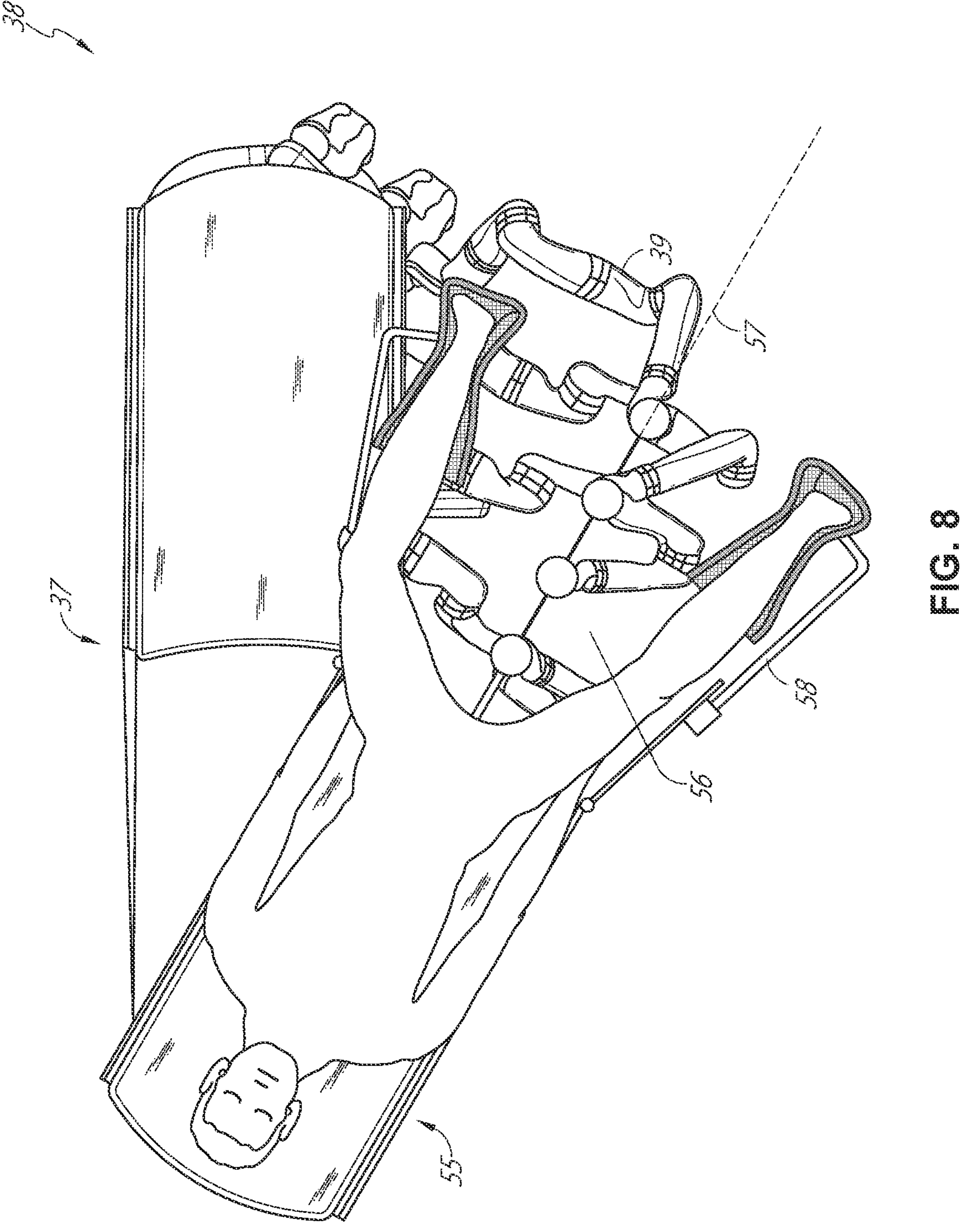
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
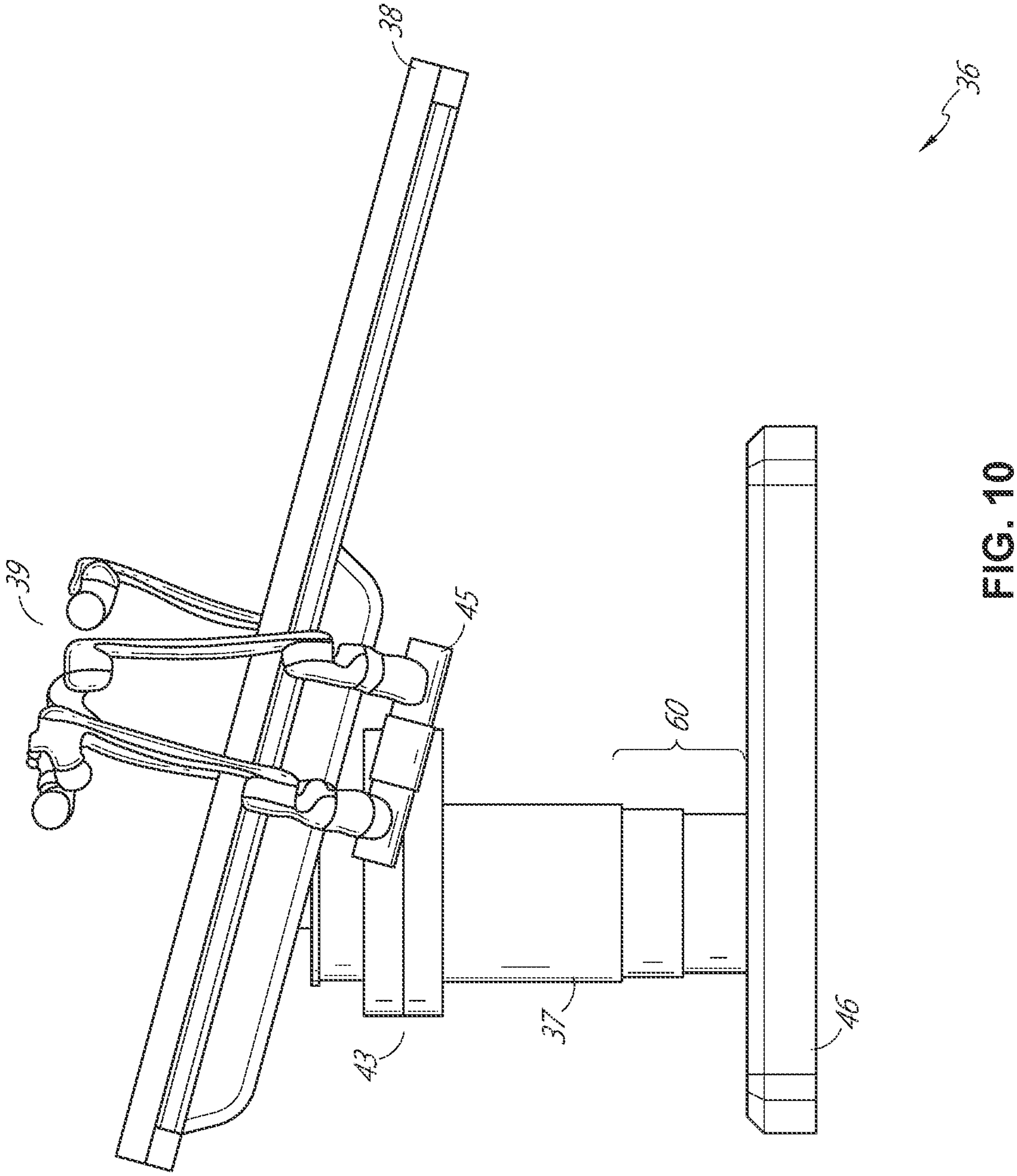
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
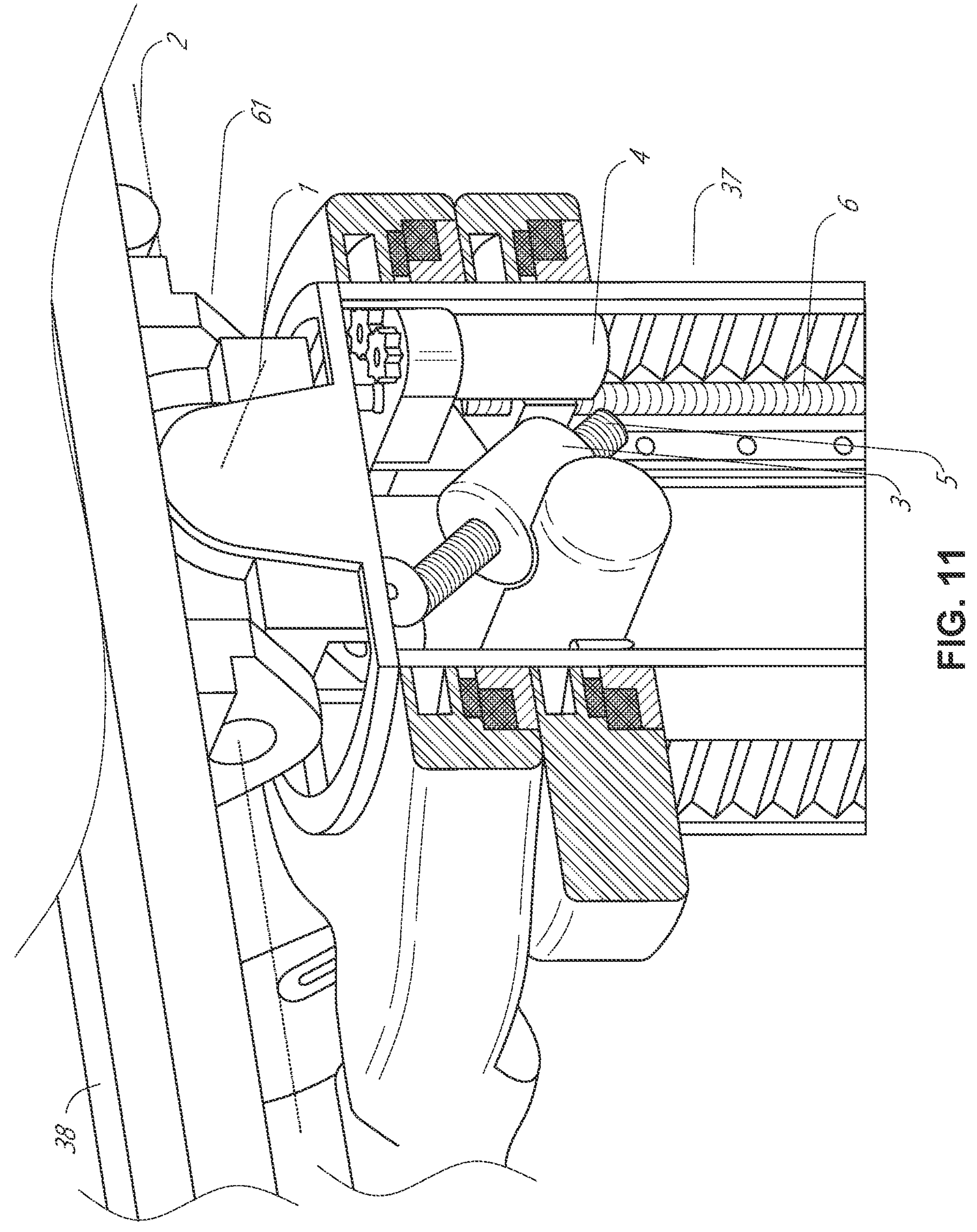
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
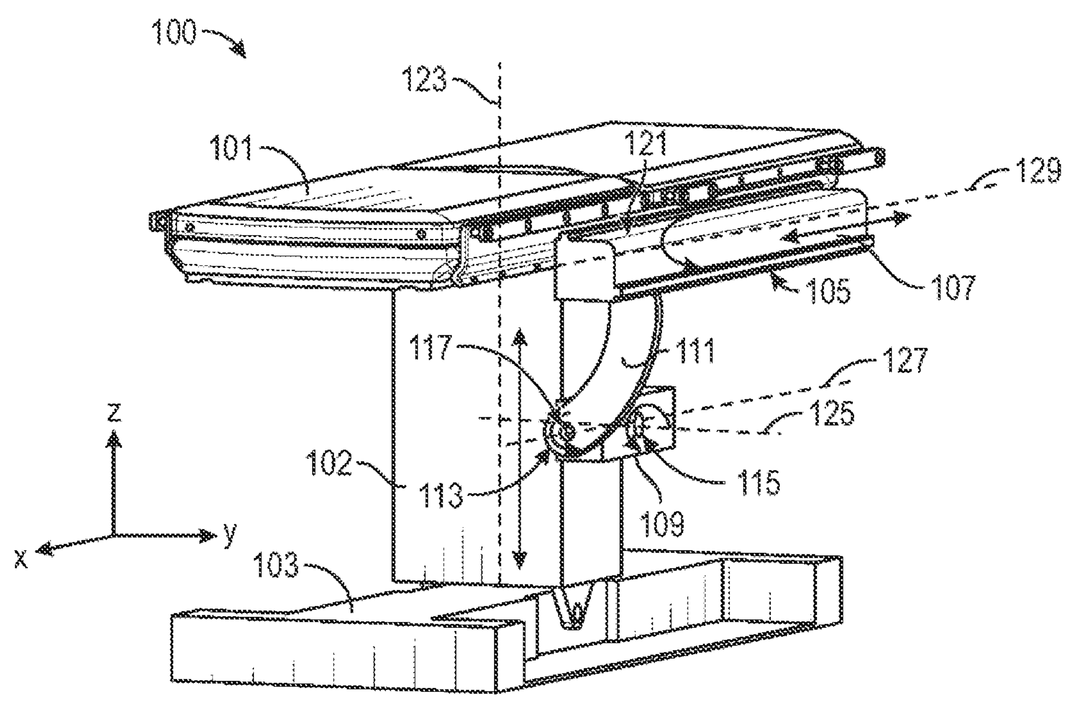
FIG. 12 illustrates an alternative embodiment of a table-based robotic system.
Figure 13:
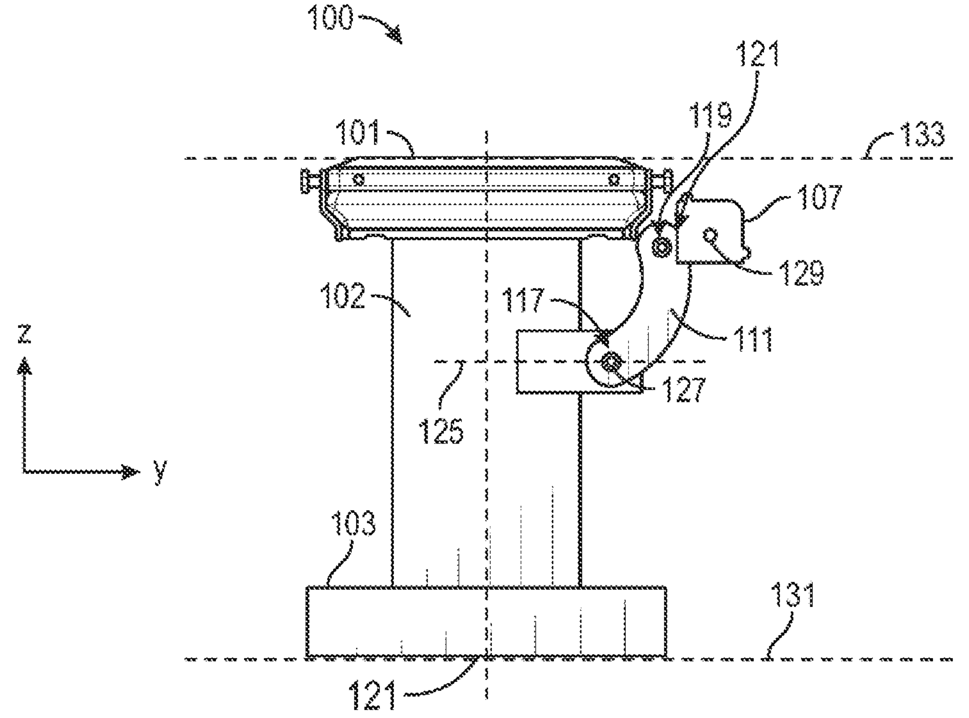
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
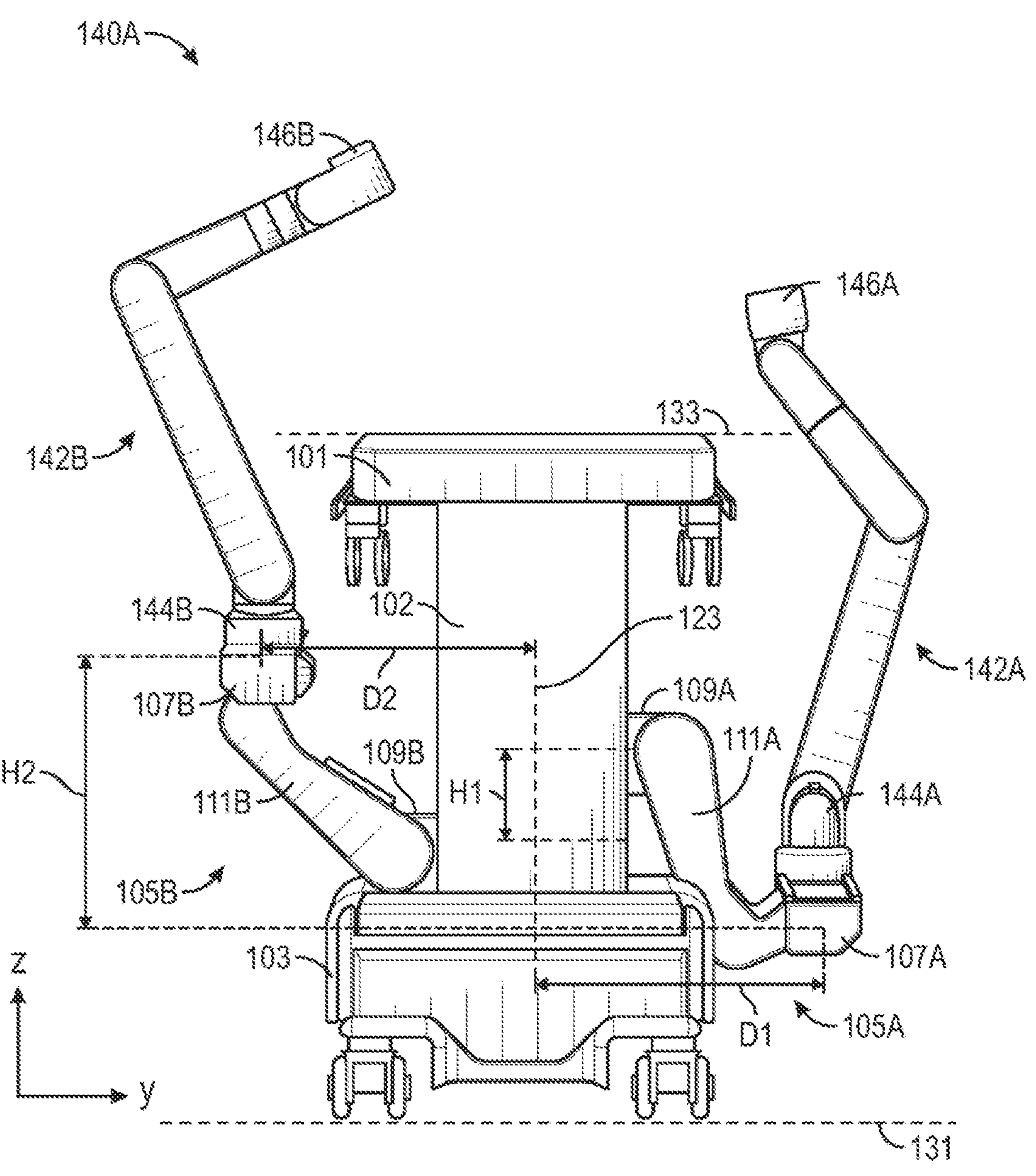
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
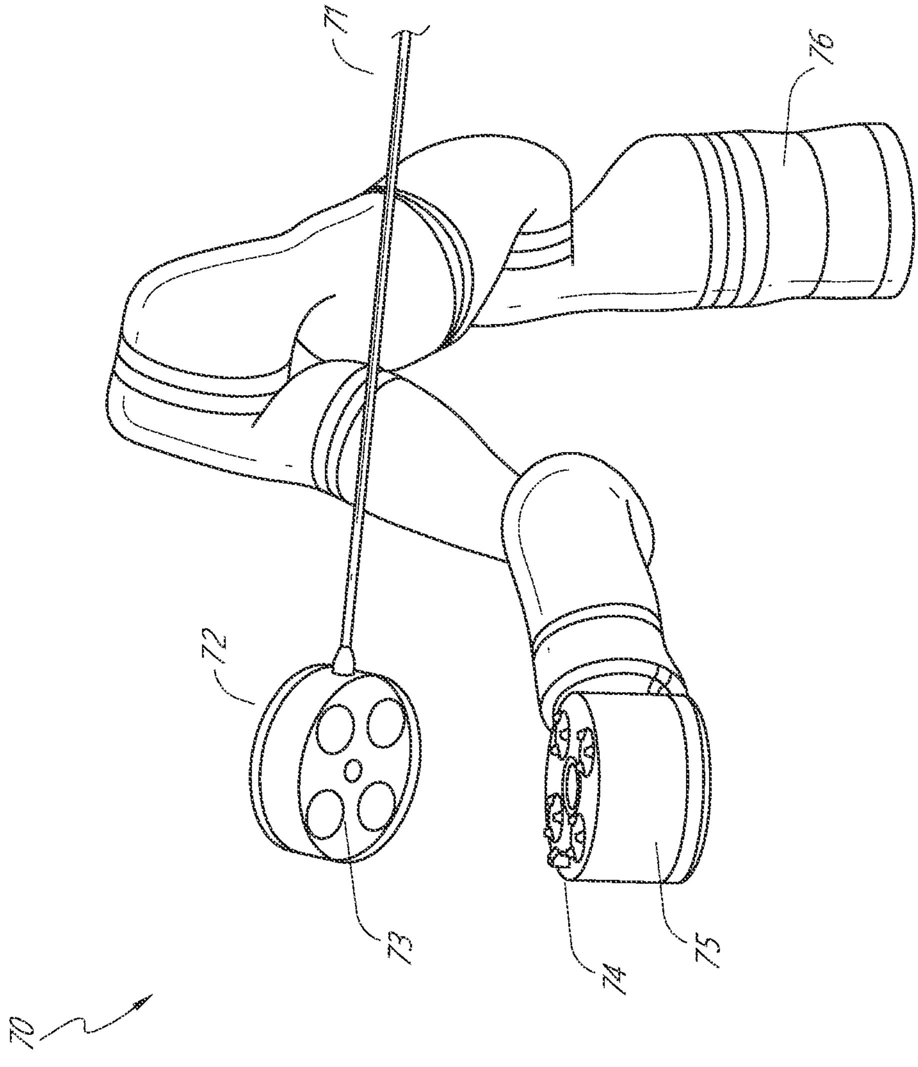
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
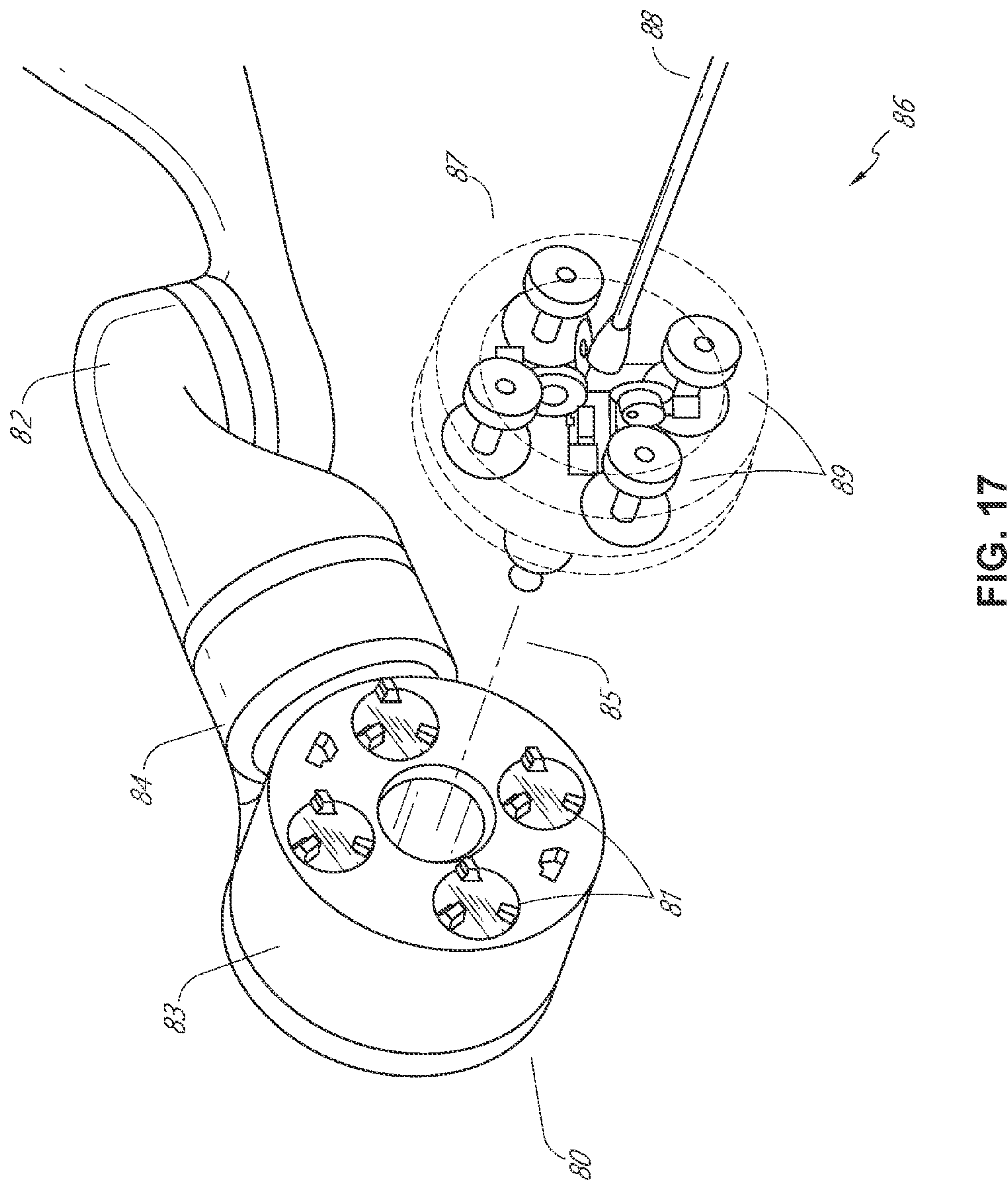
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
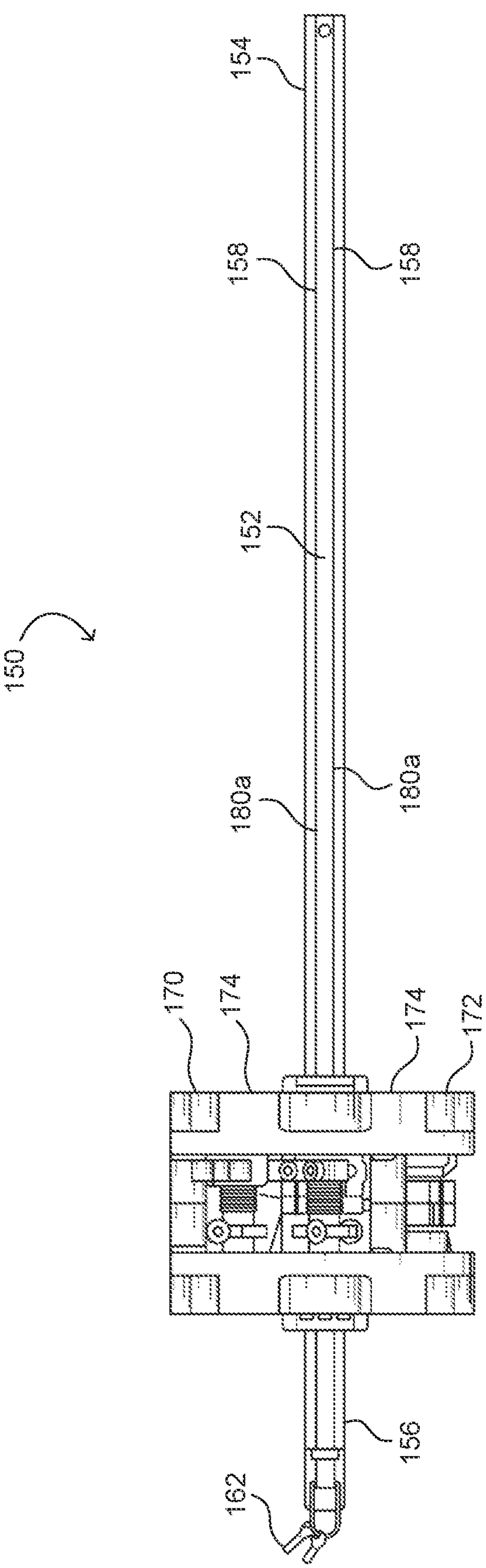
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
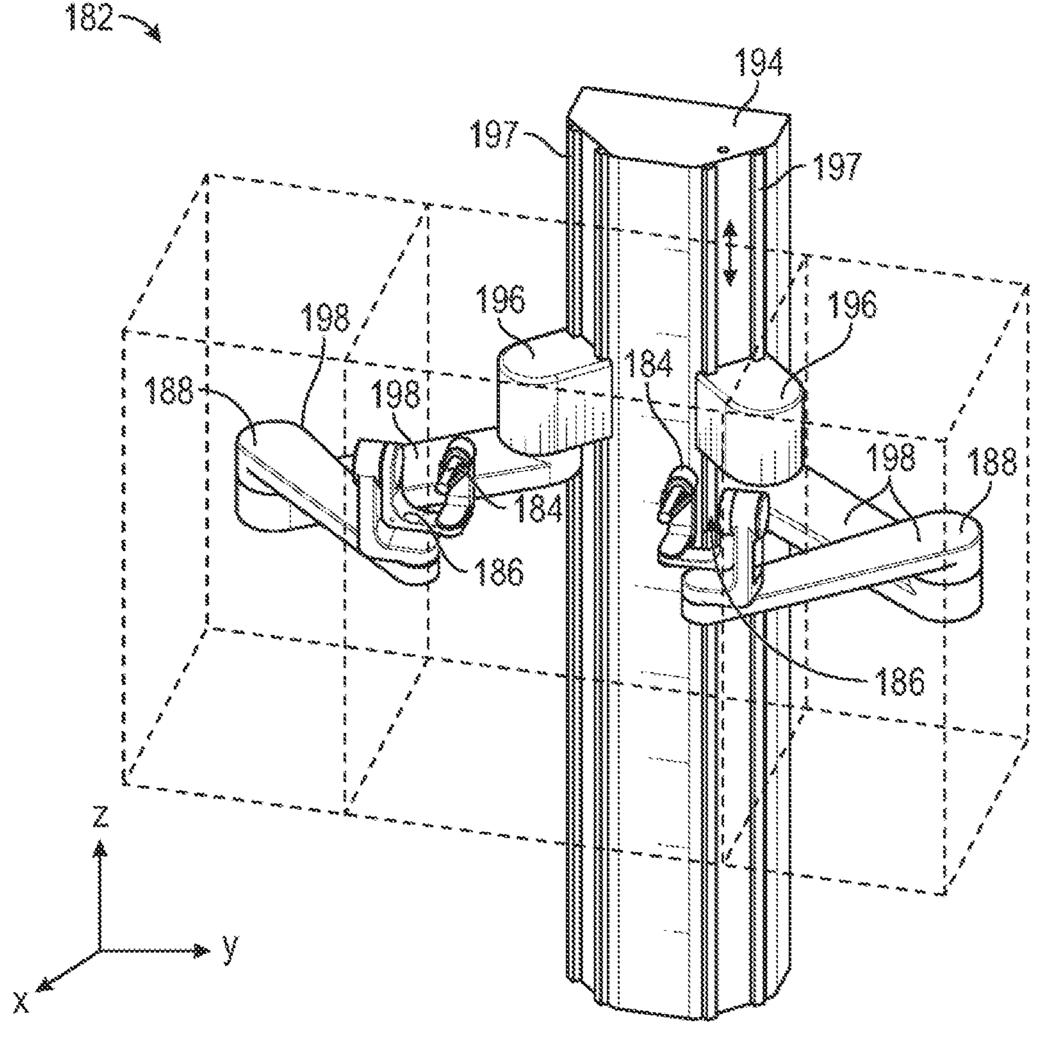
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
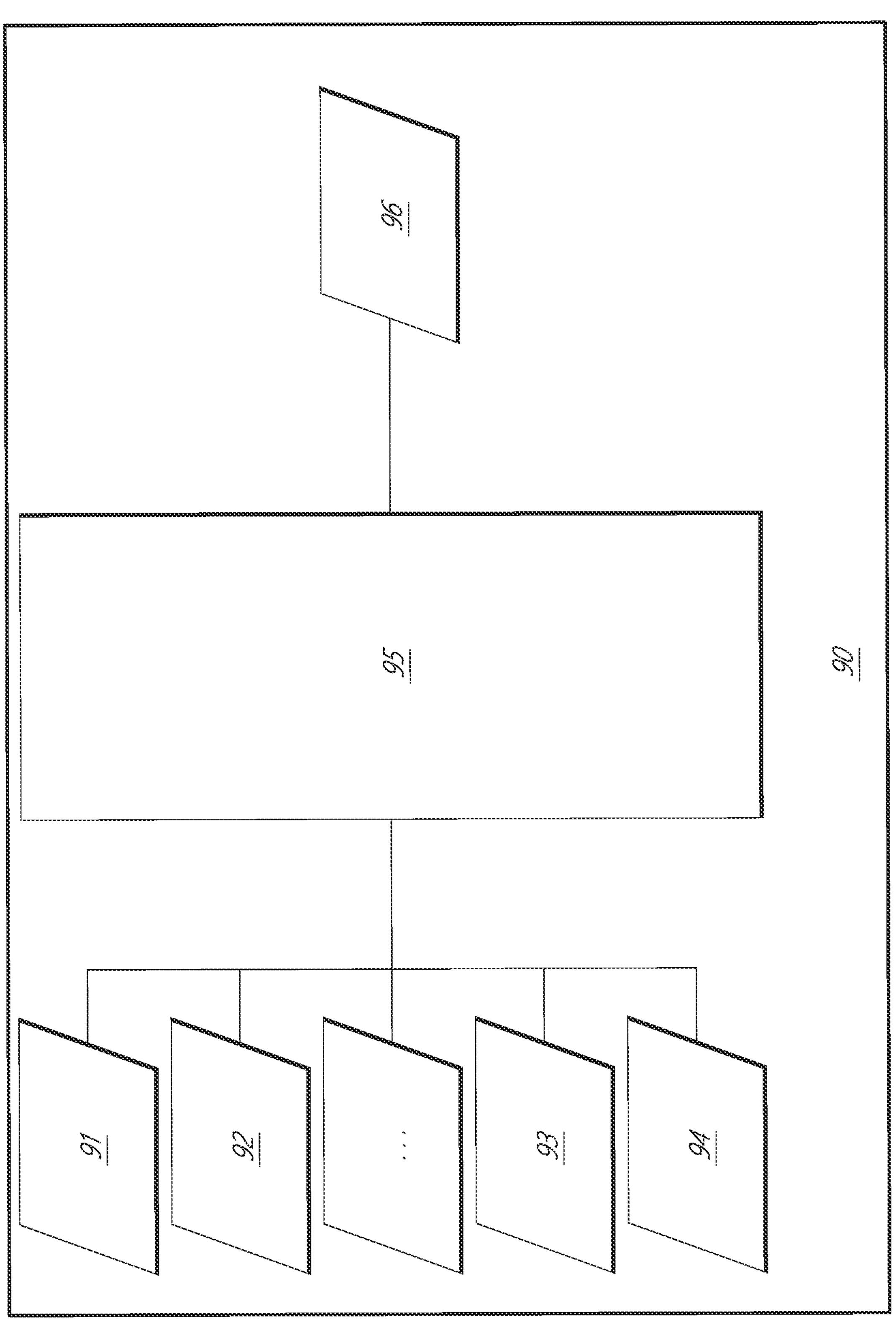
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Systems and Methods for Collision Avoidance.

This application discloses medical robotic systems that utilize information about objects in a vicinity of the medical robotic systems to avoid or reduce the risk of future collisions. As described herein, robotic medical systems may include a plurality of robotic arms configured to control the movement of medical tool(s) during a given medical procedure. In order to achieve a desired pose of a medical tool, a robotic arm may be placed into a pose, which may cause the robotic arm to come into contact with an external object, such as, for example, a patient, bedside staff, or inanimate object(s) (e.g., accessories on the bed). By detecting contact between the robotic arm and the external object early enough (e.g., immediately upon contact, or at least before the contact results in a force greater than a threshold value), the safety of the robotic surgery can be improved.

Information about the objects in the vicinity may include contact information, which is obtained using contact sensors such as force sensors, and non-contact information, which is obtained using non-contact sensors. Based on the information about the objects in the vicinity of the medical robotic systems, configurations of kinematic chains (e.g., robotic arms and adjustable arm supports) are adjusted to, for example, increase the distance from the objects in the vicinity and reduce the likelihood of future collision.

A. Robotic Arms and Sensor Architecture for Detecting Contact or Obtaining Control Information The medical robotic systems include a plurality of sensors to collect information (e.g., position information) about objects in the vicinity of the medical robotic systems. Some of the sensors are located on, or adjacent to, robotic arms of the medical robotic systems.

Figure 21:
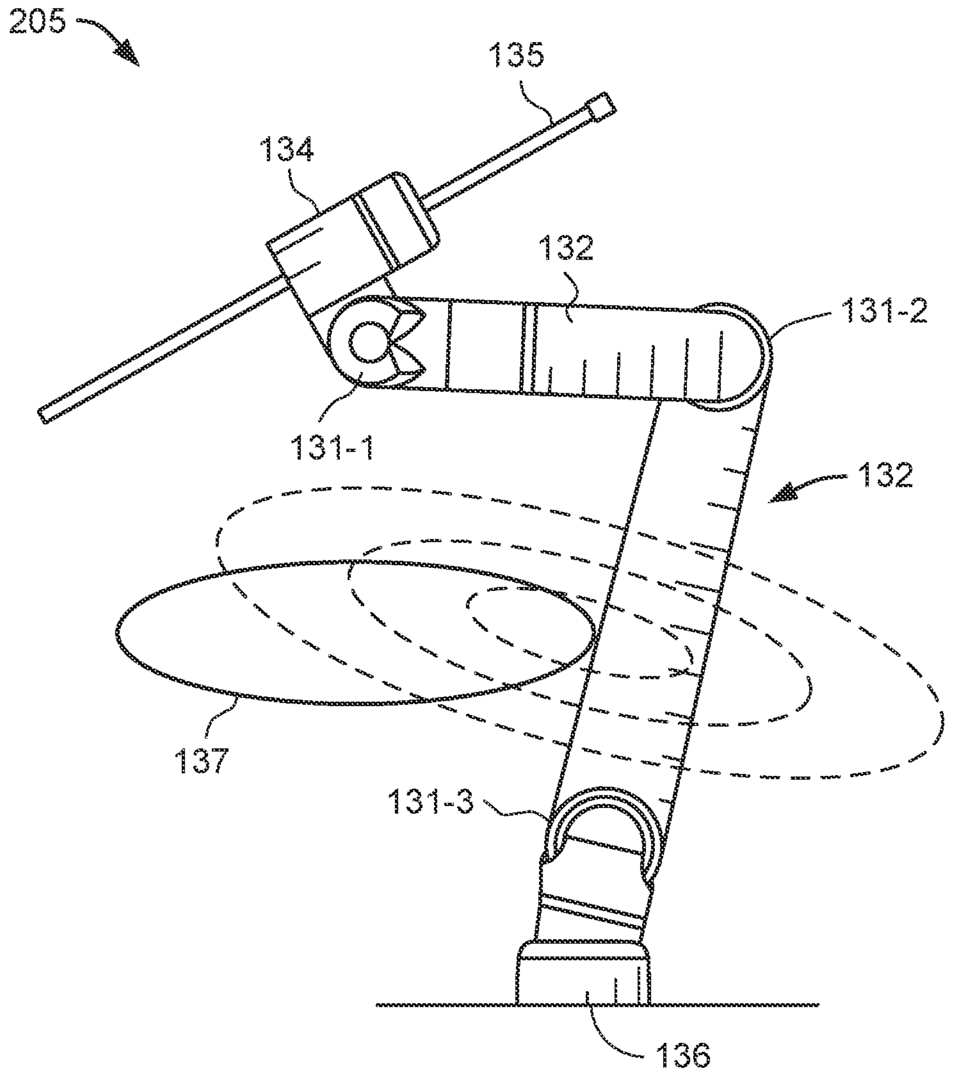
FIG. 21 illustrates an exemplary robotic arm in accordance with some embodiments.

FIG. 21 illustrates an exemplary robotic arm 205 in accordance with some embodiments. The robotic arm 205 includes a plurality of links 132 which are connected by one or more joints 131 (e.g., 131-1 through 131-3). A proximal end of the robotic arm 205 may be connected to a base 136 and a distal end of the robotic arm 205 may be connected to an advanced device manipulator (ADM) 134 (also referred to as an instrument driver or end effector of the robotic arm). The ADM 134 may be configured to control the positioning and manipulation of a medical tool 135 (also referred to as a medical instrument). Thus, the links 132 may be detachably coupled to the medical tool 135. The joints 131 provide the robotic arm 205 with a plurality of degrees-of-freedom (DoFs) that facilitate control of the medical tool 135 via the ADM 134.

In some embodiments, the robotic arm 205 includes one or more force-based sensors for detecting a contact between any part of the robotic arm 205 and an object 137 other than the robotic arm 205 (e.g., another robotic arm, other medical equipment, patient, medical personnel, etc.). In some embodiments, such sensors are located within, or adjacent to, the joints 131. For example, one or more force sensors may be located at the joint 131-3. The one or more force sensors located at the joint 131-3 can detect interaction forces (e.g., the magnitude and/or direction of the forces and/or moments) from the proximal end of the robotic arm 205. Additionally or alternatively, one or more force sensors may be located at or near the joint 131-1 near the distal end of the robotic arm 205. The one or more force sensors located at or near the joint 131-1 may include a six-axis load cell that is capable of detecting both force and moment (e.g., torque) with respect to six axes (e.g., force along x, y, and z-axes and torques about x, y, and z-axes). Based on the forces detected by the one or more sensors, one or more processors can determine the location of the contact and one or more parts of the robotic arm 205 (one or more links or joints, the ADM 134, or the medical tool 135) that are involved in the contact.

Figures 22A, 22B:
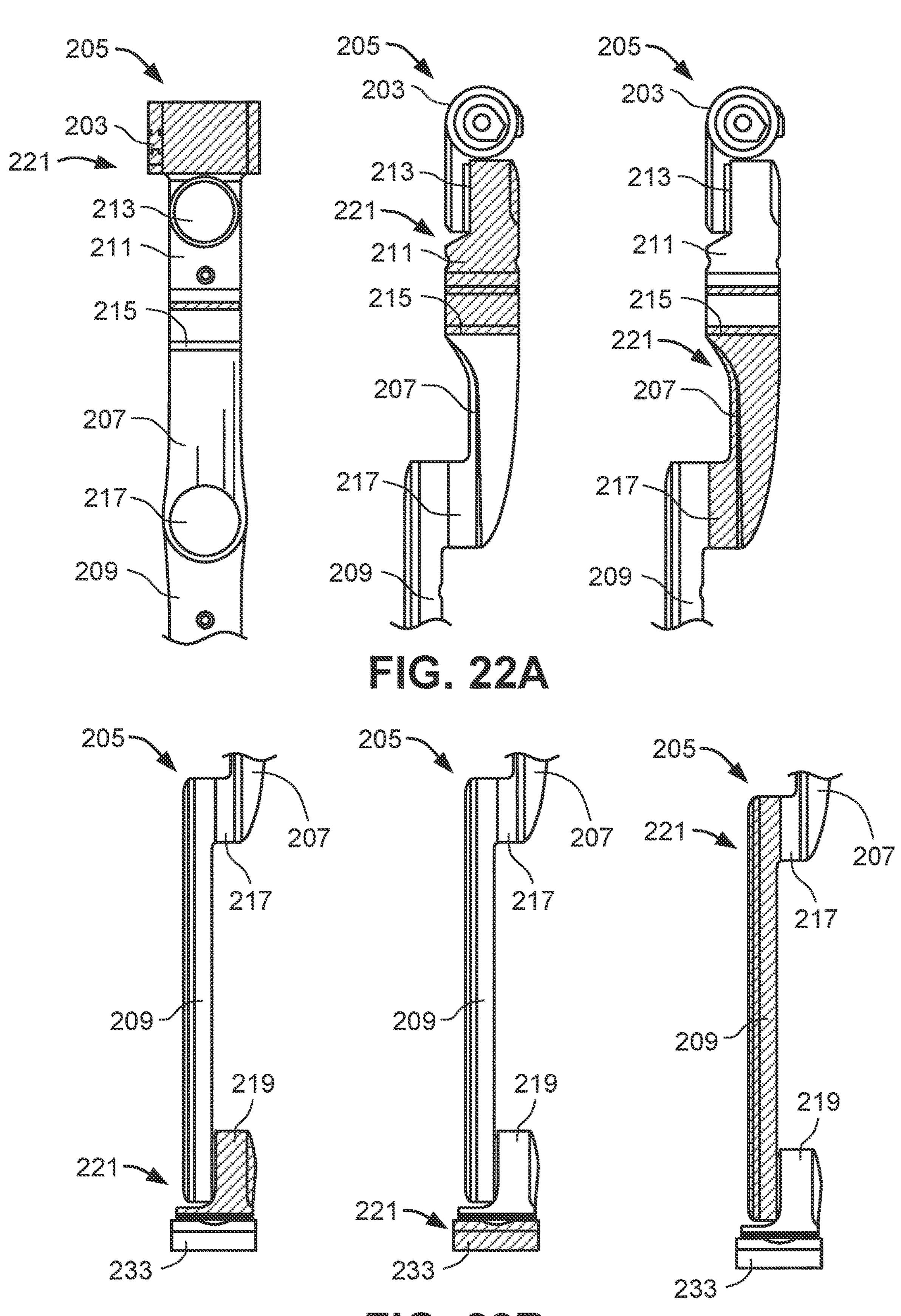
FIGS. 22A and 22B illustrate example robotic links that can form a portion of a robotic arm in accordance with some embodiments.

Additionally, or alternatively, the robotic arm 205 includes one or more contact sensors. FIGS. 22A and 22B illustrate example robotic links that can form a portion of a robotic arm with one or more contact sensors in accordance with some embodiments.

FIG. 22A illustrates three views of a distal portion of a robotic arm 205, whereas FIG. 22B illustrates three views of a portion of the robotic arm 205 that is proximal to the distal portion of FIG. 22A. With reference to FIGS. 22A and 22B, the robotic arm 205 may include a device manipulator 203, a plurality of links 207, 209, 211, and 233, and a plurality of joints 213, 215, 217, and 219 connecting the device manipulator 203 and the links 207, 209, 211, and 233. In each of the views illustrated in FIG. 22A, regions 221 of the robotic arm 205 which have a relatively higher likelihood of colliding with a patient are highlighted.

In some embodiments, an arm component (e.g., one of the robotic links 205-211 or joints 213-219 of FIGS. 22A-22B) is coupled with one or more sensors to sense contact with external objects such as a patient, bedside staff, or other object.

Figure 23:
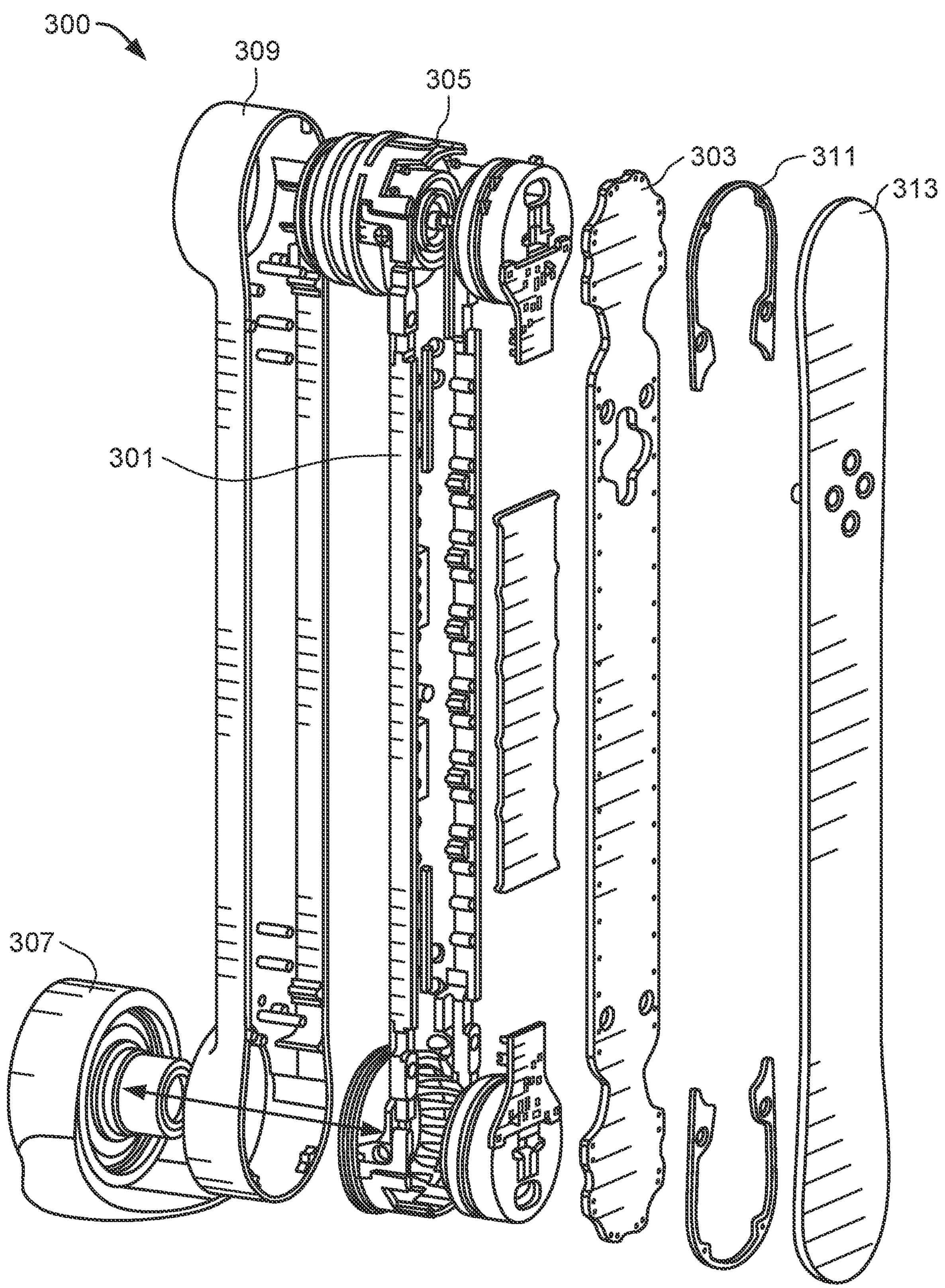
FIG. 23 illustrates an example link including a rigid shell and configured to detect contact with external objects in accordance with some embodiments.

In some embodiments, a shell can be suspended around a given link and the relative motion between the shell and inner components/members of the link can be detected using one or more sensors in order to detect contact with an external object. FIG. 23 illustrates an example link 300 including a rigid shell 309 and configured to detect contact with external objects in accordance with some embodiments. In particular, the link 300 includes a structural link 301, a structural cover 303, a first joint 305, a second joint 307, a shell 309, a pair of reaction paddles 311, and a shell cover 313. For example, the inner components of the link 300 may comprise the structural link 301 and the structural cover 303.

The structural cover 303 can be attached to the structural link 301 to house components of the structural link 301 and form the internal structural connection between the first joint 305 and the second link. The shell 309 together with the shell cover 313 are suspended from and surround the structural link 301. As used herein, the shell 309 and shell cover 313 may collectively be referred to simply as the "shell" 309, while the structural link 301 and structural cover 303 may collectively be referred to simply as the structural link 301 or a manipulatable link, unless the context clearly indicates otherwise.

The shell 309 may be connected to the structural link 301 via force-sensing connections. Because the shell 309 surrounds the structural link 301, when the link 300 contacts an external object, the object will come into contact with the shell 309. Thus, the force-sensing connection can detect contact between the shell 309 and the external object by measuring changes in the force between the shell 309 and the structural link 301 caused by the link 300 coming into contact with the external object. The shell 309 may also be sufficiently rigid such that, upon contact with an external object, the shell 309 engages the force-sensing connection. Advantageously, by using a rigid shell 309 the force and relative movement between the shell 309 and the structural link 301 can be sensed in all three directions.

The force-sensing connection may be implemented in a variety of different manners in accordance with some embodiments. For example, the force-sensing connection can include one or more of the following: traditional load cells, force sensing resistors, and/or any component capable of sensing force (or displacement, when combined with a spring).

Figure 24:
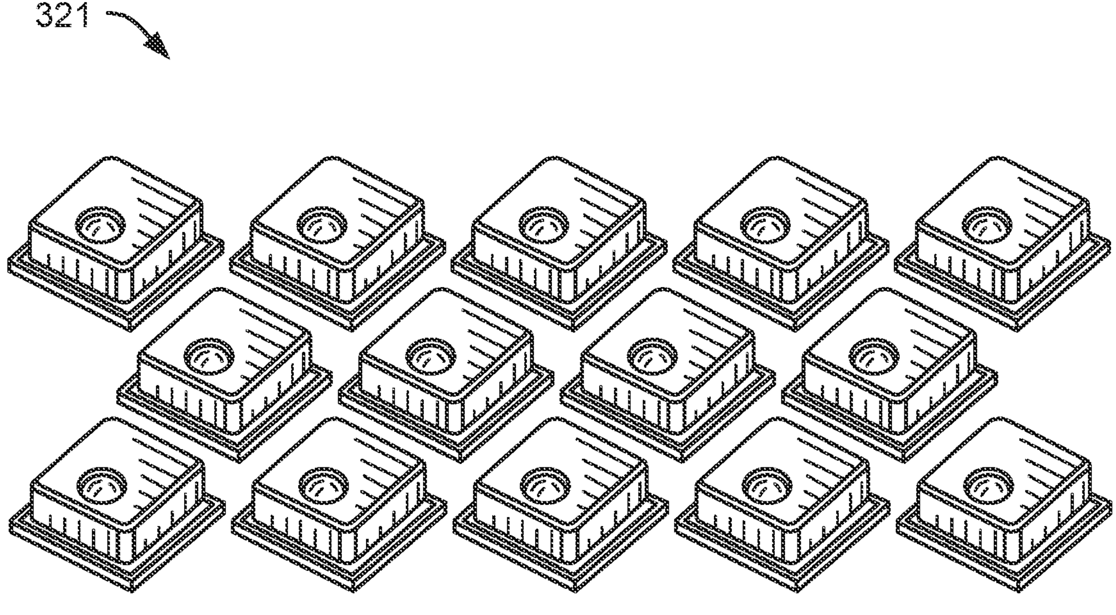
FIG. 24 illustrates an example of force-sensing sensors that can be used in the link of FIG. 23 in accordance with some embodiments.

FIG. 24 illustrates one example of a force-sensing connection that can be used in the link 300 of FIG. 23 in accordance with some embodiments. In particular, the force-sensing connection can include a plurality of shell sensors 321 (e.g., fourteen shell sensors in the illustrated embodiment), which can be disposed between the structural link 301 and the shell 309.

Figure 25A:
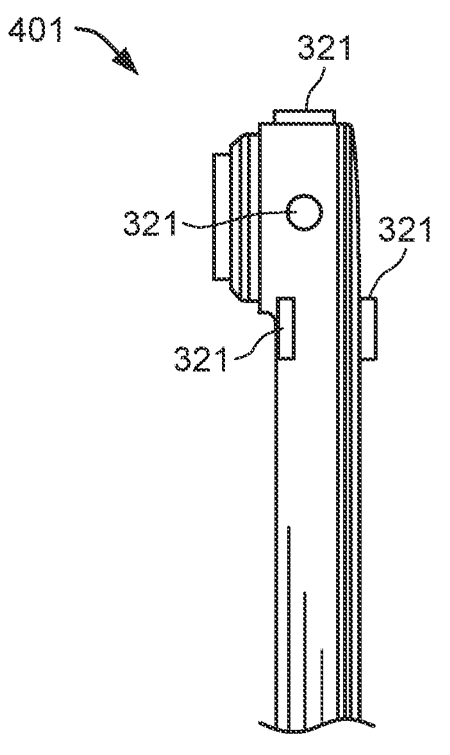
FIGS. 25A and 25B illustrate two views of a link in which a plurality of sensors are included in a link in accordance with some embodiments.
Figure 25B:
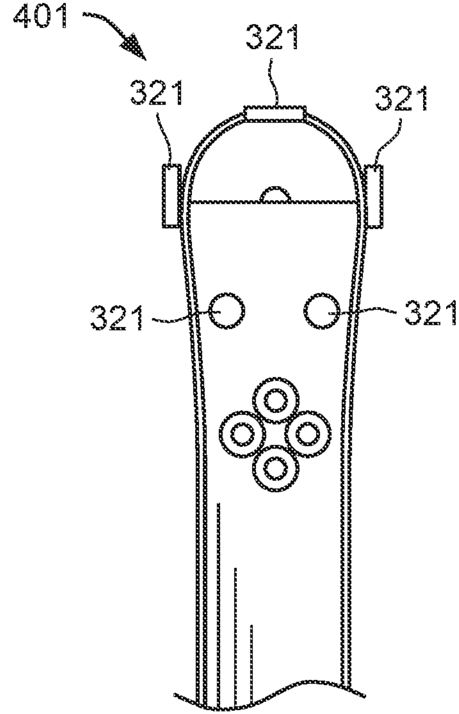

In some embodiments, the sensors 321 are distributed throughout the link 300 in between the shell 309 and the structural link 301. For example, the shell 309 can be suspended over the structural link 301 via the sensors 321. Depending on the implementation, the link 300 can include one, two, three, four or more sensors 321 distributed along a robotic arm link. FIGS. 25A and 25B illustrate two views of a link 401 in which fourteen sensors 321 are included in the link 401 in accordance with some embodiments. In particular, FIGS. 25A and 25B illustrate, respectively, a side view and a front view of one end of the link 401 which includes seven sensors 321. The link 401 may be substantially symmetric at both ends of the link 401, thereby including a total of fourteen sensors 321 in the link 401.

Figure 25C:
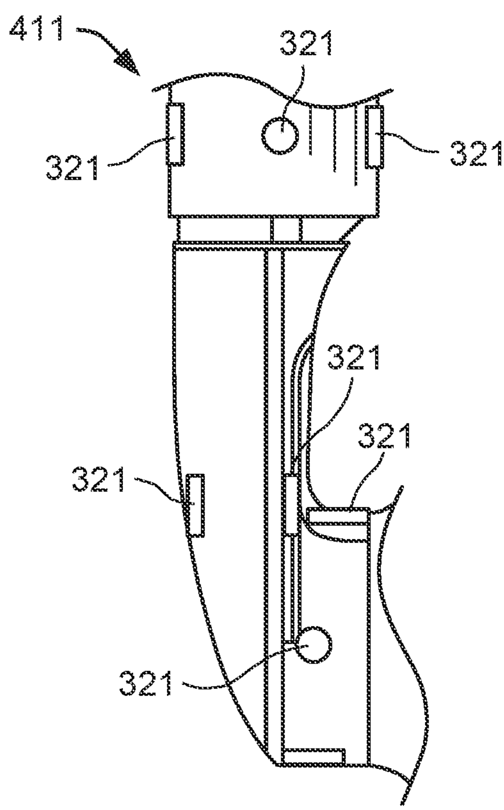
FIGS. 25C and 25D illustrate two view of a link in which a plurality of sensors are included in a link in accordance with some embodiments.
Figure 25D:
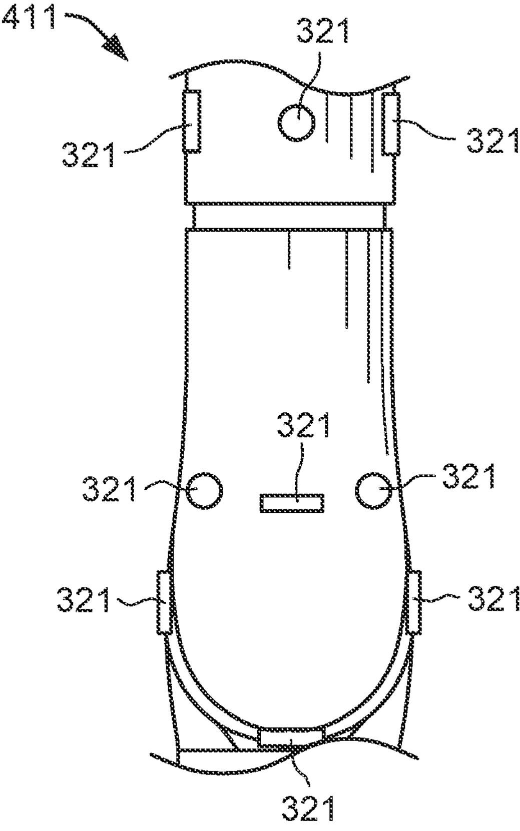

FIGS. 25C and 25D illustrate two view of a link 411 in which twelve sensors 321 are included in the link 411 in accordance with some embodiments. In some implementations, a robotic arm may include both the link 401 and the link 411, with the link 401 positioned proximal to the link 411. In particular, FIGS. 25C and 25D illustrate, respectively, a side view and a front view of the link 411, which includes twelve sensors 321. The link 411 may be substantially symmetric at both ends of the link 411, thereby including a total of twenty-four sensors 321 in the link 401. In a number of implementations, the plurality of sensors 321 can be configured to support the rigid shell without being fixed to the rigid shell. In some implementations, the link 401 or 411 may further include one or more supports configured to support the rigid shell relative to the structural link. For example, the one or more supports can include spring(s), flexure(s), and/or suspension(s).

Although FIGS. 25A-25D illustrate links 401 and 411 including a plurality of sensors 321, in some embodiments, the links can include a single sensor configured to sense force and/or displacement between the structural link 301 and the shell 309 in multiple directions. Using signals received from the sensor(s) 321, the robotic system can be configured to detect a direction of the contact between the shell 309 and the external object. The robotic system can also measure a magnitude of a force resulting from the contact between the shell 309 and the external object based on the signal from the sensor(s) 321. Based on the placement of the plurality of sensors 321 within the links 401 and 411, the robotic system can also be configured to detect a torque applied to the link. For example, if a torque is applied to the shell 309, certain sensors 321 on one side of the links 401 and 411 may be compressed. Based on the positions of and forces sensed by the sensors 321 being compressed, the robotic system can determine a torque applied to the links 401 and 411.

Referring back to FIG. 21, the robotic arm 205 may be placed in various poses while the one or more sensors 321 detect a contact or collision between any part of the robotic arm 205 and another object. In some circumstances, there are additional constraints on the movement of the robotic arm 205. For example, during a medical procedure, it can be desirable to have the ADM 134 of the robotic arm 205 and/or a remote center of movement (RCM) of the tool 135 coupled thereto kept in a static pose/position. An RCM may refer to a point in space where a cannula or other access port through which a medical tool 135 is inserted is constrained in motion. In some implementations, the medical tool 135 includes an end effector that is inserted through an incision or natural orifice of a patient while maintaining the RCM.

In some circumstances, a robotic system can be configured to move one or more links 132 of the robotic arm 205 within a "null space" to avoid collisions with nearby objects (e.g., other robotic arms) while the ADM 134 of the robotic arm 205 and/or the RCM are maintained in their respective poses/positions. The null space can be viewed as the space in which a robotic arm 205 can move that does not result in movement of the ADM 134 and/or RCM, thereby maintaining the position and/or the orientation of the medical tool 135. In some implementations, a robotic arm 205 can have multiple positions and/or configurations available for each pose of the ADM 134.

For a robotic arm 205 to move the ADM 134 to a desired pose in space, in certain implementations, the robotic arm 205 may have at least six DoFs— three DoFs for translation (e.g., X, Y, Z position) and three DoFs for rotation (e.g., yaw, pitch, and roll). In some implementations, each joint 131 may provide the robotic arm 205 with a single DoF, and thus, the robotic arm 205 may have at least six joints to achieve freedom of motion to position the ADM 134 at any pose in space. To further maintain the ADM 134 of the robotic arm 205 and/or the remote center or motion in a desired pose, the robotic arm 205 may further have at least one additional "redundant joint." Thus, in certain implementations, the system may include a robotic arm 205 having at least seven joints 131, providing the robotic arm 205 with at least seven DoFs. However, depending on the implementation, the robotic arm 205 may have a greater or fewer number of DoFs.

A robotic arm 205 having at least one redundant DoF (also called a "kinematically redundant" robotic arm) may refer to a robotic arm 205 having at least one more DoF than the minimum number of DoFs necessary for performing a given task. For example, a robotic arm 205 can have at least seven DoFs, where one of the joints 131 of the robotic arm 205 can be considered a redundant joint for completing a task that requires six DoFs. The one or more redundant joints can allow a robotic arm 205 to move in a null space to both maintain the pose of the ADM 134 and a position of an RCM and avoid collision(s) with other arms or objects.

A robotic system (e.g., the system 36 of FIG. 6 or the system 140A of FIG. 14) can be configured to perform collision avoidance to avoid collision(s), e.g., between adjacent robotic arms by taking advantage of the movement of one or more redundant joints (e.g., either individually or in coordinated motion) in a null space. For example, when a robotic arm collides with or approaches (e.g., within a defined distance of) another robotic arm, one or more processors of the system can be configured to detect the collision or impending collision (e.g., via kinematics). Accordingly, the system can control one or both of the robotic arms to adjust their respective joints within the null space to avoid the collision or impending collision. In some implementations involving a pair of robotic arms, a base of one of the robotic arms and its end effector can maintain their pose, while links or joints therebetween move in a null space to avoid collision with an adjacent robotic arm.

Figures 26, 27:
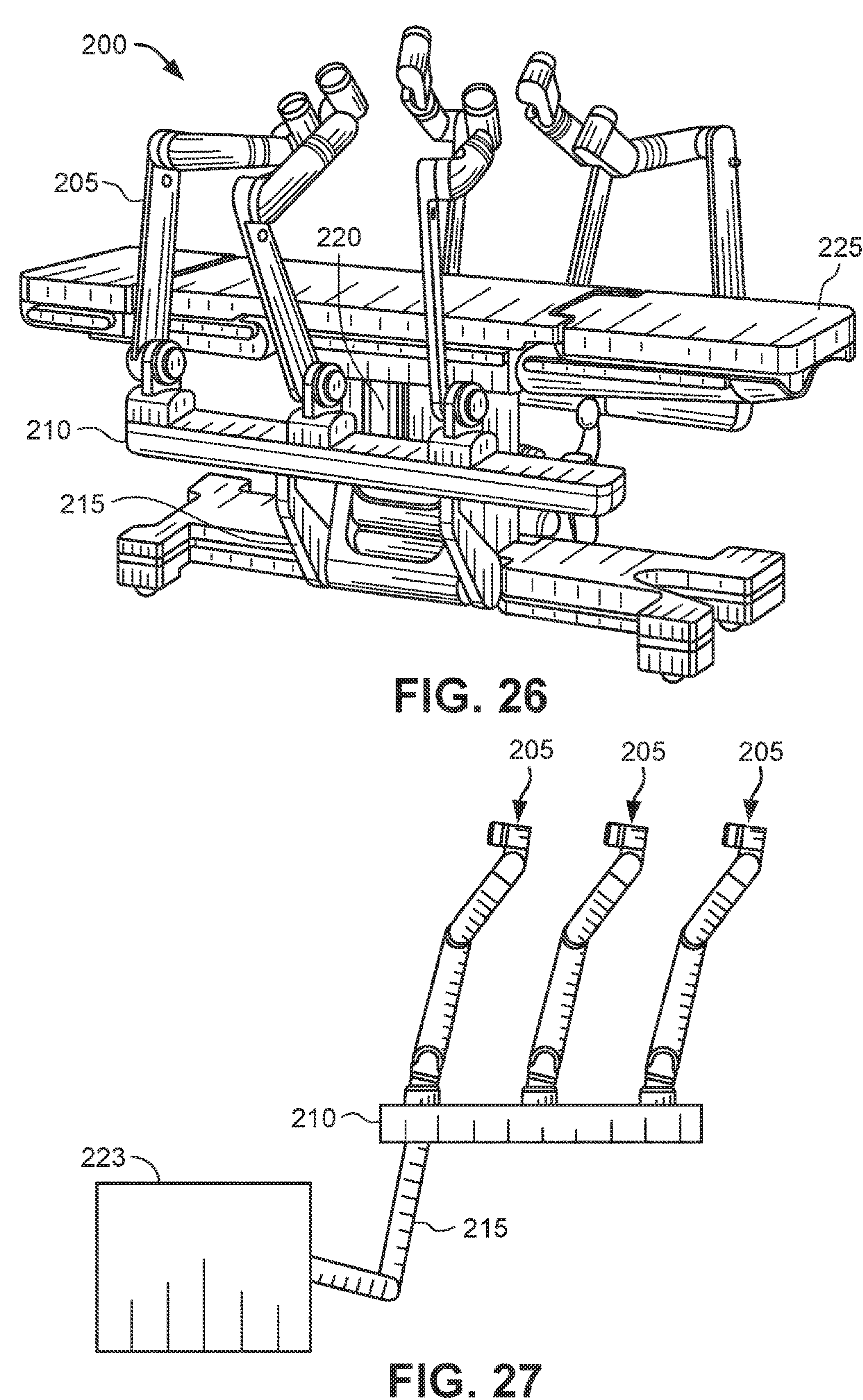
FIG. 26 illustrates an example of a robotic system including an adjustable arm support in accordance with some embodiments.
FIG. 27 schematically illustrates how one or more degrees-of-freedom (DoFs) can be shared between robotic arms, an adjustable arm support, and a set-up joint.

FIG. 26 illustrates an example of a robotic system 200 including an adjustable arm support 210 in accordance with some embodiments. In FIG. 26, the robotic system 200 includes a plurality of robotic arms 205, one or more adjustable arm supports 210, one or more set-up joints 215, and a bed column 220. Each of the robotic arms 205 may be supported by one of the adjustable arm supports 210 and the adjustable arm support(s) 210 may be in turn supported by the set-up joint(s) 215. As described above, each robotic arm 205 may have a plurality of DoFs. Similarly, the adjustable arm support(s) 210 and the set-up joint(s) 215 may be moveable in one or more DoFs.

FIG. 27 schematically illustrates how one or more DoFs can be shared between robotic arms, an adjustable arm support, and a set-up joint. FIG. 27 shows a system where a set-up joint 215 may be coupled to a bed support 223 at a proximal end and to an adjustable arm support 210 at a distal end. Further, a plurality of robotic arms 205 may be coupled to the adjustable arm support 210 at their respective proximal ends. In certain implementations, the adjustable arm support 210 and the set-up joint 215 together may have four DoFs. Thus, the robotic arms 205 attached to the adjustable arm support 210 may share the four DoFs provided by the set-up joint 215 and the adjustable arm support 210.

Thus, dependent on the implementation, a robotic medical system can have many more robotically controlled degrees of freedom beyond just those in the robotic arms to provide for null space movement and collision avoidance. In each of these implementations, the end effectors of one or more robotic arms (and any tools or instruments coupled thereto) and/or a remote center (e.g., along an axis of a tool) associated therewith can advantageously maintain in pose and/or position within a patient.

In some embodiments, robotic systems described herein utilize shared DoFs between different link members (e.g., of a plurality of robotic arms and/or an adjustable arm support) to achieve null space movement for collision avoidance. In certain implementations, the system can use one or more DoFs associated with a first set of one or more motorized links (e.g., in the form of one or more robotic arms—e.g., the robotic arms 205 illustrated in FIG. 26) in coordinated and/or synchronized motion with one or more DoFs associated with a second set of one or more motorized links (e.g., in the form of support links that support the robotic arms, including one or more set-up joint links and one or more arm support links—e.g., the set-up joint 215 and adjustable arm support 210 illustrated in FIG. 26) to achieve null space movement for collision avoidance.

The first set of one or more motorized links (e.g., in the form of one or more robotic arms) can be configured to perform a different function from the second set of one or more motorized links (e.g., in the form of adjustable arm support links or rails). In some implementations, the first set of one or more links is supported by the second set of one or more links.

Moreover, in some implementations, the first set of one or more motorized links has a different number of DoFs from the second set of one or more motorized links. For example, as shown in the simplified implementation illustrated in FIG. 27, the first set of one or more links may form three robotic arms 205 each having 7 or more DoFs. For example, each of the robotic arms 205 may have DoFs including but not limited to shoulder yaw, shoulder pitch, elbow pitch, wrist yaw, wrist pitch, roll, and insertion. The second set of one or more motorized links may form a set-up joint 215 in combination with an adjustable arm support 210 having 4 or more DoFs. For example, the set-up joint 215 and the adjustable arm support 210 may have DoFs including but not limited to vertical translation or "Z-lift," longitudinal translation along the bed, tilt, and upward pivot. The DoFs of the set-up joint 215 and adjustable arm support 210 are also illustrated in FIG. 24, as discussed above.

In some other implementations, the first set of one or more motorized links can have the same number of DoFs as the second set of one or more motorized links. Advantageously, by sharing DoFs between the first set of one or more links and the second set of one or more links, the number of DoFs for null space movement and collision avoidance can be expanded.

Aspects of this disclosure relate to robotic systems having one or more DoFs in addition to the DoFs of the robotic arms that are capable of null space movement. These extra DoFs (e.g., from the set-up joint in combination with the adjustable arm support) can affect the motion of the robotic arm(s) coupled to the adjustable arm support and assist in collision avoidance. For example, the DoFs from the second set of links including vertical translation, longitudinal translation, and tilt can be particularly useful for null space movement when combined with the DoFs of each of the robotic arms.

In the implementations described above, the shared DoFs between different sets of link members are utilized for null space movement whereby at least one set of link members is associated with a robotic arm. In these implementations, the ADM of the robotic arm, as well as an RCM of a tool attached thereto, can advantageously be kept in pose/position.

B. Utilization of Force Information for Robotic Arm and/or Bar Optimization

Force information that is detected by one or more sensors described above (e.g., during a collision or contact between a robotic arm and an object such as the patient) can be transformed into a general constraint for robotic arm and/or adjustable arm support (also known as a "bar") optimization. In some instances, a medical procedure can start with standard port placement, whereby one or more robotic arms are attached at the port locations. When a collision occurs, collision information will be gathered via one or more of the force sensors (e.g., contact sensors including force sensors at one or more joints). Other potential sensors that can detect collision include sensors for detecting ultrasound or light. Such collision information includes the nature of the collision (e.g., arm to arm collision, arm to environment collision), the general location of the collision (e.g., whether the collision is on a link, a joint, the advanced device manipulator (ADM), etc.), and the estimated direction (e.g., collision vector) of the collision. This information will be used to generate an external constraint e.g., a potential/collision field e.g., originating at the location of the collision in the direction of the collision. This potential field can repel and "push" away nearby joints and links of a robotic arm and/or adjustable arm support, thereby advantageously avoiding further collisions. The strength of such a "push" can be a function of distance from nearby components to the location of the collision. With these constraints, in addition to optimizing one or more arms, the adjustable arm support/bar pose can also be optimized for the collision distance and robotic arm end effector workspace. This allows the system to easily recover from a collision and continue a procedure with less likelihood of future collision.

Figure 28:
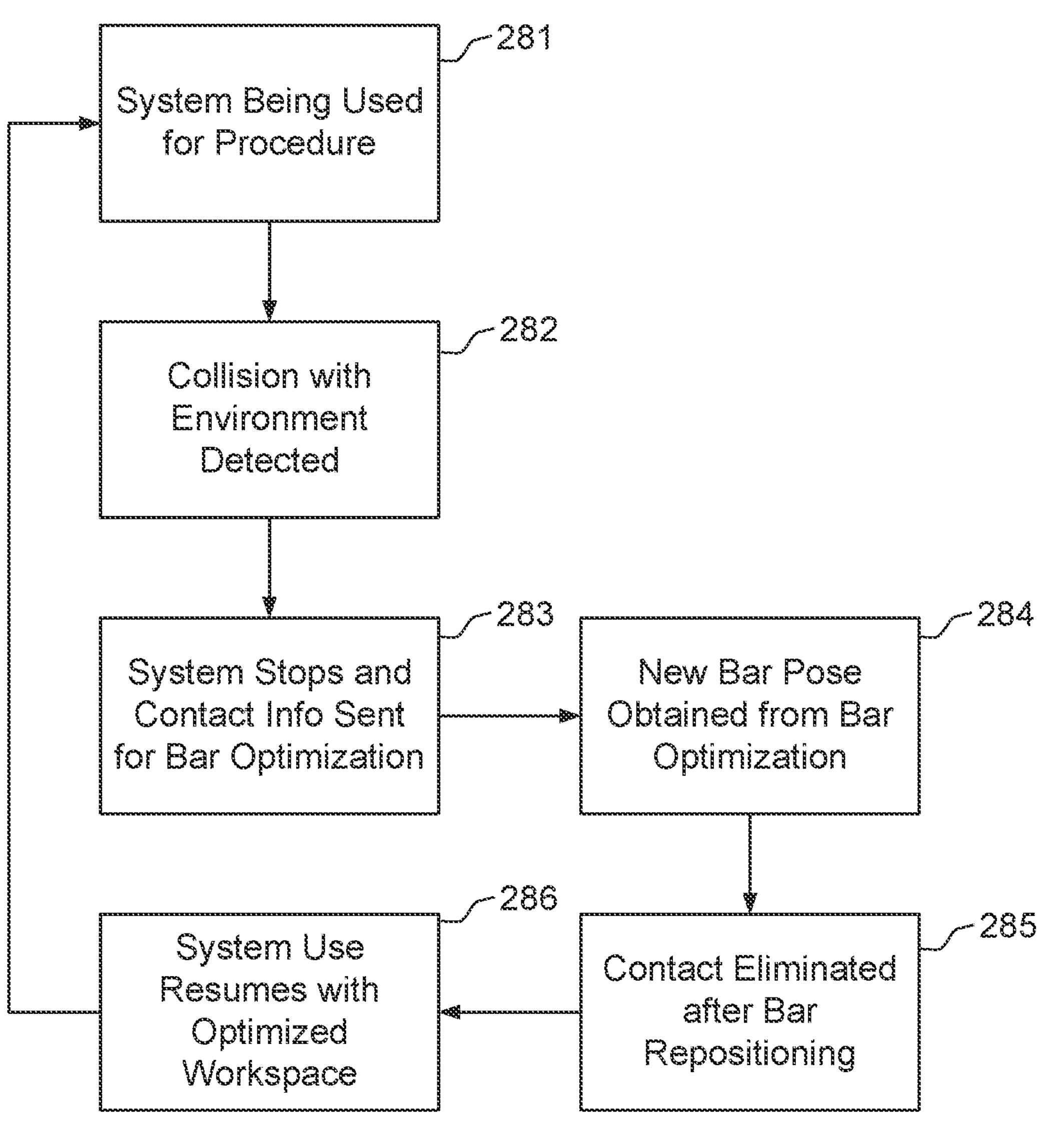
FIG. 28 is a flow diagram illustrating a method for adjusting one or more kinematic chains based on contact information in accordance with some embodiments.

FIG. 28 is a flow diagram illustrating a method for adjusting one or more kinematic chains (e.g., a respective kinematic chain includes an assembly of rigid bodies that are rotatably coupled to one another, such as one or more robotic arms coupled to an associated adjustable arm support/bar) based on contact information in accordance with some embodiments.

The workflow shown in FIG. 28 starts (operation 281) with the medical robotic system being used for a medical procedure, where the medical robotic system has one or more kinematic chains. While the system is being used for a medical procedure, a collision with a kinematic chain (e.g., a contact between a robotic arm and a patient) is detected (operation 282) (e.g., using one or more sensors described with respect to FIGS. 21, 22A-22B, 24, and 25A-25D). The medical robotic system halts (operation 283) movement of the kinematic chains and collects contact information. In some cases, the medical robotic system provides the contact information to a particular set of instructions (e.g., a software application) or an electronic device for optimization of the configuration of the one or more kinematic chains. In turn, the medical robotic system determines (operation 284) a new configuration of the kinematic chains, for example, by using the particular set of instructions or the electronic device, and places (operation 285) the kinematic chains into the determined configuration, thereby eliminating the contact with the kinematic chain. Thereafter, the medical robotic system resumes (operation 286) the medical procedure. As the kinematic chains are in optimized configurations, the likelihood of the kinematic chains coming into contact with the object is reduced. In some cases, the medical robotic system continues with the medical procedure (operation 281).

FIGS. 29A-29F illustrate configurations of robotic arms 205 during operation in accordance with the flow diagram of FIG. 28.

Figure 29A:
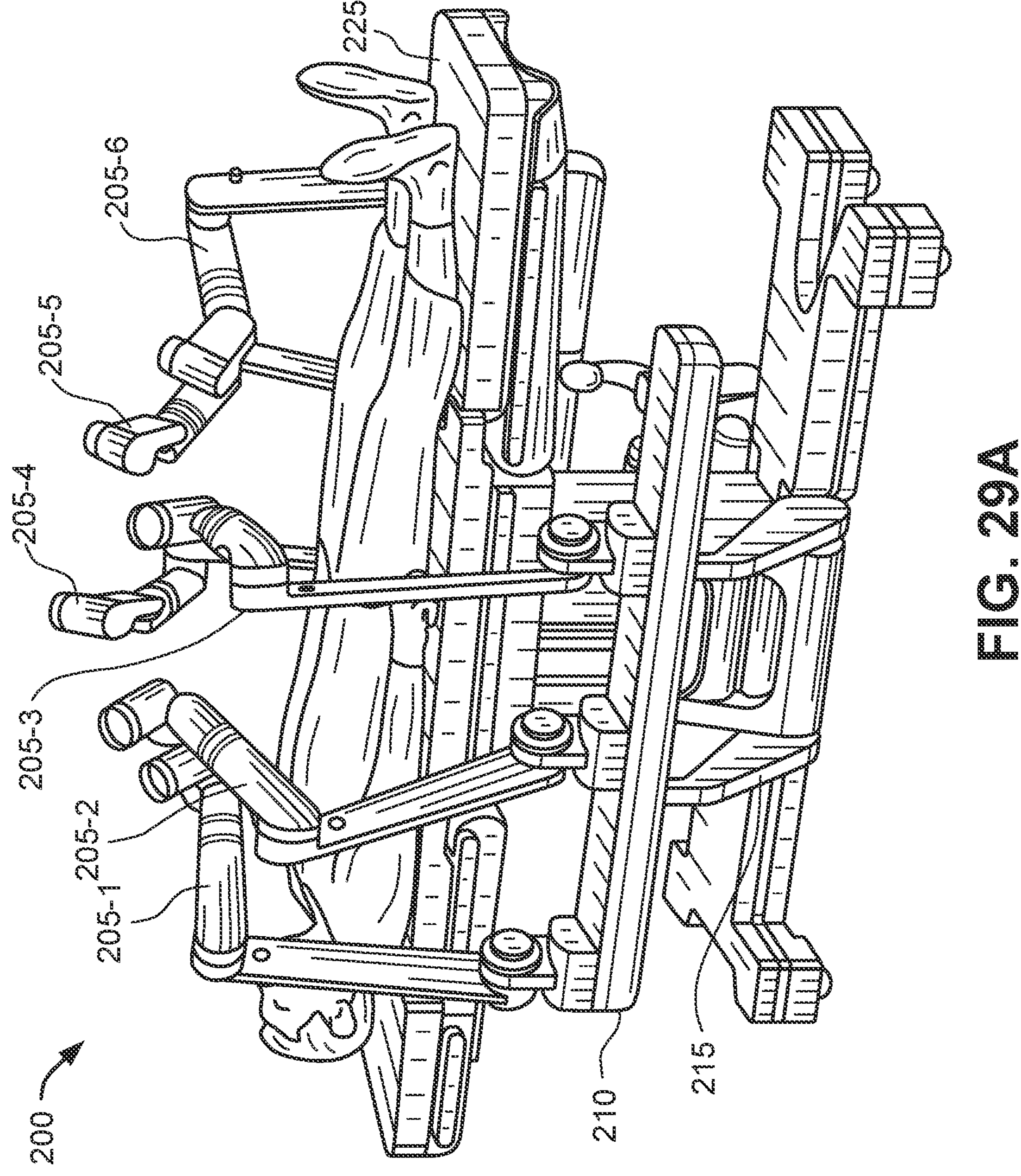
FIGS. 29A-29F illustrate configurations of robotic arms during operations shown in the flow diagram of FIG. 28.

FIG. 29A illustrates the medical robotic system 200 described with respect to FIG. 26, where a patient on the table top 225 is undergoing a medical procedure. In FIGS. 29A-29F, medical instruments are not shown so as not to obscure other aspects of the operations of the medical robotic system 200.

Figure 29B:
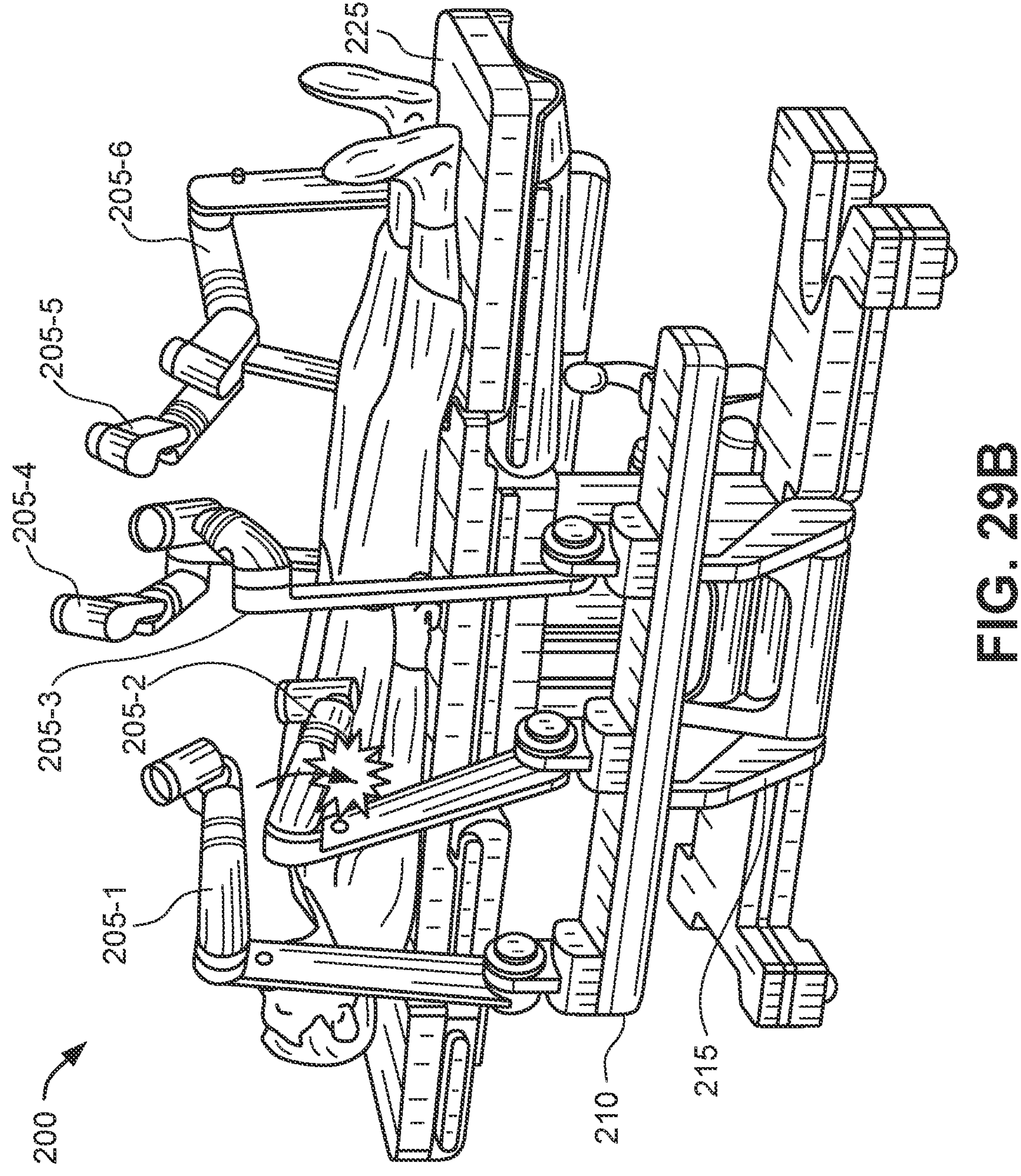
Figure 29C:
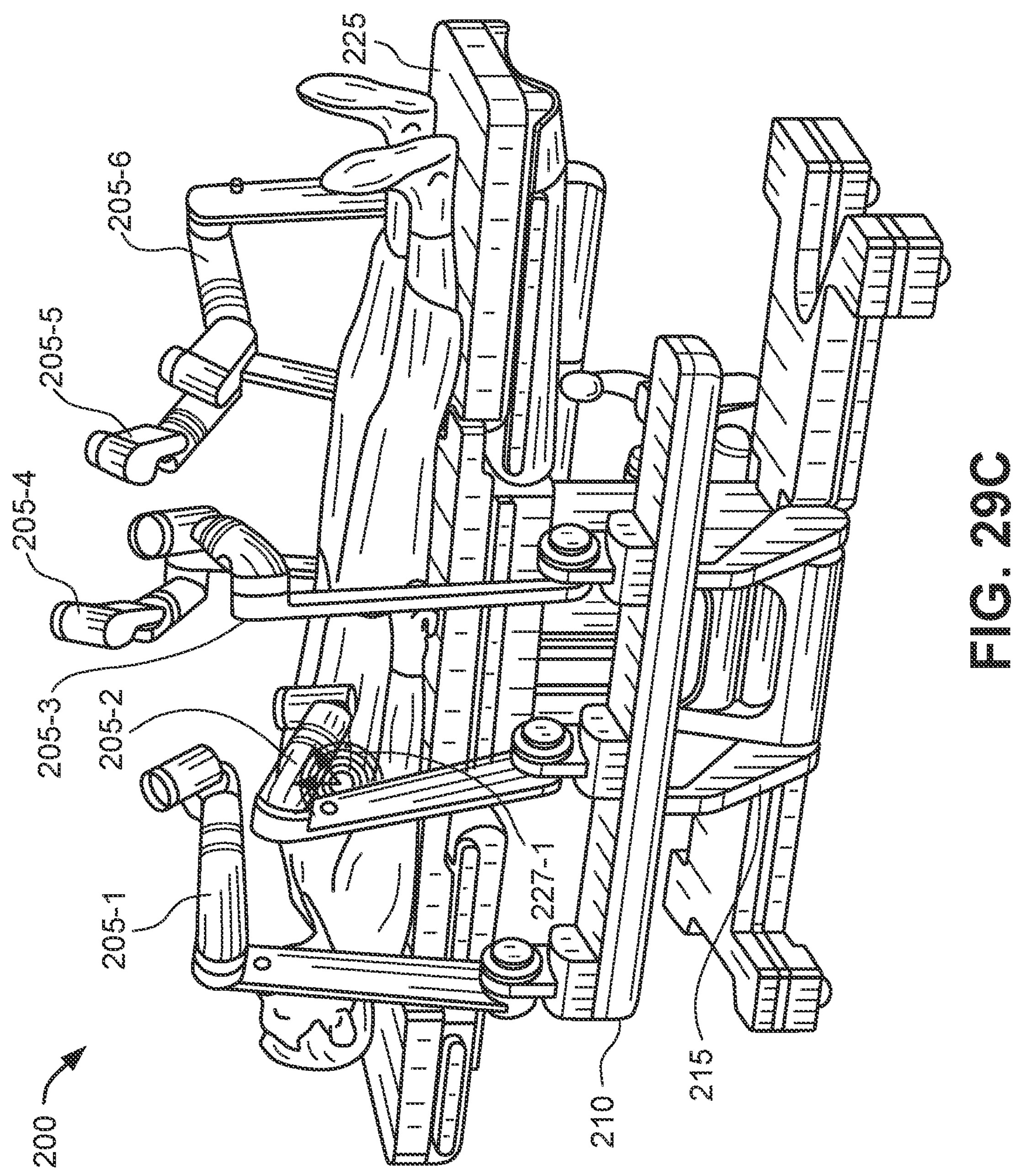

FIG. 29B shows that a robotic arm 205-2 moves down and a portion of the robotic arm 205-2 comes into contact with the patient. FIG. 29C shows that the medical robotic system 200 (or one or more processors thereof) receives contact information (e.g., a location of the contact, a direction of the contact, a force of the contact, etc.) and models the contact in a map (e.g., a three-dimensional map modeling objects in the vicinity of the medical robotic system 200). For example, the contact or collision can be modeled as a constraint or a potential field in the map. In FIG. 29C, the contact is modeled as a potential field 227-1. In some implementations, the potential field is directional (e.g., applicable to parts of the kinematic chains that are located in a certain direction or a certain range of directions from the location of contact) or non-directional (e.g., applicable to all parts of the kinematic chains regardless of their locations relative to the location of contact). In some implementations, the effect of the constraint or the potential is based on a distance from the location of contact to respective parts of the kinematic chains. For example, a part of the kinematic chain that is located at a first distance from the location of contact may be moved further away from its original location and/or the location of contact than another part of the kinematic chain that is located at a second distance, from the location of contact, greater than the first distance. In FIG. 29C, the distal end of the robotic arm 205-2 (e.g., the tip of the robotic arm 205-2 configured to hold a medical tool), which is located close to the location of contact, can be maintained or minimally moved away from the location of contact. Likewise, the proximal end of the robotic arm 205-2 (near the adjustable arm support 210) and other robotic arms 205-1 and 205-3 through 205-6 can remain stationary, while intermediate links and joints between the proximal end and the distal end of the arm can move.

Figure 29D:
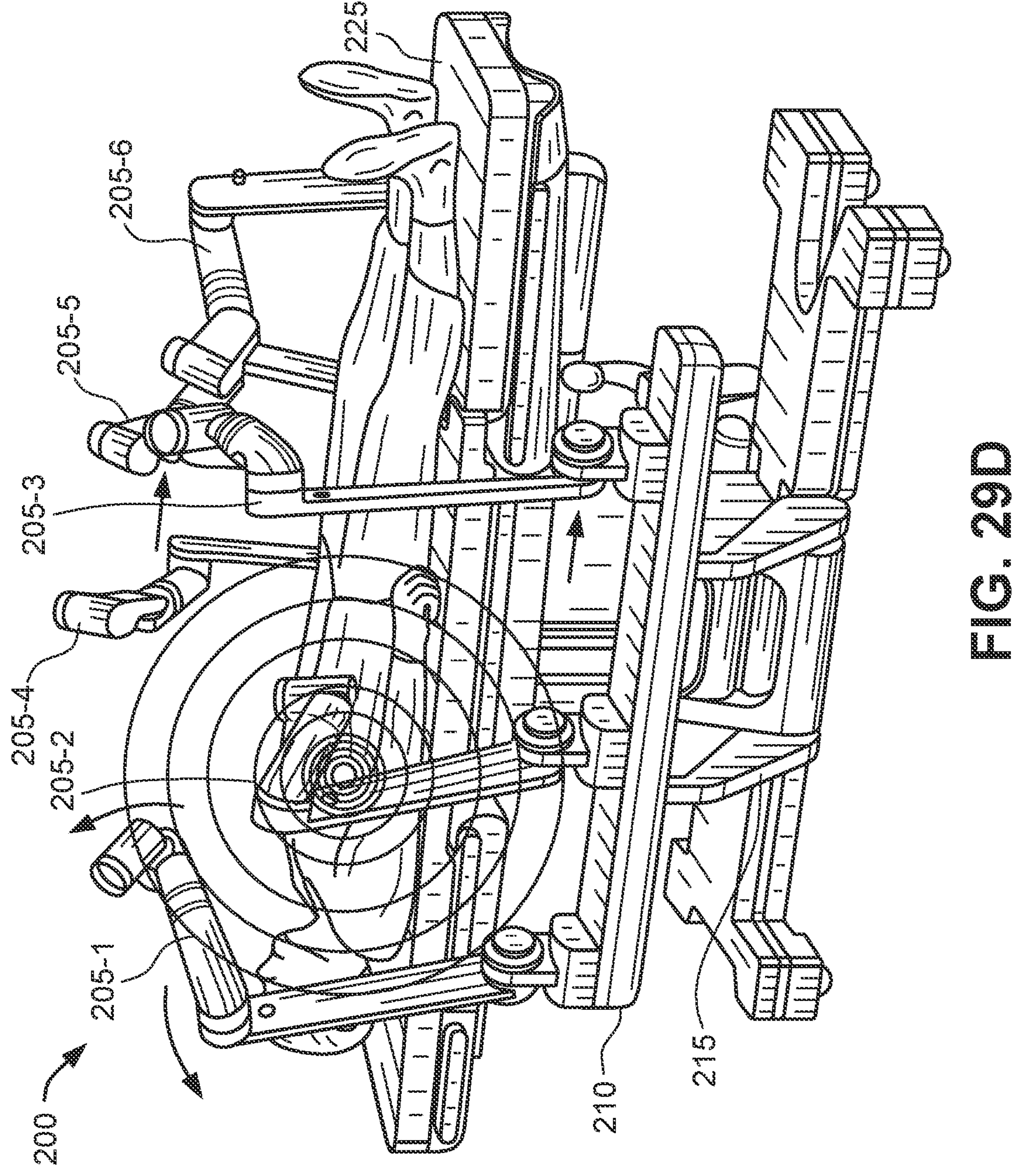

In some implementations, the size of a constraint (e.g., the size of a constrained area or volume) or the range of a potential field is determined based on one or more factors, such as the force detected from the contact, a type of the contact object (e.g., determined based on the location of contact, such as a patient, collision with whom is detected over the table top 225, and a medical personnel, collision with whom is detected outside the table top 225), and a probability of detection. For example, FIG. 29D shows the potential field having a greater range than the potential field shown in FIG. 29C, and configurations of multiple robotic arms, namely robotic arms 205-1 through 205-3, are adjusted (e.g., robotic arms 205-1 and 205-3 and the portions of the robotic arm 205-2 are moved away from the location of contact, or the potential field).

Figure 29E:
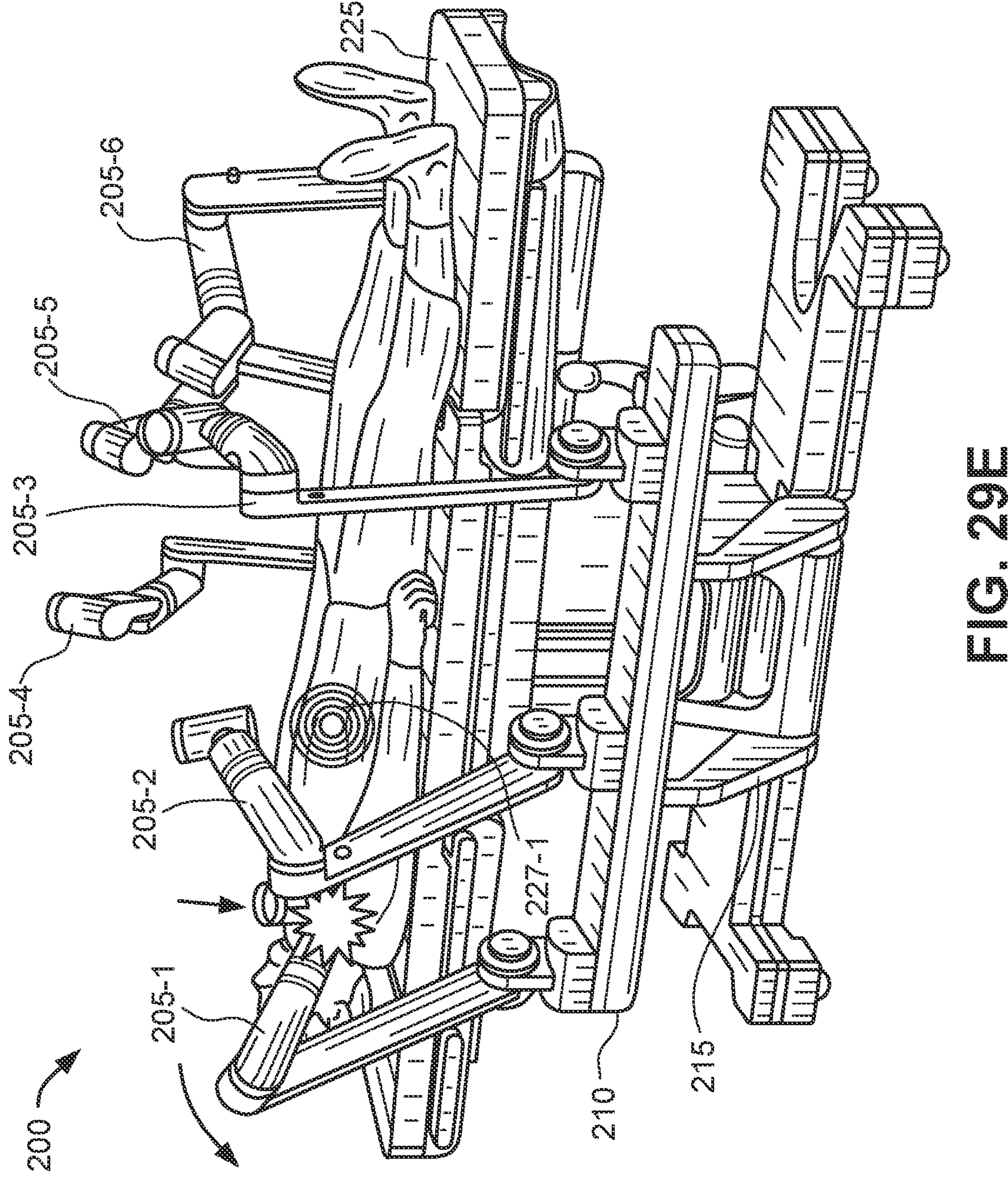
Figure 29F:
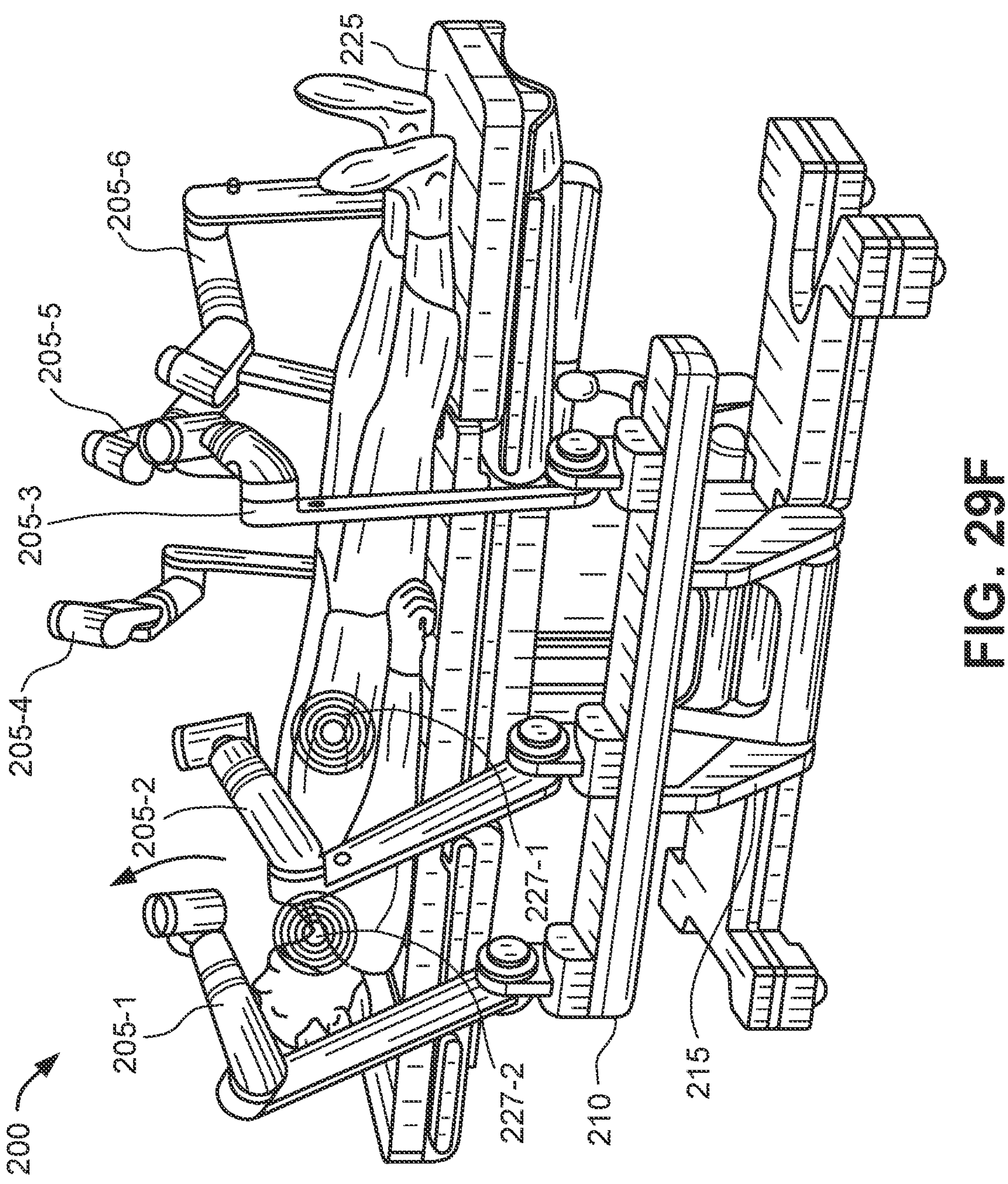

FIG. 29E shows that another collision (or contact) is detected between the robotic arm 205-1 and the patient during a downward movement of the distal end of the robotic arm 205-1. In FIG. 29E, the medical robotic system 200 receives the information about the contact between the robotic arm 205-1 and the patient, models the contact as a potential field 227-2 in the map, and adjusts the configuration of the robotic arm 205-1 (or the configurations of two or more of the robotic arms 205-1 through 205-6, depending on the range of the potential field). FIGS. 29E and 29F also show that the medical robotic system 200 maintains the potential field 227-1 in the map (and as a result, during the adjustment of the configuration of the robotic arm 205-1, the robotic arm 205-1 may not come into the vicinity of the potential field 227-1). In some cases, one or more potential fields (or constraints) expire over time, and thus, the medical robotic system 200 may not maintain the potential field 227-1 by the time the collision between the robotic arm 205-1 and the patient is detected.

FIG. 30 is a flow diagram illustrating a method 330 of adjusting a configuration of a kinematic chain based on contact information in accordance with some embodiments. The method 330 is performed by an electronic device (e.g., one or more processors, such as processors 380 described with respect to FIG. 38) in communication with a medical robotic system that includes a first kinematic chain and one or more sensors positioned to detect one or more parameters (e.g., force, torque, direction of contact, contact location, etc.) of contact with the first kinematic chain (e.g., the medical robotic system 200 with a robotic arm 205 and one or more sensors described with respect to FIGS. 21, 23, 24, and 25A-25D).

In some embodiments, the one or more sensors include at least one of: a force sensor positioned at a base of the first kinematic chain (e.g., at joint 131-3 or at base 136), a force sensor positioned adjacent to a joint between one or more links and an end effector of the first kinematic chain (e.g., at joint 131-1), or one or more contact sensors (e.g., on the shell sensors) on the one or more links (e.g., sensors 321). In some embodiments, the force sensor positioned adjacent to the joint between the one or more links and the robotic arm end effector includes a six-axis load cell.

In some embodiments, the first kinematic chain is kinematically redundant. For example, the first kinematic chain has degrees of freedom higher than those needed to complete for medical tasks (e.g., the first kinematic chain has 7, 8, or 9 degrees of freedom or higher). In some embodiments, the first robotic arm is kinematically redundant. In some embodiments, a combination of the first robotic arm and the adjustable arm support is kinematically redundant.

The method 330 includes (331) receiving (e.g., from the one or more sensors) one or more parameters of contact with the first kinematic chain detected by the one or more sensors.

In some embodiments, the contact with the first kinematic chain includes contact between the first kinematic chain and an object (e.g., a patient, staff, or accessory) that is not part of the medical robotic system.

In some embodiments, the one or more parameters of the contact include (332) one or more selected from a group consisting of: force information of the contact (including force and/or torque), location information of the contact, and direction information of the contact (which may be determined from the movement of the first kinematic chain before and/or during the contact between the first kinematic chain and the object and/or the direction of the force).

In some embodiments, the one or more parameters of contact include information about whether the contact is with a moving or fixed object (which may be determined based on whether a location of the contact changes over time).

The method 330 also includes (333) determining a constraint associated with the first kinematic chain based on the one or more parameters of contact with the first kinematic chain.

In some embodiments, the method 330 includes updating the constraint and/or building a constraint map based on one or more parameters of a subsequent contact with the first kinematic chain detected by the one or more sensors. For example, the medical robotic system 200 creates the constraint map (e.g., based on initial information of contact) or updates a previously built constraint map (e.g., based on subsequent information of contact).

In some embodiments, the one or more parameters of contact form part of a probabilistic map. For example, contact information is converted into probabilities that a certain object may be present at respective locations in a three-dimensional space (and hence, the probability values in the probabilistic map represents a likelihood of a contact or collision for respective locations or voxels).

In some embodiments, the probabilistic map is determined based on the confidence of detection of a contact. For example, an object (or a contact) having a high confidence of detection may be assigned a high probability value, because the object has a high likelihood of being present at the corresponding location, and an object (or a contact) having a low confidence of detection may be assigned a low probability value, because the object has a low likelihood of being present at the corresponding location.

In some embodiments, the method 330 includes updating the probabilistic map based on a finite time of constraint. For example, the medical robotic system 200 may update the probabilistic map at one or more time intervals. In some implementations, updating the probabilistic map based on a finite time of constraint includes expiring (or removing) one or more constraints after a certain period of time since such constraints were last updated in the probabilistic map. This prevents stale constraints from remaining on the probabilistic map, thereby interfering with determination of the optimal configuration for the first kinematic chain.

In some embodiments, the method 330 includes updating the probabilistic map based on a changing probability of constraint. In some implementations, the medical robotic system 200 determines whether a contact was made with a stationary object or a dynamic, moving object (e.g., based on a contact location, for example, a contact outside the table top 225 may be modeled as a contact with a moving object, and a contact over the table top 225 may be modeled as a contact with a stationary object). For a contact with a dynamic object, the probability is reduced based on the likelihood that the dynamic object may not remain in the same location. For example, a time decay function (or curve) may be used to update the probabilistic map, where the time decay function may be a linear decay function or a nonlinear decay function (e.g., an exponential decay function).

In some embodiments, the constraint is modeled (334) as a potential field (e.g., potential field 227-1) based at least in part on the one or more parameters of contact detected by the one or more sensors. For example, the potential field is modeled as one or more locations from which force is applied on one or more components of the first kinematic chain (and possibly on components of other kinematic chains). In some embodiments, a modeled force on a respective component of the first kinematic chain due to the potential field is based on a distance from a location of contact to a position of the respective component and may have a direction facing away from the location of collision.

In some embodiments, the potential field is also based (335) on a probability of detecting a contact by a respective sensor of the one or more sensors. For example, the modeled force is increased for a contact detected by a sensor having a high reliability/fidelity of detection (e.g., a sensor having a low sensitivity), and the modeled force is reduced for a contact detected by a sensor having a low reliability/fidelity of detection (e.g., a sensor having a high sensitivity). This reduces the likelihood of a contact with an object that is difficult to detect (e.g., due to the size or the material of the object) while increases the space available for robotic arms and tools to maneuver by reducing the force for an object that can be reliably and accurately detected. In some embodiments, the respective sensor of the one or more sensors is assigned with a predefined probability of detection (e.g., the medical robotic system 200 stores in memory a table of predefined probability-of-detection values for respective sensors or respective sensor types).

In some embodiments, the constraint is modeled as a no-entry zone (e.g., a volume which no components of the first kinematic chain are permitted to enter). In some embodiments, the no-entry zone has one or more boundaries defined based on the one or more parameters of contact (e.g., the size of the no-entry zone is determined based on the force information and the shape of the no-entry zone is determined based on the direction information and/or the location information).

The method 330 further includes (336) causing adjustment (e.g., by activating one or more actuators coupled with, or included in, the first kinematic chain) of a configuration of the first kinematic chain from a first configuration to a second configuration (e.g., the second configuration is distinct from the first configuration) based on the constraint. The adjustment positions the first kinematic chain in a non-collision position and reduces the risk of future collision.

In some embodiments, the first kinematic chain includes a first robotic arm (e.g., robotic arm 205-1) and an adjustable arm support (e.g., adjustable arm support 210) on which the first robotic arm is positioned (e.g., the first robotic arm is mechanically coupled—such as rotatably coupled—with the adjustable arm support), and adjustment of the configuration of the first kinematic chain includes (337) changing a position of the adjustable arm support.

In some embodiments, the method includes (338) utilizing a null space of the first kinematic chain causing adjustment of the configuration of the first kinematic chain from the first configuration to the second configuration.

In some embodiments, the method 330 includes causing adjustment of configurations of one or more other kinematic chains not in contact with one or more portions of the first kinematic chain based on the constraint determined from the one or more parameters of contact with the first kinematic chain detected by the one or more sensors (e.g., as shown in FIG. 29D, robotic arms 205-1 and 205-3 are moved even though robotic arms 205-1 and 205-3 that are not in contact with the robotic arm 205-2).

In some embodiments, the method 330 includes causing adjustment of configurations of one or more kinematic chains not in contact with the object based on the constraint determined from the one or more parameters of contact with the first kinematic chain detected by the one or more sensors (e.g., as shown in FIG. 29D, robotic arms 205-1 and 205-3 that are not in contact with the patient are moved).

In some embodiments, the method 330 further includes performing a medical procedure. In some embodiments, the medical procedure includes a surgical procedure.

C. Sensor Architecture for Detecting Objects in the Vicinity

As described above, the medical robotic system 200 may include one or more sensors for detecting contact with kinematic chains (e.g., robotic arms). In some embodiments, the medical robotic system 200 includes one or more sensors (e.g., non-contact, proximity sensors) for detecting objects in the vicinity of the medical robotic system 200. Such sensors do not require contact, and thus, may be used to adjust the configurations (or movements) of the kinematic chains and prevent contact before the contact occurs. Examples of such sensors include sonar, radar, LIDAR, ultrasound sensors, light-based sensors, or vision-based sensors.

Figure 31:
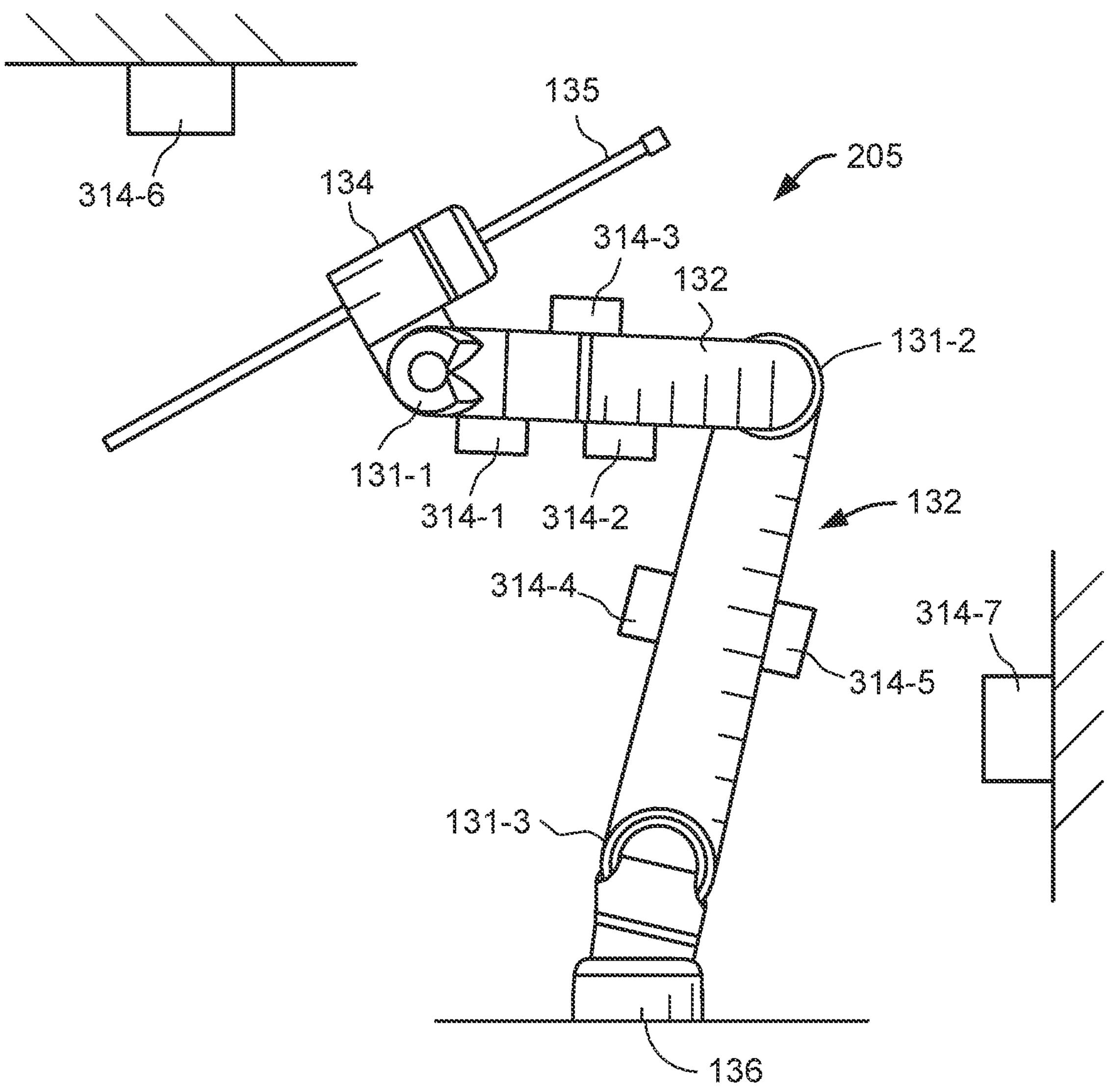
FIG. 31 shows sensors mounted for detecting objects in a vicinity in accordance with some embodiments.

FIG. 31 shows sensors 314 mounted for detecting objects in the vicinity in accordance with some embodiments. In some embodiments, one or more sensors (e.g., sensors 314-1 through 314-5) are fixed to one or more of the robot links 132. In some embodiments, one or more sensors (e.g., sensors 314-6 and 314-7) are fixed externally to the medical robotic system 200 (e.g., on a wall or ceiling). In some cases, the one or more sensors 314 can serve as a reference point for gathering information about a dynamic environment. In some embodiments, the one or more sensors 314 are located on any of the links or joints between links that have the most visibility to an object (e.g., a patient). In some embodiments, at least one robotic arm has one sensor. In some embodiments, at least one robotic arm has multiple sensors.

Figure 32:
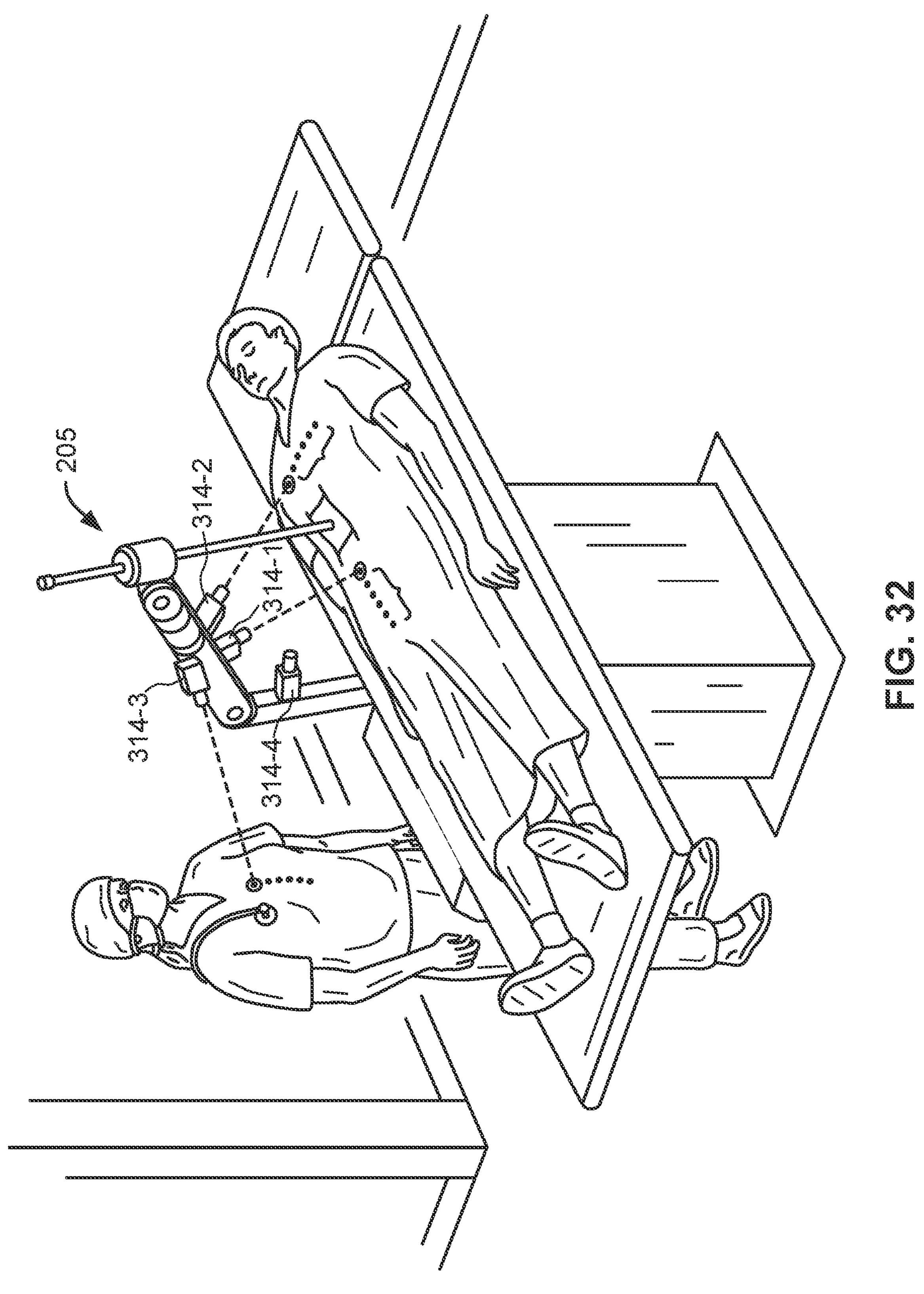
FIG. 32 shows an example of a robotic arm with multiple sensors to gather information regarding a dynamic environment.

FIG. 32 shows an example of a robotic arm 205 with multiple sensors 314 to gather information regarding a dynamic environment. In FIG. 32, the robotic arm 205 includes at least four sensors (although the robotic arm 205 may include additional sensors, four sensors 314-1 through 314-4 are shown in FIG. 32). The three sensors 314-1 through 314-3 are positioned on a distal link of the robotic arm 205, while one sensor 314-4 is positioned on a proximal link of the robotic arm 205. As illustrated in FIG. 32, the different sensors 314 may be configured to detect different patches or regions of the environment. Sensors 314-1 and 314-2 detect different regions of the patient, sensor 314-3 detects a medical staff (e.g., a physician assistant, nurse, anesthesiologist, etc.), while sensor 314-4 does not detect anything. From the information detected by the sensors 314, a map of the environment can be generated.

Figure 33:
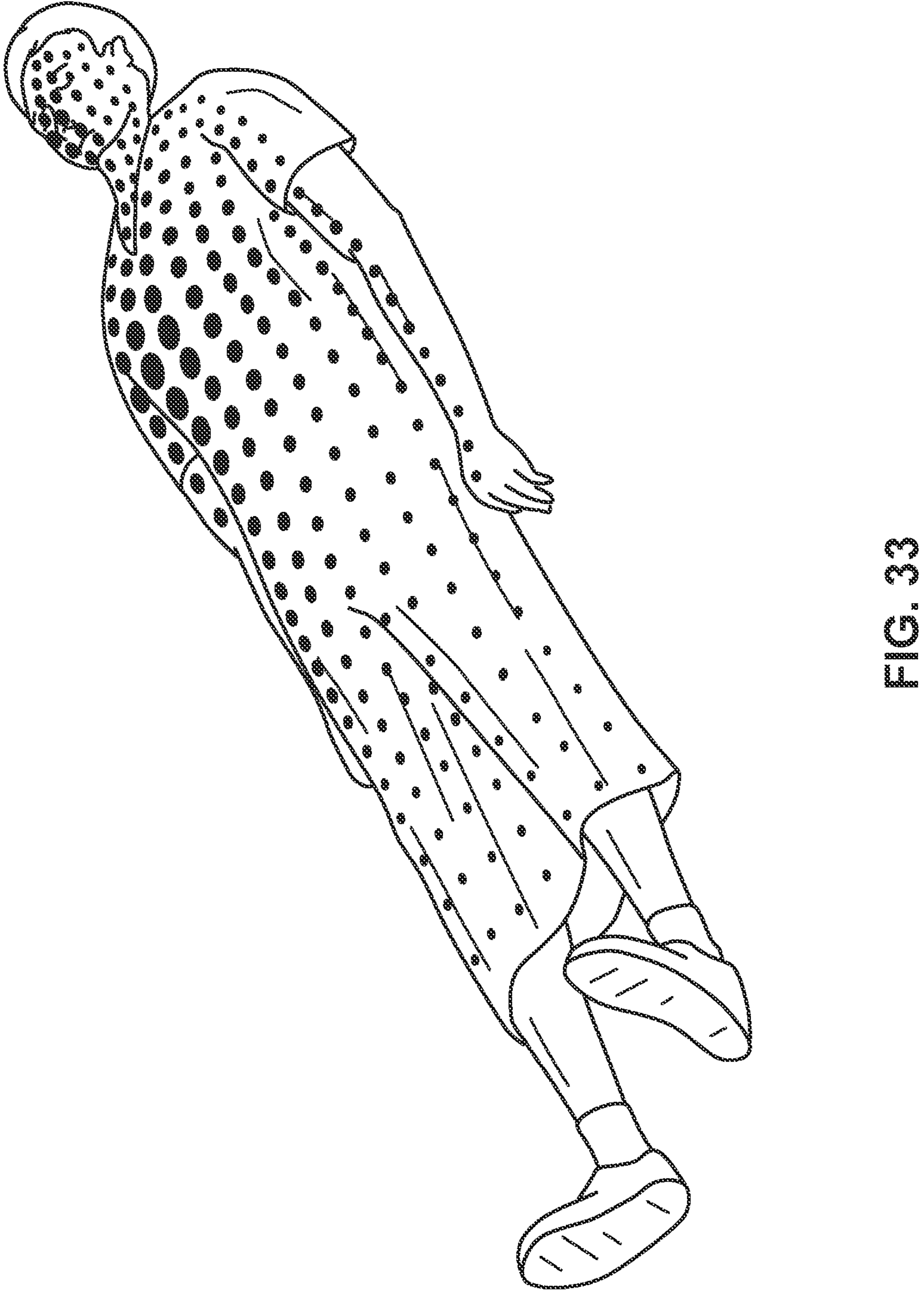
FIG. 33 illustrates an example representation of a human with a corresponding map based on information detected by one or more sensors in accordance with some embodiments.

FIG. 33 illustrates an example representation of a human (e.g., a patient) with a map based on information detected by one or more sensors 314 (or a single sensor) in accordance with some embodiments. In FIG. 33, the human is represented as a point cloud (e.g., a group of points or dots) in a three-dimensional space (e.g., each point is associated with a three-dimensional coordinate). In some embodiments, each point has a probability value indicating the likelihood that the point belongs to a particular object (e.g., the patient). In FIG. 33, the probability value is represented based on the size of the point (e.g., a bigger point represents a higher probability that the point belongs to the object).

D. Utilization of Sensed Information to Generate a Map of Sensed Objects

Figure 34:
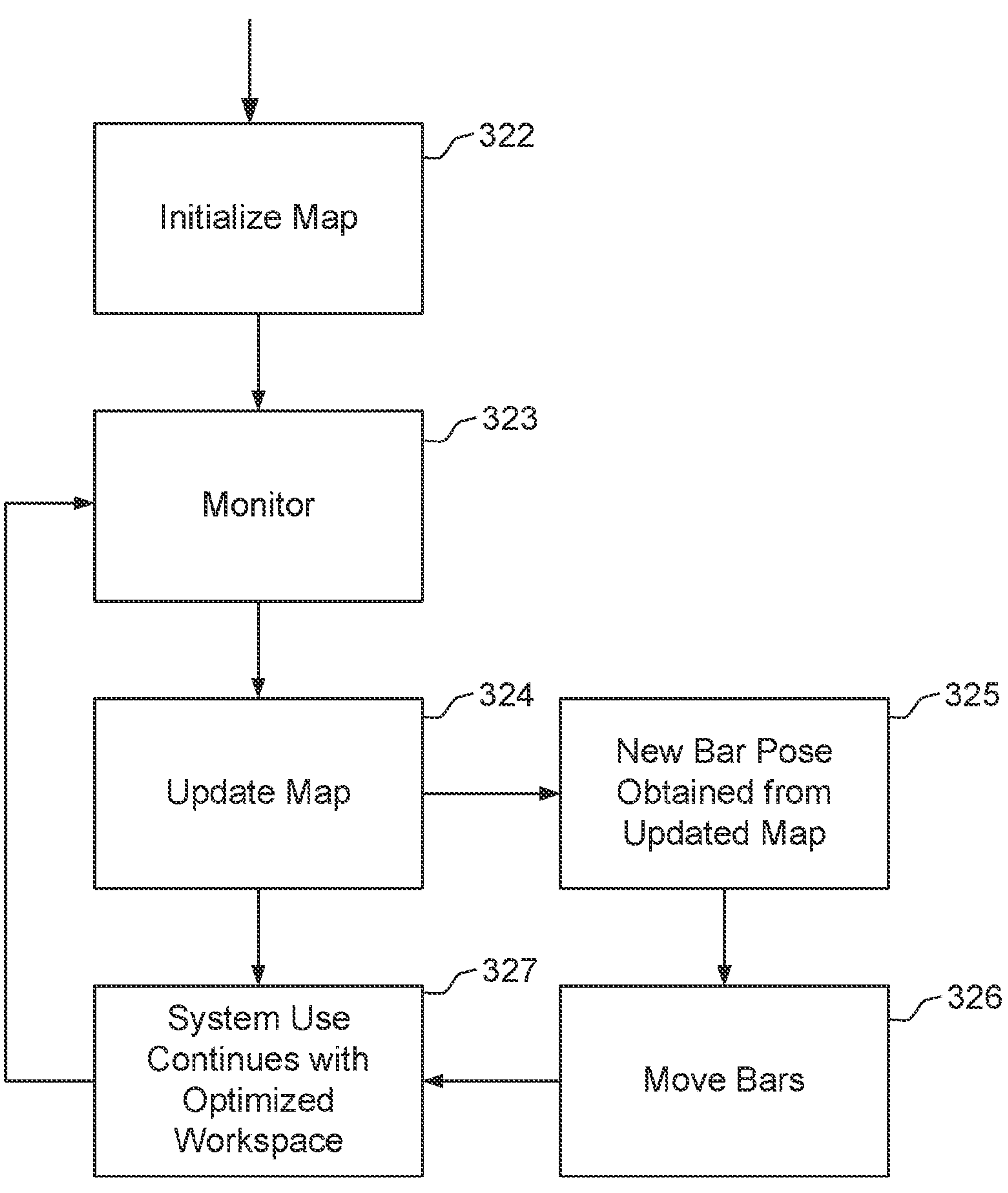
FIG. 34 is a flow diagram illustrating a method for adjusting one or more kinematic chains based on detected object information in accordance with some embodiments.

FIG. 34 is a flow diagram illustrating a method for adjusting one or more kinematic chains based on detected object information in accordance with some embodiments.

The workflow shown in FIG. 34 starts with (operation 322) map initialization. In some implementations, the map initialization includes using an empty map. In such cases, the medical robotic system assumes no a priori knowledge of the environment (e.g., locations and sizes of objects). In some other implementations, the map initialization includes selection of an initial patient body map from a predetermined model (spatial, statistical or deterministic, in the form of a grid or point cloud) of the patient's body model. In such cases, the map is initialized with a patient body map (e.g., a default patient body map or a patient body map that is selected or generated based on user input). For example, the patient body map may be generated based on body measurements of the patient (e.g., height and waist circumference, etc.). In some implementations, the initial patient body map has an empty surrounding around the modeled patient body.

A medical procedure starts and the medical robotic system (operation 323) monitors the environment, and (operation 324) updates the map with information about detected objects. For example, as the robotic arms move, the sensors will record their distances to the closest object in sight. In some implementations, the medical robotic system determines whether the detected object belongs to the medical robotic system or not. If the detected object does not belong to the medical robotic system 200, and the object is within the medical procedure, the initial spatial/statistical or deterministic model (or map) is updated. The update could be based on any simultaneous localization and mapping (SLAM) algorithms or sensor fusion algorithm, such as Kalman filter, particle filter, and covariance intersection algorithms. The update operation (operation 324) is repeated periodically. After a number of iterations, a spatial model of the environment (e.g., including the patient body) with high confidence may be achieved.

The robot processor will avoid collision with this model when the confidence and the accuracy of the model is high enough. This will eliminate the possibility of collision with the patient. The bar placement can be also modified during operation based on this model to increase the efficiency (less arm-arm collisions, etc.).

In some cases, new configurations of the kinematic chains are determined (operation 325) based on the updated map, and the medical robotic system (operation 326) places the kinematic chains in the determined configurations. The medical procedure continues while the kinematic chains are in optimized configurations. As a result, the likelihood of the kinematic chains coming into contact with another object is reduced. This, in turn, increases the efficiency of the medical procedure, as there will be less collision (e.g., between the robotic arms or between a robotic arm and another object).

In some implementations, due to the dynamic nature of the environment, each patch of boundary can be assigned with a probability based on when and how the patch of boundary was detected (e.g., the medical robotic system stores information indicating when and how information about a particular point was detected, such as a timestamp of the detection). For example, in accordance with a determination that the patch was determined with a high contact force (or with a sensor with a high sensitivity), the medical robotic system assigns a high probability to the detected boundary of the object. In addition, the medical robotic system decreases the probability over time, to reflect the fact that object might have moved from its original location, thus, invalidating the boundary that was detected a long time ago. On the other hand, if an object continues to be detected at a same or similar location over time, the medical robotic system increases the probability assigned to the detected boundary of the object. In such cases, the location and shape of the object (or the boundary thereof) may be approximated with better accuracy. In some implementations, additional prior knowledge may be used. For example, a patient is known to be relatively fixed to the table top, whereas staff generally move around outside the bed. Thus, based on the location of the sensor measurement, separate models may be generated (e.g., a patient model based on sensor measurements for the table top area and a staff model based on sensor measurements outside the bed, which may expire or decay over time).

FIGS. 35A-35G illustrate configurations of robotic arms and corresponding maps in accordance with some embodiments. In FIGS. 35A-35G, sensors are not shown so as not to obscure other aspects of the operations of the medical robotic system.

FIG. 35A illustrates, on the left side, a medical robotic system with robotic arms 205-1 and 205-2, where a patient 240 is positioned on a table top 225. FIG. 35A also shows a ceiling structure 291 (e.g., lighting fixture). Shown on the right side of FIG. 35A is a graphical representation of an object map that corresponds to the setting shown on the left side of FIG. 35A. The object map includes a map 241 of the patient (e.g., a group of points representing a surface boundary of the patient) and also includes a map of one or more portions of the table top 225 and the ceiling structure 291.

FIG. 35B illustrates, on the left side, that the robotic arm 205-2 moves based on the map 241 of the patient (e.g., to a more optimal position or pose). FIG. 35B also shows, on the left side, a medical personnel 242 has moved into the vicinity of the robotic arm 205-1. Shown on the right side of FIG. 35B is a graphical representation of an updated object map that includes a map 243 of the medical personnel 242.

FIG. 35C illustrates, on the left side, that the robotic arm 205-1 moves based on the updated map, including the map 243 of the medical personnel.

FIG. 35D illustrates, on the left side, that the medical personnel 242 has moved away from the robotic arm 205-1. However, FIG. 35D shows, on the right side, that the map 243 of the medical personnel remains (at least for a certain period of time).

FIG. 35E illustrates, on the right side, that the map 243 of the medical personnel has been removed. In some implementations, the map 243 of the medical personnel (or any moving object) expires after a certain period of time (e.g., a map of the moving object is removed upon lapse of a preset time period). In some other implementations, the map 243 of the medical personnel (or any moving object) decays over time (e.g., the probability values for the map of the moving object decrease over time). On the other hand, the patient 240 continues to be detected over time at the same location. In some implementations, the probability values for the map of a static object (e.g., the patient 240) increase over time.

FIG. 35F illustrates, on the left side, that the medical personnel 242 has moved into the vicinity of the robotic arm 205-2. Shown on the right side of FIG. 35F is a graphical representation of another updated object map that includes the map 243 of the medical personnel 242 on the right side of the patient 240.

FIG. 35G illustrates, on the left side, that the robotic arm 205-2 moves based on the updated map, including the map 243 of the medical personnel at the new location.

As shown in FIGS. 35A-35G, the medical robotic system can detect objects in the vicinity of the medical robotic system and adjust configurations of the kinematic chains so that the risk of collision with the kinematic chains is reduced. FIGS. 35A-35G also show that certain objects are modeled differently in the map. For example, a map of a moving object may expire or decay over time, and probability values of a static object may increase over time (or upon reaching a threshold time).

Figure 36A:
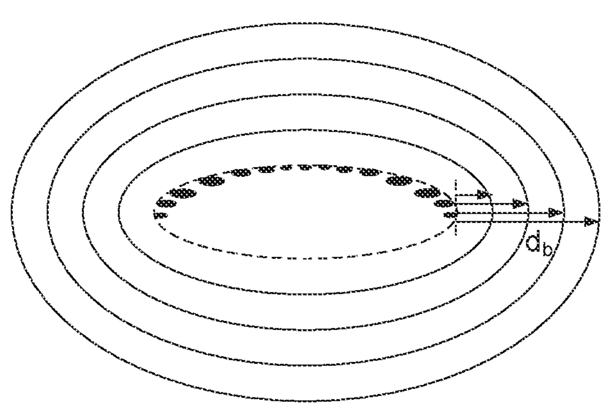
FIGS. 36A and 36B are schematic diagrams illustrating buffer zones in accordance with some embodiments.
Figure 36B:
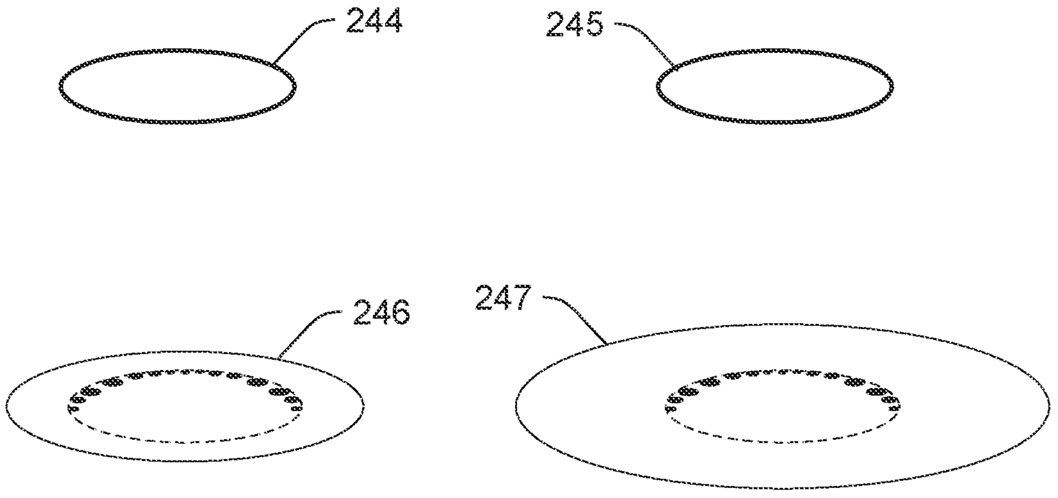

In some embodiments, an object is modeled with a buffer zone in the map. Allowing a kinematic chain to move right up next to the boundary of an object may cause the kinematic chain to come into contact with the object due to various reasons, such as measurement errors, modeling errors, and movement of the object, and providing a buffer zone (e.g., a certain area or volume with a boundary having a certain distance from the boundary of the object) reduces the likelihood of a contact between the kinematic chain and the object. In some embodiments, a buffer distance db for the buffer zone is determined based on various factors (e.g., a probability of detection, a confidence of detection, etc.), as shown in FIG. 36A. For example, for two objects 244 and 245 that have the same physical size (and shape), their buffer zones 246 and 247 may have different sizes when the object 244 is a static object and the object 245 is a dynamic, moving object.

FIG. 37 is a flow diagram illustrating a method 370 of adjusting a configuration of a robotic arm based on sensor information in accordance with some embodiments. The method 330 is performed by an electronic device (e.g., one or more processors, such as processors 380 described with respect to FIG. 38) in communication with a medical robotic system that includes a first robotic arm and one or more sensors positioned to detect objects within a vicinity of the first robotic arm (e.g., the medical robotic system 200 with a robotic arm 205 and one or more sensors described with respect to FIG. 31).

In some embodiments, the one or more sensors include at least one or more of: sonar, radar, LIDAR, ultrasound, light-based sensors, or vision-based sensors.

In some embodiments, the one or more sensors include at least one non-contact sensor. In some embodiments, the one or more sensors include at least one contact sensor in addition to the at least one non-contact sensor.

In some embodiments, the first robotic arm is teleoperatively controlled. In some embodiments, the stored instructions, when executed by the one or more processors, cause the one or more processors to receive control signals from an input device that is located separately from the one or more processors. In some embodiments, the input device is located separately from the first robotic arm, or any other robotic arms.

In some embodiments, the first robotic arm is kinematically redundant. For example, the first robotic arm has degrees of freedom higher than those needed to complete for medical tasks (e.g., the first robotic arm, with or without an associated adjustable arm support, has 7, 8, or 9 degrees of freedom or higher).

In some embodiments, the medical robotic system includes a movable patient platform. In some embodiments, the movable patient platform includes a rigid base and a table top that is movable relative to the rigid base.

The method 370 includes (371) receiving, from the one or more sensors, sensor information corresponding to positions of one or more objects that are present within a vicinity of the first robotic arm (e.g., at a first time).

The method 370 also includes (372) generating or updating an object map (e.g., a data structure that indicates positions and/or sizes of objects adjacent to the medical robotic system, in particular the first robotic arm) based on the sensor information, wherein the object map characterizes spatial relationships of objects within a vicinity of the first robotic arm. In some embodiments, the object map characterizes spatial relationships of objects adjacent to the medical robotic system. By utilizing multiple sensors, it is possible to detect an object past occlusions. For example, an object may be located behind an obstacle within a field of view of a particular sensor. However, the object may be detected by one or more other sensors viewing the object from different angles. Thus, by utilizing multiple sensors, objects can be detected and their positions can be determined even if there are obstacles occluding the objects from certain views.

The method 370 further includes (373) adjusting a configuration of the first robotic arm from a first configuration to a second configuration (e.g., the second configuration is distinct from the first configuration) based on the object map. The adjustment of the configuration of the first robotic arm reduces the risk of collision between the first robotic arm and the detected objects.

In some embodiments, the medical robotic system includes one or more robotic arms other than the first robotic arm; and one or more second sensors positioned to detect presence of objects within a vicinity of the one or more robotic arms. The method 370 further includes receiving, from the one or more second sensors, second sensor information corresponding to one or more positional locations of one or more objects (e.g., the same objects represented in the first sensor information and/or different objects) that are within a vicinity of the one or more robotic arms; generating or update the object map based also on the second sensor information; and adjusting configurations of the one or more robotic arms based on the object map.

In some embodiments, the method 370 includes, subsequent to generating or updating the object map, (374) iterating: receiving, from the one or more sensors, subsequent sensor information corresponding to positions of one or more objects that are within a vicinity of the first robotic arm; updating the object map based on the subsequent sensor information; and adjusting the configuration of the first robotic arm in accordance with the object map that is updated based on the subsequent sensor information.

In some embodiments, the method 370 optionally includes (375) updating the object map based on a probability of detecting a respective object of the one or more objects. For example, an object that has a low probability of detection (e.g., an object that is detected with a frequency below a threshold frequency and thus less likely to be detected) is modeled with a buffer area to reduce the probability of collision with the object and an object that has a high probability of detection (e.g., an object that is detected with a frequency above a threshold frequency and thus more likely to be detected) is modeled with no buffer area or a smaller buffer area.

In some embodiments, the one or more objects include an object that moves dynamically. For example, the object is located at a first position at a first time and at a second position different from the first position at a second time different from the first time. The dynamically moving object may be a patient, staff, or accessory. In some embodiments, the object moves dynamically (e.g., the object changes its position based on the configuration of the first robotic arm, or any other robotic arm) based on a configuration (e.g., kinematic information) of the medical robotic system. For example, the object is a patient whose position changes based on a configuration of a patient platform (e.g., a surgical bed). In other embodiments, the object is a bed side staff that is trying to get out of the way of a robotic arm while it is in motion. In some embodiments, the method further includes (376) removing the update to the object map (or updating the object map to reduce or eliminate the effect of the object on the object map or removing the object from the object map) after a period of time after the object map has been updated to reflect the object. For example, if an object is detected at location A, the area near location A would be marked in the object map. After sometime, the area around location A is no longer marked in the object map. This does not apply to an object that remains at the same location. For example, the one or more processors forgo removing the update to the object map or maintain the object in the object map in accordance with a determination that the object continues to be detected (e.g., around the same location).

In some embodiments, adjusting the configuration of the first robotic arm increases a distance between the first robotic arm and the dynamic object so that a risk of collision between the first robotic arm and the dynamic object is reduced.

In some embodiments, the one or more objects include a static object. In some embodiments, the method 370 includes maintaining the static object in the object map (or maintain the update to the object map involving the static object) in accordance with continuing to detect, based on sensor information, the static object (e.g., around the same location).

In some embodiments, the method 370 includes (377) updating the object map also based on a configuration (e.g., kinematic information) of the medical robotic system (e.g., configuration of the first robotic arm and/or any other robotic arms).

In some embodiments, the method 370 further includes performing a medical procedure. In some embodiments, the medical procedure includes a surgical procedure.

E. Determination of a Configuration

As described above, the medical robotic system determines a new configuration of a kinematic chain based on sensor information (e.g., contact information and/or detected object information). There are certain conditions for the new configuration, such as a ADM 134 of the robotic arm 205 and/or a remote center of motion (RCM) coupled thereto kept in a static pose/position, while the distance between a respective kinematic chain and the detected object and the distance between any two kinematic chains need to be increased (so as to reduce the likelihood of contact and provide an increased workspace to maneuver the kinematic chains). While there are many ways to determine the new configuration based on these conditions, one way to determine the new configuration is based on a cost function (also called a loss function). For example, a cost function may include penalties or points based on the conditions for the new configuration and the new configuration is selected based on parameters (e.g., positions of respective components of the kinematic chain) that minimize or maximize the cost function.

In some implementations, in order to maximize the workspace of the medical robotic system, the following optimization process may be performed. While maintaining remote center positions of each robotic arm, the goal is to maximize the minimum distance of joint positions to respective joint limits (which leaves more travel to the joint limits, thereby reduces the likelihood of any joint reaching its joint limit) and the minimum distance of any two robotic arms (which reduces the likelihood of collision between two robotic arms). Assuming six robotic arms in total, with first through third robotic arms on one base and fourth through sixth robotic arms on another base, a cost function can be written as follows:

$$f(T_{base,1}, T_{base,4}) = \min_j\left(\min_i(w_{i,j}\cdot\min(q_{i,j}-q_{i,j,min},\ q_{i,j,max}-q_{i,j}))\right)+\sum_{m\neq n} v_{m,n} d^2(j_m, j_n) \tag{1}$$

where qi,j is the position for joint i of robotic arm j, qij,min is the lower bound limit for joint i of robotic arm j, qij,max is the upper bound limit for joint i of robotic arm j, wi,j and vm,n are weights selected for particular applications, Tbase,j is a homogeneous (e.g., 4×4) matrix representing the base pose of robotic arm j, and d(j1,j2) is the minimal distance between two robotic arms j1 and j2, which is the minimal distance of any two links on each robotic arm. The optimization problem is to find Tbase,1 and Tbase,4 to maximize the cost function, which is mathematically expressed as follows:

$$\max f(T_{base,1},T_{base,4}),\ s.t.,\dot{p}_{rc,j}(q_j,T_{base,j})=0\ j=1,\ldots,6 \tag{2}$$

where qj is the vector for all joint positions of robotic arm j, and prc,j(qj,Tbase,j) is the position of the remote center of robotic arm j as a function joint positions and base pose of robotic arm j.

If the magnitude of contact, either force or torque or both, is known and used, the optimization may be performed as an online process, such that the improvement in contact reduction can be measured during the optimization. The following modified cost function may be used:

$$f_{mag}(T_{base,1}, T_{base,4}) = f(T_{base,1}, T_{base,4}) - \sum_{i,j}(w_F\cdot|F_{i,j}| + w_T\cdot|T_{i,j}|) \tag{3}$$

where Fi,j and Ti,j are the measured external contact force and moment on link i of robotic arm j, wF and wT are weights selected for particular applications. In this case, the optimization problem is to find Tbase,1 and Tbase,4 to maximize the cost function, which is mathematically expressed as follows:

$$\max f_{mag}(T_{base,1},T_{base,4})\ s.t.,\dot{p}_{rc,j}(q_j,T_{base,j})=0\ j=1,\ldots,6 \tag{4}$$

To enable offline optimization, additional information of coarse contact location and contact direction can be utilized to estimate the location of an object so that an estimated distance between the robotic arm and the object can be calculated.

When the coarse location is to be used without the direction information for the contact, assume a contact with magnitudes of |Fi,j| and |T,ij| are detected on link i of robotic arm j, the location of the object can be estimated to be min(kF/|Fi,j|, kT/|Ti,j|) away from the contacting link along its perpendicular bisector, which is noted as Oi,j. The distance between the contacting link and the object can be estimated as ri,j(qj). For a link that no contact has been detected ri,j(qj)=0. A new cost function that also accounts for the contact distances is as follows:

$$f_{loc}(T_{base,1}, T_{base,4}) = f(T_{base,1}, T_{base,4}) + w_r\cdot\sum_{i,j} r_{i,j}^2(q_j) \tag{5}$$

where wr is the weight selected for particular applications. In this case, the optimization problem is to find Tbase,1 and Tbase,2 to maximize the cost function, which is mathematically expressed as follows:

$$\max f_{loc}(T_{base,1},T_{base,4}),\ s.t.,\dot{p}_{rc,j}(q_j,T_{base,j})=0\ j=1,\ldots,6 \tag{6}$$

When the contact direction information is available along with the coarse contact location, more accurate object location can be estimated. With the contact direction information, the object position O'i,j can be estimated as veci,j+kF·Fi,j/|Fi,j|2, where veci,j is obtained from $T_{i,j}=vec_{i,j}\times F_{i,j}$.

Then the distance between the contacting link and the object can be estimated similarly as described above. The estimated distance is noted as $r'_{i,j}(q_i)$. In some implementations, the angle between the contact direction and the lengthwise link direction toward 90° for a link on a rotary joint needs to be included in the optimization. For contact detected on link i of robotic arm j along $dir_{i,j}$, and the lengthwise link direction is which is a function of $q_j$, the angle between the two direction vectors $\theta_{i,j}(q_i)=\arccos(dir_{i,j}\cdot link_{i,j})$. A new cost function that also accounts for the direction of contact is as follows:

$$f_{dir}(T_{base,1}, T_{base,4}) = f(T_{base,1}, T_{base,4}) + w_r\cdot\sum_{i,j}\left(r'_{i,j}(q_{i,j})\right)^2 - w_\theta\cdot\sum_{i,j}(\theta_{i,j}(q_j)-90°)^2 \tag{7}$$

where $w_\theta$ is a weight selected for particular applications. In this case, the optimization problem is to find $T_{base,1}$ and $T_{base,4}$ to maximize the cost function, which is mathematically expressed as follows:

$$\max f_{dir}(T_{base,1},T_{base,4}),\ s.t.,\dot{p}_{rc,j}(q_j,\ T_{base,j})=0\ j=1,\ldots,6 \tag{8}$$

3. Implementing Systems and Terminology.

Figure 38:
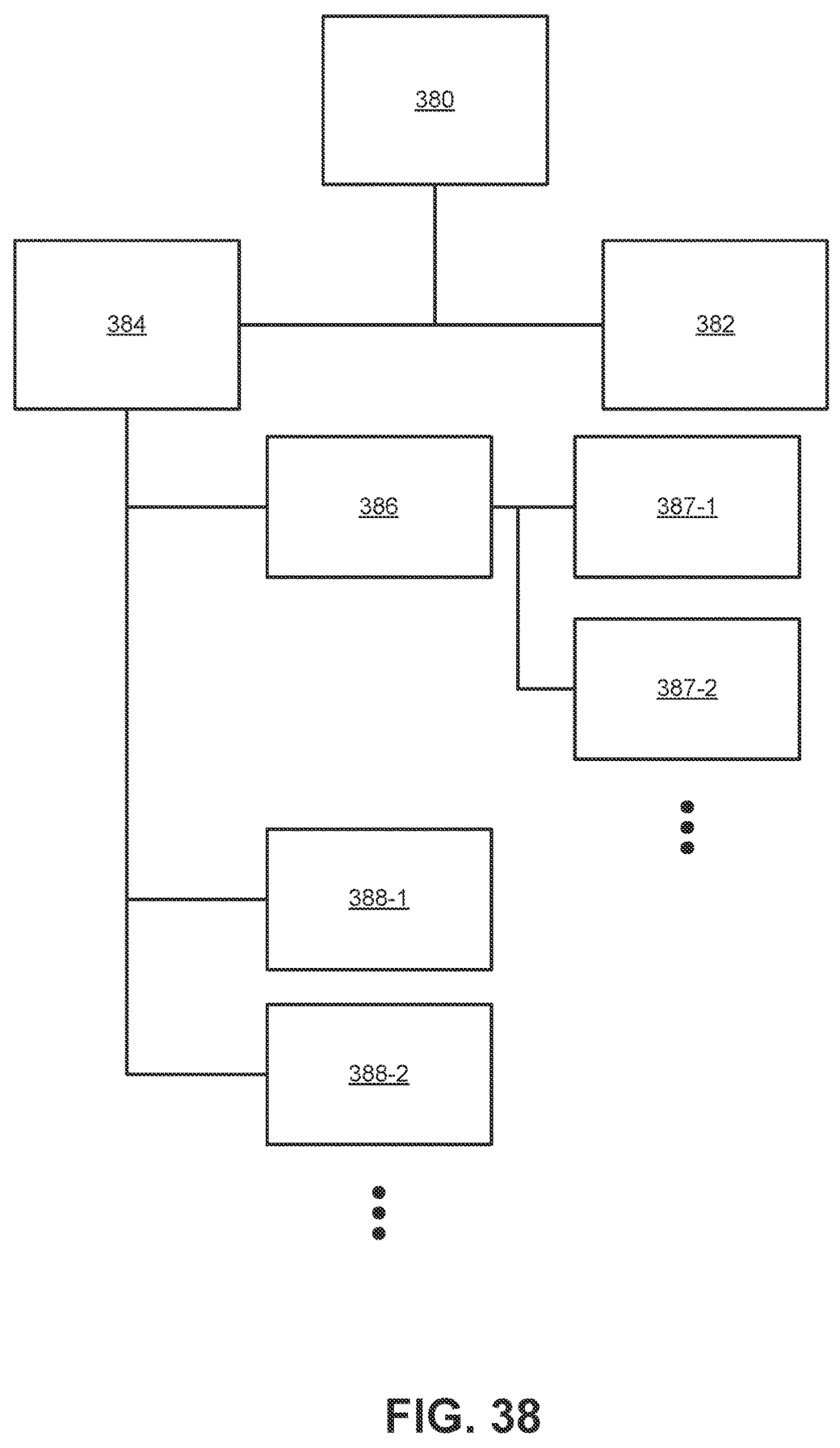

FIG. 38 is a schematic diagram illustrating electronic components of a medical robotic system in accordance with some embodiments.

The medical robotic system includes one or more processors 380, which are in communication with a computer readable storage medium 382 (e.g., computer memory devices, such as random-access memory, read-only memory, static random-access memory, and non-volatile memory, and other storage devices, such as a hard drive, an optical disk, a magnetic tape recording, or any combination thereof) storing instructions for performing any methods described herein (e.g., operations described with respect to FIGS. 30 and 37). The one or more processors 380 are also in communication with an input/output controller 384 (via a system bus or any suitable electrical circuit). The input/output controller 384 receives sensor data from one or more sensors 388-1, 388-2, etc., and relays the sensor data to the one or more processors 380. The input/output controller 384 also receives instructions and/or data from the one or more processors 380 and relays the instructions and/or data to one or more actuators, such as first motors 387-1 and 387-2, etc. In some embodiments, the input/output controller 384 is coupled to one or more actuator controllers 386 and provides instructions and/or data to at least a subset of the one or more actuator controllers 386, which, in turn, provide control signals to selected actuators. In some embodiments, the one or more actuator controller 386 are integrated with the input/output controller 384 and the input/output controller 384 provides control signals directly to the one or more actuators 387 (without a separate actuator controller). Although FIG. 38 shows that there is one actuator controller 386 (e.g., one actuator controller for the entire mobile medical platform, in some embodiments, additional actuator controllers may be used (e.g., one actuator controller for each actuator, etc.).

Implementations disclosed herein provide systems, methods and apparatus for medical robotic systems that can optimize configurations of kinematic chains based on positions of objects in a vicinity of the kinematic chains.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions for power-assisted mobilization of a mobile medical platform described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the phrase "the vicinity of a medical robotic system" may refer to a detection range of sensors (e.g., at least one of the sensors may detect an object within the vicinity of the medical robotic system) or a movement range of kinematic chains. In some cases, the phrase "within a vicinity" also encompasses "within a same room," "within a field of view," adjacent, or near.

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical robotic system, comprising:

a first kinematic chain;

one or more sensors positioned to detect one or more parameters of contact with one or more portions of the first kinematic chain, the contact including actual contact between the one or more portions of the first kinematic chain and another object;

one or more processors in communication with the one or more sensors; and memory storing instructions, which, when executed by the one or more processors, cause adjustment of a configuration of the first kinematic chain from a first configuration to a second configuration based on a constraint determined from the one or more parameters of contact with the first kinematic chain detected by the one or more sensors after the actual contact between the one or more portions of the first kinematic chain and the other object has occurred;

wherein the one or more parameters of contact form part of a probabilistic map.

2. The medical robotic system of claim 1, wherein the first kinematic chain includes a first robotic arm.

3. The medical robotic system of claim 2, wherein:

the first kinematic chain includes an adjustable arm support on which the first robotic arm is positioned; and the adjustment of the configuration of the first kinematic chain includes changing a position of the adjustable arm support.

4. The medical robotic system of any of claims 1, wherein:

the first kinematic chain includes one or more links and an end effector; and the one or more sensors include at least one of: a force/torque sensor positioned at a base of the first kinematic chain, a force/torque sensor positioned adjacent to a joint between the one or more links and the end effector, or one or more contact sensors on the one or more links.

5. The medical robotic system of any of claims 1, wherein the contact with the first kinematic chain includes contact between the first kinematic chain and an object that is not part of the medical robotic system.

6. The medical robotic system of any of claims 1, further comprising:

one or more kinematic chains not in contact with one or more portions of the first kinematic chain, wherein the instructions, when executed by the one or more processors, cause adjustment of configurations of the one or more kinematic chains based on the constraint determined from the one or more parameters of contact with the first kinematic chain detected by the one or more sensors.

7. The medical robotic system of any of claims 1, wherein the constraint is modeled as a potential field based at least in part on the one or more parameters of contact detected by the one or more sensors.

8. The medical robotic system of claim 7, wherein the potential field is also based on a probability of detecting a contact by a respective sensor of the one or more sensors.

9. The medical robotic system of any of claims 1-8, wherein the one or more parameters of the contact include one or more selected from a group consisting of: force information of the contact, location information of the contact, and direction information of the contact.

10. The medical robotic system of any of claims 1, further comprising updating the constraint and/or building a constraint map based on one or more parameters of a subsequent contact with the first kinematic chain detected by the one or more sensors.

11. The medical robotic system of claim 1, wherein the probabilistic map is determined based on the confidence of detection of a contact.

12. The medical robotic system of claim 1, wherein the one or more parameters of contact include information about whether the contact is with a moving or fixed object, and/or location information of the contact.

13. The medical robotic system of claim 12, wherein the stored instructions, when executed by the one or more processors, further cause the one or more processors to update the probabilistic map based on a finite time of constraint.

14. The medical robotic system of claim 12, wherein the stored instructions, when executed by the one or more processors, further cause the one or more processors to update the probabilistic map based on a changing probability of constraint.

15. The medical robotic system of any of claims 1, wherein the adjustment of the configuration of the first kinematic chain from the first configuration to the second configuration utilizes null space of the first kinematic chain.

16. The medical robotic system of any of claim 1, wherein the first kinematic chain is kinematically redundant.

17. A method performed by an electronic device in communication with a medical robotic system including a first kinematic chain and one or more sensors positioned to detect one or more parameters of contact with the first kinematic chain, the method comprising:

receiving one or more parameters of contact with the first kinematic chain detected by the one or more sensors; the one or more parameters of contact being associated with contact that has occurred between the first kinematic chain and another object, wherein the one or more parameters of contact form part of a probabilistic map;

determining a constraint associated with the first kinematic chain based on the one or more parameters of contact with the first kinematic chain and the probabilistic map; and causing adjustment of a configuration of the first kinematic chain from a first configuration to a second configuration based on the constraint.

18. The method of any of claims 17, further comprising causing adjustment of configurations of one or more kinematic chains not in contact with one or more portions of the first kinematic chain based on the constraint determined from the one or more parameters of contact with the first kinematic chain detected by the one or more sensors.

19. An electronic device, comprising:

one or more processors; and memory storing instructions, which, when executed by the one or more processors, cause the one or more processors to:

receive one or more parameters of contact, detected by the one or more sensors, with a first kinematic chain of a medical robotic system, the one or more parameters of contact with contact that has occurred between the first kinematic chain and another object, wherein the one or more parameters of contact form part of a probabilistic map;

determine a constraint associated with the first kinematic chain based on the one or more parameters of contact with the first kinematic chain and the probabilistic map; and cause adjustment of a configuration of the first kinematic chain from a first configuration to a second configuration based on the constraint.

* * * * *